US009839637B1

(12) United States Patent
Yamashita et al.

(10) Patent No.: US 9,839,637 B1
(45) Date of Patent: *Dec. 12, 2017

(54) PIPERAZINE-SUBSTITUTED BENZOTHIOPHENES FOR TREATMENT OF MENTAL DISORDERS

(71) Applicant: Otsuka Pharmaceutical Co., Ltd., Tokyo (JP)

(72) Inventors: Hiroshi Yamashita, Tokushima (JP); Nobuaki Ito, Tokushima (JP); Shin Miyamura, Tokushima (JP); Kunio Oshima, Tokushima (JP); Jun Matsubara, Tokushima (JP); Hideaki Kuroda, Tokushima (JP); Haruka Takahashi, Tokushima (JP); Satoshi Shimizu, Tokushima (JP); Tatsuyoshi Tanaka, Tokushima (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/697,196

(22) Filed: Sep. 6, 2017

Related U.S. Application Data

(60) Continuation of application No. 15/585,098, filed on May 2, 2017, which is a continuation of application No. 15/267,025, filed on Sep. 15, 2016, now abandoned, which is a continuation of application No. 14/928,972, filed on Oct. 30, 2015, now Pat. No. 9,480,686, which is a division of application No. 14/089,504, filed on Nov. 25, 2013, now Pat. No. 9,206,167, which is a division of application No. 13/688,108, filed on Nov. 28, 2012, now Pat. No. 8,618,109, which is a continuation of application No. 12/970,690, filed on Dec. 16, 2010, now Pat. No. 8,349,840, which is a continuation of application No. 11/659,005, filed as application No. PCT/JP2006/308162 on Apr. 12, 2006, now Pat. No. 7,888,362.

(30) Foreign Application Priority Data

Apr. 14, 2005 (JP) .................................. 2005-116698

(51) Int. Cl.
A61K 31/496 (2006.01)
C07D 409/12 (2006.01)
C07D 409/14 (2006.01)
C07D 405/12 (2006.01)

(52) U.S. Cl.
CPC .......... A61K 31/496 (2013.01); C07D 405/12 (2013.01); C07D 409/12 (2013.01); C07D 409/14 (2013.01)

(58) Field of Classification Search
None
See application file for complete search history.

(56) References Cited

U.S. PATENT DOCUMENTS

| | | | |
|---|---|---|---|
| 4,234,584 A | 11/1980 | Luttrell et al. | |
| 4,831,031 A | 5/1989 | Lowe, III et al. | |
| 4,883,795 A | 11/1989 | Lowe, III et al. | |
| 5,436,246 A | 7/1995 | Bernotas et al. | |
| 6,214,829 B1 | 4/2001 | Feenstra et al. | |
| 7,888,362 B2 | 2/2011 | Yamashita et al. | |
| 8,349,840 B2 | 1/2013 | Yamashita et al. | |
| 8,618,109 B2 | 12/2013 | Yamashita et al. | |
| 9,206,167 B2 * | 12/2015 | Yamashita ........... | C07D 409/12 |
| 9,480,686 B2 * | 11/2016 | Yamashita ........... | C07D 409/12 |
| 2017/0231983 A1 * | 8/2017 | Yamashita ........... | C07D 409/12 514/253.07 |

FOREIGN PATENT DOCUMENTS

| | | |
|---|---|---|
| EP | 0 367 141 | 5/1990 |
| EP | 0 512 525 | 11/1992 |
| EP | 0 732 332 | 9/1996 |
| EP | 0 934 932 | 8/1999 |
| EP | 0 982 304 A1 | 3/2000 |
| EP | 1 188 747 | 3/2002 |
| FR | 2 761 068 | 9/1998 |
| JP | 56-49361 | 5/1981 |
| WO | WO 1991/00863 | 1/1991 |
| WO | WO 1994/06789 | 3/1994 |
| WO | WO 1996/22290 | 7/1996 |
| WO | WO 1998/07703 | 2/1998 |
| WO | WO 2000/71517 | 11/2000 |
| WO | WO 2002/066469 | 8/2002 |
| WO | WO 2004/026864 | 4/2004 |
| WO | WO 2004/029048 | 4/2004 |
| WO | WO 2004/063162 A1 | 7/2004 |
| WO | WO 2005/019215 | 3/2005 |

OTHER PUBLICATIONS

Highlights of prescribing information—Risperdal (2009), (99 pages).
Rummel-Kluge, Christine et al., "Second-Generation Antipsychotic Drugs and Extrapyramidal Side Effects: A Systematic Review and Meta-analysis of Head-to-Head Comparisons," Schizophrenia Bulletin, vol. 38, No. 1, pp. 167-177 (2012).
Tada, Miho et al., "Combined Treatment of Quetiapine with Haloperidol in Animal Models of Antipsychotic Effect and Extrapyramidal Side Effects: Comparison With Risperidone and Chlorpromazine," Psychopharmacology 176: 94-100 (2004).
Watanabe, Yoshifumi et al., "Syntheses of 4-(Benzo[b]furan-2 or 3-yl)- and 4-(Benzo[b]-thiophen-3-yl)piperidines with 5-HT$_2$ Antagonist Activity," J. Heterocyclic Chem., 30, 445 (1993), (7 pages).

(Continued)

*Primary Examiner* — Emily Bernhardt
(74) *Attorney, Agent, or Firm* — Finnegan, Henderson, Farabow, Garrett & Dunner, LLP

(57) ABSTRACT

The present invention provides a heterocyclic compound represented by the general formula (1): The compound of the present invention has a wide treatment spectrum for mental disorders including central nervous system disorders, no side effects and high safety.

18 Claims, No Drawings

(56) References Cited

OTHER PUBLICATIONS

Kikumoto, Osamu et al., "Catalepsy Eliciting Effect and Effects on Cerebral Dopamine, Serotonin, and GABA Metabolism of Risperidone in Rats: Comparison With Haloperidol," Japan Journal Psychopharmacol. 13, pp. 39-42 (1993).
Tada, Miho et al., "The Antipsychotic Action in Mice and Influence on Extrapyramidal Symptom Due to Combined Use of Atypical Antipsychotic Medicines, Quetiapine and Haloperidol," J. New Rem. & Clin., vol. 52, No. 10 (2003), (9 pages).
Kikumoto et al., Japanese Journal of Psychopharmacology, vol. 12, No. 6, Dec. 1992, (7 pages).
Harrison et al., "Aripiprazole: A Review of its Use in Schizophrenia and Schizoaffective Disorder", ADIS Drug Evaluation, Drugs, vol. 64, No. 15, pp. 1715-1736, (2004).
Ishigooka et al., "Trends in the Clinical Development of the Second Generation Antipsychotics", Rinsho-Seishin-Yakuri, (Japanese Journal of Clinical Psychopharmacology), vol. 4, pp. 1653-1664, (2001).
Kikuchi et al., "Aripiprazole, A Novel Antipsychotic—A Dopamine $D_2$ Partial Agonist", Nou-no-Kagaku, (Brain Science), vol. 25, pp. 579-583, (2003).
Meltzer et al, "Serotonin Receptors: Their Key Role in Drugs to Treat Schizophrenia", Progress in Neuro-Psychopharmacology & Biological Psychiatry, vol. 27, pp. 1159-1172, (2003).
Moloney et al, "Synthesis and Serotonergic Activity of Variously Substituted (3-Amido)Phenylpiperazine Derivatives and Benzothiophene-4-Piperazine Derivatives: Novel Antagonists for the Vascular $5-HT_{1B}$ Receptor", European Journal of Medicinal Chemistry, vol. 39, pp. 305-321, (2004).
Murasaki et al., "The Prospect of New Pharmacological Treatment Against Psychiatric Disorders", Rinsho-Seishin-Yakuri, (Japanese Journal of Clinical Psychopharmacology), vol. 1, pp. 5-22, (1998).
Oshiro et al., "Novel Antipsychotic Agents With Dopamine Autoreceptor Agonist Properties: Synthesis and Pharmacology of 7-[4-(4-Phenyl-1-Piperazinyl)Butoxy]-3,4-Dihydro-2(1H)-Quinolinone Derivatives", J. Med. Chem., vol. 41, pp. 658-667, (1998).
Pullar et al., "LY367265, An Inhibitor of the 5-Hydroxytryptamine Transporter and 5-Hydroxytryptamine$_{2A}$ Receptor Antagonist: A Comparison With the Antidepressant, Nefazodone", European Journal of Pharmacology, vol. 407, pp. 39-46, (2000).
Search Report for Corresponding Indian Application No. 7041/DELNP/2007 dated Feb. 22, 2011.
Svensson, "α-Adrenoceptor Modulation Hypothesis of Antipsychotic Atypicality", Progress in Neuro-Psychopharmacology & Biological Psychiatry, vol. 27, pp. 1145-1158, (2003).
Toru et al., "Creativity in the Development of the Drug, Aripiprazole: A Novel Partial Dopamine $D_2$ Receptor Agonist for the Treatment of Schizophrenia", Seishin-Igaku, (Psychiatry), vol. 46, pp. 855-864, (2004).
Yagcioglu, Turkish Journal of Psychiatry, vol. 18(4), pp. 1-10 (2007).
Preventing and Reversing Weight Gain Associated with Psychiatric Medications by Dr. Candida Fink, available at http://blogs.psychcentral.com/bipolar/2008/10/preventing-and-reversing-w . . . Oct. 31, 2016.

* cited by examiner

PIPERAZINE-SUBSTITUTED BENZOTHIOPHENES FOR TREATMENT OF MENTAL DISORDERS

This is a continuation of application Ser. No. 15/585,098, filed May 2, 2017, which is a continuation of application Ser. No. 15/267,025, filed Sep. 15, 2016, which is a continuation of application Ser. No. 14/928,972, filed Oct. 30, 2015, now U.S. Pat. No. 9,480,686, issued Nov. 1, 2016, which is a division of application Ser. No. 14/089,504, filed Nov. 25, 2013, now U.S. Pat. No. 9,206,167, issued Dec. 8, 2015, which is a division of application Ser. No. 13/688,108, filed Nov. 28, 2012, now U.S. Pat. No. 8,618,109, issued Dec. 31, 2013, which is a continuation of application Ser. No. 12/970,690, filed Dec. 16, 2010, row U.S. Pat. No. 8,349,840, issued Jan. 8, 2013, which is a continuation of application Ser. No. 11/659,005, §371 (c) date of Dec. 4, 2008, now U.S. Pat. No. 7,888,362, issued Feb. 15, 2011, which is a National Stage Application of PCT/JP2006/308162, filed Apr. 12, 2006, and claims foreign priority to JP 2005-116698, filed Apr. 14, 2005, all of which are incorporated herein by reference.

TECHNICAL FIELD

The present invention relates to a novel heterocyclic compound.

BACKGROUND ART

Since causal factor of schizophrenia as well as of bipolar disorder, mood disorders and emotional disorders is heterogeneous, it is desirable that a drug has multiple pharmacological effects so as to develop wide treatment spectrum.

WO2004/026864A1 discloses that a carbostyril derivative represented by the general formula:

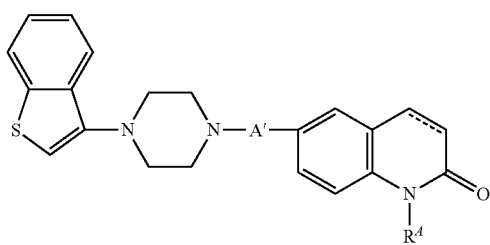

(wherein A' represents —$(CH_2)_m CH_2$—, —$(CH_2)_m O$—, etc.; m represents an integer of 1 to 4; and $R^A$ represents a hydrogen atom, a $C_{1-4}$ alkyl group which may be substituted with 1 to 3 fluorine atoms, etc.) has $D_2$ receptor antagonist activity and serotonin 2A (5-$HT_{2A}$) receptor antagonist activity and it is effective for treatment of schizophrenia and other central nervous system disorders).

However, there is no description in WO2004/026864A1 that carbostyril derivatives described in the document have $D_2$ receptor partial agonist activity, 5-$HT_{2A}$ receptor antagonist activity, $\alpha_1$ receptor antagonist activity and serotonin uptake inhibitory activity together and have a wide treatment spectrum.

WO 2005/019215 A1 discloses the compounds represented by the following formula:

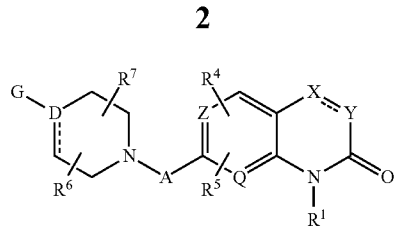

(wherein A is —$(CH_2)_m CH_2$—, —$(CH_2)_m O$— or the like; m is an integer of 2 to 5; D is N, C or the like; Z and Q are independently N, C or CH, provided that at least one of Z and Q is N; X and Y are independently C, N or the like, and the bond between X and Y is a single or double bond; $R^1$ is hydrogen, ($C_1$-$C_3$)alkyl group or the like; $R^4$, $R^5$, $R^6$ and $R^7$ each represents hydrogen, alkyl group or the like; and G represents a group of monocyclic or bicyclic compound), which bind to dopamine $D_2$ receptors. WO 2005/019215 A1 teaches that some compounds disclosed therein have an activity as partial agonists of $D_2$ receptors or an activity as antagonists of $D_2$ receptors, and may be effective for the treatment of schizophrenia and other central nervous system.

However, WO 2005/019215 A1 does not specifically disclose the compounds of the present invention.

DISCLOSURE OF THE INVENTION

An object of the present invention is to provide an antipsychotic drug which has a wider treatment spectrum, less side effects and excellent tolerability and safety as compared with well-known typical and atypical antipsychotic drugs.

The present inventors have conducted intensive studies on the above-described problem and consequently succeeded in synthesizing a novel compound which has dopamine $D_2$ receptor partial agonist activity ($D_2$ receptor partial agonist activity), serotonin 5-$HT_{2A}$ receptor antagonist activity (5-$HT_{2A}$ receptor antagonist activity) and adrenalin $\alpha_1$ receptor antagonist activity ($\alpha_1$ receptor antagonist activity) and further has serotonin uptake inhibitory effect (or serotonin reuptake inhibitory effect) together in addition to these effects. The present invention has been completed based on this finding.

The present invention provides a heterocyclic compound represented by the general formula (1):

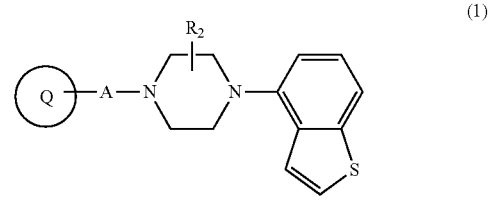

[wherein ring Q represented by

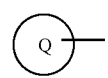

represents

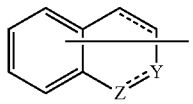

(wherein

represents —NH—CH$_2$—, —N—CH—, —CH$_2$—NH— or —CH=N—; and the carbon-carbon bond

===== between the 3-position and 4-position of the heterocyclic skeleton containing Z and Y represents a single bond or a double bond);

the ring Q may have at least one substituent selected from the group consisting of a lower alkyl group, a lower alkenyl group, a lower alkynyl group, a hydroxy group, a lower alkoxy group, a halogenated lower alkyl group, an aryl group, an aryl lower alkyl group, an aryl lower alkoxy group, an arylcarbonyl group, a lower alkenyloxy group, a lower alkanoyl group, a lower alkanoyloxy group, a cycloalkyl group, a cycloalkyl lower alkyl group, a halogen atom, a carbamoyl group which may have a lower alkyl group, a carboxy group, a lower alkoxycarbonyl group, an amino group which may have a lower alkanoyl group, a nitro group, a hydroxy lower alkyl group, an amino lower alkyl group which may have a lower alkyl group, a thienyl group, a saturated 3- to 8-membered heteromonocyclic group containing 1 to 2 nitrogen atoms-substituted lower alkyl group and an oxo group;

R$_2$ represents a hydrogen atom or a lower alkyl group; and

A represents —O-A$_1$- (wherein A$_1$ represents an alkylene group which may be substituted with a hydroxy group (wherein the alkylene group may contain one oxygen atom) or a lower alkenylene group) or a lower alkylene group;

provided that when A represents a lower alkylene group, the ring Q represents a bicyclic group selected from the group consisting of:

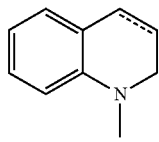 and 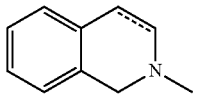

(wherein the carbon-carbon bond

===== represents a single bond or a double bond)] or a salt thereof.

The present invention provides a heterocyclic compound represented by the general formula (1), wherein the ring Q represents a bicyclic group selected from the group consisting of:

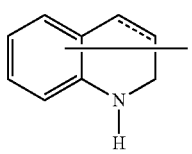 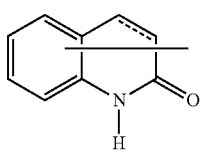

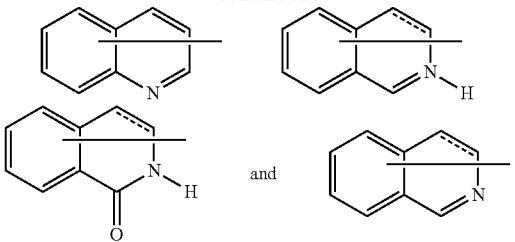

(wherein the carbon-carbon bond

===== between the 3-position and 4-position of the bicyclic heterocyclic skeleton represents a single bond or a double bond);

the ring Q may have 1 to 3 substituents selected from the group consisting of a lower alkyl group, a lower alkenyl group, a lower alkynyl group, a hydroxy group, a lower alkoxy group, a halogenated lower alkyl group, a phenyl group, a phenyl lower alkyl group, a naphthyl lower alkyl group, a phenyl lower alkoxy group, a naphthyl lower alkoxy group, a benzoyl group, a lower alkenyloxy group, a lower alkanoyl group, a lower alkanoyloxy group, a cyclo C3-C8 alkyl group, a cyclo C3-C8 alkyl lower alkyl group, a halogen atom, a carbamoyl group which may have a lower alkyl group, a carboxy group, a lower alkoxycarbonyl group, an amino group which may have lower alkanoyl group, a nitro group, a hydroxy lower alkyl group, an amino lower alkyl group which may have a lower alkyl group, a thienyl group and a saturated 5- to 6-membered heteromonocyclic group containing 1 to 2 nitrogen atoms-substituted lower alkyl group; and A represents —O-A$_1$- (wherein A$_1$ represents a C1-C6 alkylene, group which may be substituted with a hydroxy group (wherein the alkylene group may contain one oxygen atom)), or a salt thereof.

The present invention provides a heterocyclic compound represented by the general formula (1), wherein the ring Q represents a bicyclic group selected from the group consisting of:

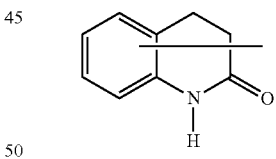 and 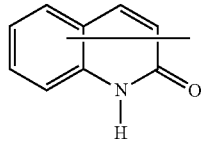

the ring Q may have 1 to 3 substituents selected from the group consisting of a lower alkyl group, a lower alkenyl group, a lower alkynyl group, a hydroxy group, a lower alkoxy group, a halogenated lower alkyl group, a phenyl group, a phenyl lower alkyl group, a naphthyl lower alkyl group, a phenyl lower alkoxy group, a naphthyl lower alkoxy group, a benzoyl group, a lower alkenyloxy group, a lower alkanoyl group, a lower alkanoyloxy group, a cyclo C3-C8 alkyl group, a cyclo C3-C8 alkyl lower alkyl group, a halogen atom, a carbamoyl group which may have a lower alkyl group, a carboxy group, a lower alkoxycarbonyl group, an amino group which may have a lower alkanoyl group, a nitro group, a hydroxy lower alkyl group, an amino lower alkyl group which may have a lower alkyl group, a phenyl group, a thienyl group and a pyrrolidinyl lower alkyl group; and A represents —O-A₁- (wherein A₁ represents a C1-C6 alkylene group which may be substituted with a hydroxy group (wherein the alkylene group may contain one oxygen atom)), or a salt thereof.

The present invention provides a heterocyclic compound represented by the general formula (1), wherein the ring Q represents a bicyclic group selected from the group consisting of:

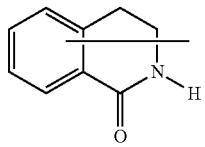 and 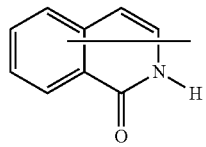

(the ring Q may have 1 to 3 substituents selected from the group consisting of a lower alkyl group, a lower alkenyl group, a lower alkynyl group, a hydroxy group, a lower alkoxy group, a halogenated lower alkyl group, a phenyl group, a phenyl lower alkyl group, a naphthyl lower alkyl group, a phenyl lower alkoxy group, a naphthyl lower alkoxy group, a benzoyl group, a lower alkenyloxy group, a lower alkanoyl group, a lower alkanoyloxy group, a cyclo C3-C8 alkyl group, a cyclo C3-C8 alkyl lower alkyl group, a halogen atom, a carbamoyl group which may have a lower alkyl group, a carboxy group, a lower alkoxycarbonyl group, an amino group which may have a lower alkanoyl group, a nitro group, a hydroxy lower alkyl group, an amino lower alkyl group which may have a lower alkyl group, a thienyl group and a pyrrolidinyl lower alkyl group) or a salt thereof.

The present invention provides a heterocyclic compound represented by the general formula (1), wherein the ring Q represents a bicyclic group selected from the group consisting of:

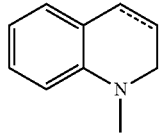 and 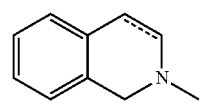

(wherein the carbon-carbon bond

===== between the 3-position and 4-position of the above-mentioned bicyclic heterocyclic skeleton represents a single bond or a double bond);

the ring Q may have 1 to 3 substituents thereon selected from the group consisting of a lower alkyl group, a lower alkenyl group, a lower alkynyl group, a hydroxy group, a lower alkoxy group, a halogenated lower alkyl group, a phenyl group, a phenyl lower alkyl group, a naphthyl lower alkyl group, a phenyl lower alkoxy group, a naphthyl lower alkoxy group, a benzoyl group, a lower alkenyloxy group, a lower alkanoyl group, a lower alkanoyloxy group, a cyclo C3-C8 alkyl group, a cyclo C3-C8 alkyl lower alkyl group, a halogen atom, a carbamoyl group which may have a lower alkyl group, a carboxy group, a lower alkoxycarbonyl group, an amino group which may have a lower alkanoyl group, a nitro group, a hydroxy lower alkyl group, an amino lower alkyl group which may have a lower alkyl group, a thienyl group, a pyrrolidinyl lower alkyl group and an oxo group; and A represents a lower alkylene group, or a salt thereof.

The present invention provides a heterocyclic compound represented by the general formula (1), wherein the ring Q represents a bicyclic group selected from the group consisting of:

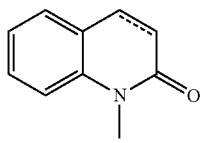 and 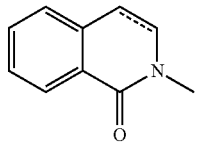

(wherein the carbon-carbon bond

===== between the 3-position and 4-position of the above-mentioned bicyclic heterocyclic skeleton represents a single bond or a double bond);

the ring Q may have 1 to 3 substituents selected from the group consisting of a lower alkyl group, a lower alkenyl group, a lower alkynyl group, a hydroxy group, a lower alkoxy group, a halogenated lower alkyl group, a phenyl group, a phenyl lower alkyl group, a naphthyl lower alkyl group, a phenyl lower alkoxy group, a naphthyl lower alkoxy group, a benzoyl group, a lower alkenyloxy group, a lower alkanoyl group, a lower alkanoyloxy group, a cyclo C3-C8 alkyl group, a cyclo C3-C8 alkyl lower alkyl group, a halogen atom, a carbamoyl group which may have a lower alkyl group, a carboxy group, a lower alkoxycarbonyl group, an amino group which may have a lower alkanoyl group, a nitro group, a hydroxy lower alkyl group, an amino lower alkyl group which may have a lower alkyl group, a thienyl group and a pyrrolidinyl lower alkyl group, or a salt thereof.

Among the heterocyclic compounds or salts thereof represented by the formula (1), preferable compounds include a compound or a salt thereof selected from:

(1) 7-[4-(4-benzo[b]thiophen-4-yl-piperazin-1-yl)butoxy]-1H-quinolin-2-one,
(2) 7-[3-(4-benzo[b]thiophen-4-yl-piperazin-1-yl)propoxy]-1H-quinolin-2-one,
(3) 7-[3-(4-benzo[b]thiophen-4-yl-piperazin-1-yl)propoxy]-3,4-dihydro-1H-quinolin-2-one,
(4) 7-[4-(4-benzo[b]thiophen-4-yl-piperazin-1-yl)butoxy]-3,4-dihydro-1H-quinolin-2-one,
(5) 7-[4-(4-benzo[b]thiophen-4-yl-piperazin-1-yl)butoxy]-1-methyl-3,4-dihydro-1H-quinolin-2-one and
(6) 6-[3-(4-benzo[b]thiophen-4-yl-piperazin-1-yl)propoxy]-3,4-dihydro-1H-quinolin-2-one; or a salt thereof.

In addition, among the heterocyclic compounds or salts thereof represented by the formula (1), preferable compounds include a compound or a salt thereof selected from:

(1) 7-[3-(4-benzo[b]thiophen-4-yl-piperazin-1-yl)propoxy]-3,4-dihydro-2H-isoquinolin-1-one
(2) 7-[3-(4-benzo[b]thiophen-4-yl-piperazin-1-yl)propoxy]-2-methyl-3,4-dihydro-2H-isoquinolin-1-one,
(3) 7-[4-(4-benzo[b]thiophen-4-yl-piperazin-1-yl)butoxy]-2-methyl-3,4-dihydro-2H-isoquinolin-1-one,
(4) 7-[4-(4-benzo[b]thiophen-4-yl-piperazin-1-yl)butoxy]-3,4-dihydro-2H-isoquinolin-1-one,
(5) 7-[3-(4-benzo[b]thiophen-4-yl-piperazin-1-yl)propoxy]-2H-isoquinolin-1-one and
(6) 7-(3-(4-benzo[b]thiophen-4-yl-piperazin-1-yl)propoxy]-2-methyl-2H-isoquinolin-1-one; or a salt thereof.

The present invention provides a pharmaceutical composition comprising a heterocyclic compound represented by the formula (1) or a salt thereof as an active ingredient mixed with a pharmaceutically acceptable carrier. The pharmaceutical composition according to the present invention can be effectively used for the treatment or prevention of central nervous system disorders.

The pharmaceutical composition according to the present invention can be used as a pharmaceutical composition for treating or preventing central nervous system disorders selected from the group consisting of schizophrenia; refractory, intractable or chronic schizophrenia; emotional disturbance; psychotic disorder; mood disorder; bipolar I type disorder; bipolar II type disorder; depression; endogenous depression; major depression; melancholy and refractory depression; dysthymic disorder; cyclothymic disorder; panic attack; panic disorder; agoraphobia; social phobia; obsessive-compulsive disorder; post-traumatic stress disorder; generalized anxiety disorder; acute stress disorder; hysteria; somatization disorder; conversion disorder; pain disorder; hypochondriasis; factitious disorder; dissociative disorder; sexual dysfunction; sexual desire disorder; sexual arousal disorder; erectile dysfunction; anorexia nervosa; bulimia nervosa; sleep disorder; adjustment disorder; alcohol abuse; alcohol intoxication; drug addiction; stimulant intoxication; narcotism; anhedonia; iatrogenic anhedonia; anhedonia of a psychic or mental cause; anhedonia associated with depression; anhedonia associated with schizophrenia; delirium; cognitive impairment; cognitive impairment associated with Alzheimer's disease, Parkinson's disease and other neurodegenerative diseases; cognitive impairment caused by Alzheimer's disease, Parkinson's disease and associated neurodegenerative diseases; cognitive impairment of schizophrenia; cognitive impairment caused by refractory, intractable or chronic schizophrenia; vomiting; motion sickness; obesity; migraine; pain(ache); mental retardation; autism disorder (autism); Tourette's disorder; tic disorder; attention-deficit/hyperactivity disorder; conduct disorder; and Down's syndrome.

The present invention provides a process for producing a pharmaceutical composition comprising mixing a heterocyclic compound represented by the above-described formula (1) or a salt thereof with a pharmaceutically acceptable carrier.

The present invention provides use of a heterocyclic compound represented by the above-described formula (1) or a salt thereof as a drug. Specifically provided is of a heterocyclic compound represented by the above-described formula (1) or a salt thereof, as a dopamine $D_2$ receptor partial agonist and/or a serotonin 5-$HT_{2A}$ receptor antagonist and/or an adrenaline $\alpha_1$ receptor antagonist and/or a serotonin uptake inhibitor (or a serotonin reuptake inhibitor).

The present invention provides a method for treating or preventing a central nervous system disorder comprising administering a compound represented by the above-described formula (1) or a salt thereof to human or animal.

The present invention provides a process for producing a heterocyclic compound represented by the above-described formula (1):

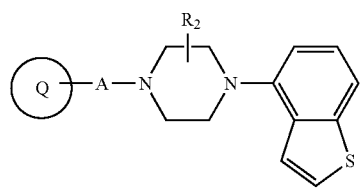

or a salt thereof, characterized by comprising a reaction of a compound represented by the formula:

(wherein the ring Q and A are the same as defined above, and $X_1$ represents a halogen atom or a group which causes a substitution reaction the same as in a halogen atom) or a salt thereof with a compound represented by the formula:

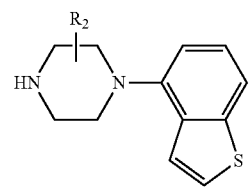

(wherein $R_2$ is the same as defined above) or a salt thereof.

Specifically, respective groups shown in the above general formula (1) are as follows.

As a lower alkyl group, a linear or branched alkyl group having 1 to 6 carbon atoms can be mentioned. More specifically, methyl, ethyl, n-propyl, isopropyl, n-butyl, isobutyl, tert-butyl, sec-butyl, n-pentyl, 1-ethylpropyl, isopentyl, neopentyl, n-hexyl, 1,2,2-trimethylpropyl, 3,3-dimethylbutyl, 2-ethylbutyl, isohexyl, 3-methylpentyl groups are included.

As a lower alkoxy group, a linear or branched alkoxy group having 1 to 6 carbon atoms can be mentioned. More specifically, methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy, 3-methylpentyloxy groups are included.

As a lower alkenyl group, a linear or branched alkenyl group having 1 to 3 double bonds and 2 to 6 carbon atoms can be mentioned including the both of trans and cis configurations. More specifically, vinyl, 1-propenyl, 2-propenyl, 1-methyl-1-propenyl, 2-methyl-1-propenyl, 2-methyl-2-propenyl, 2-propenyl, 2-butenyl, l-butenyl, 3-butenyl, 2-pentenyl, 1-pentenyl, 3-pentenyl, 4-pentenyl, 1,3-butadienyl, 1,3-pentadienyl, 2-penten-4-yl, 2-hexenyl, l-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, 1,4-hexadienyl groups are included.

As a lower alkynyl group, a linear or branched alkynyl group having 2 to 6 carbon atoms can be mentioned. More specifically, ethynyl, 2-propynyl, 2-butynyl, 3-butynyl, 1-methyl-2-propynyl, 2-pentynyl, 2-hexynyl groups are included.

As a halogen atom, fluorine atom, chlorine atom, bromine atom and iodine atom can be mentioned.

As a halogenated lower alkyl group, a lower alkyl group as illustrated above substituted with 1 to 7 halogen atoms, preferably 1 to 3 halogen atoms can be mentioned. More specifically, fluoromethyl, difluoromethyl, trifluoromethyl, chloromethyl, dichloromethyl, trichloromethyl, bromomethyl, dibromomethyl, dichlorofluoromethyl, 2,2-difluoroethyl, 2,2,2-trifluoroethyl, pentafluoroethyl, 2-fluoroethyl, 2-chloroethyl, 3,3,3-trifluoropropyl, heptafluoropropyl, 2,2,3,3,3-pentafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl, 6-chlorohexyl, perfluorohexyl are included.

As an aryl group, for example, phenyl, biphenyl, naphthyl groups can be mentioned and as a substituent on the phenyl ring or naphthalene ring, a lower alkyl group (preferably linear or branched alkyl group having 1 to 6 carbon atoms) as illustrated above, lower alkoxy group (preferably linear or branched alkoxy group having 1 to 6 carbon atoms) as illustrated above, and phenyl, biphenyl, or naphthyl groups which may have 1 to 3 groups selected from a nitro group and a halogen atom are included.

Specific examples of an aryl group include phenyl, 2- (or 3- or 4-)methylphenyl, 2- (or 3- or 4-) nitrophenyl, 2- (or 3- or 4-)methoxyphenyl, 2- (or 3- or 4-)chlorophenyl, biphenyl, α-naphthyl, β-naphthyl groups.

As an aryl lower alkyl group, a lower alkyl group (preferably linear or branched alkyl group having 1 to 6 carbon atoms) as illustrated above which has 1 to 3, preferably one aryl group as illustrated above can be mentioned.

Specific examples of an aryl lower alkyl group include benzyl, 2- (or 3- or 4-)methylbenzyl, 2-(or 3- or 4-) nitrobenzyl, 2- (or 3- or 4-) methoxybenzyl, 2- (or 3- or 4-) chlorobenzyl, 1- (or 2-)phenylethyl, 1-methyl-1-phenylethyl, 1,1-dimethyl-2-phenylethyl, 1,1-dimethyl-3-phenylpropyl, α-naphthylmethyl, β-naphthylmethyl groups.

As an aryl lower alkoxy group, a lower alkoxy group (preferably linear or branched alkoxy group having 1 to 6 carbon atoms) as illustrated above which has 1 to 3, preferably one aryl group as illustrated above can be mentioned. Specific examples of an aryl lower alkoxy group include benzyloxy, 2- (or 3- or 4-) methylbenzyloxy, 2- (or 3- or 4-) nitrobenzyloxy, 2-(or 3- or 4-)methoxy benzyloxy, 2- (or 3- or 4-) chlorobenzyl, 1- (or 2-)phenylethoxy, 1-methyl-1-phenyl ethoxy, 1,1-dimethyl-2-phenyl ethoxy, 1,1-dimethyl-3-phenyl propoxy, α-naphtnylmethoxy, β-naphthylmethoxy groups.

As an aryl moiety of an arylcarbonyl group, an aryl group as illustrated above can be mentioned. Specific examples of an arylcarbonyl group include benzoyl, 2- (or 3- or 4-)methylbenzoyl, 2- (or 3- or 4-) nitrobenzoyl, 2- (or 3- or 4-)methoxybenzoyl, 2- (or 3- or 4-)chlorobenzoyl, α-naphthoyl, β-naphthoyl groups.

As a lower alkenyloxy group, a lower alkenyloxy group having a lower alkenyl group (preferably a linear or branched alkenyloxy group having 1 to 3 double bonds and 2 to 6 carbon atoms) as illustrated above can be mentioned. More specifically included are vinyloxy, 1-propenyloxy, 1-methyl-1-propenyloxy, 2-methyl-1-propenyloxy, 2-propenyloxy, 2-butenyloxy, 1-butenyloxy, 3-butenyloxy, 2-pentenyloxy, 1-pentenyloxy, 3-pentenyloxy, 4-pentenyloxy, 1,3-butadienyloxy, 1,3-pentadienyloxy, 2-penten-4-yloxy, 2-hexenyloxy, 1-hexenyloxy, 5-hexenyloxy, 3-hexenyloxy, 4-hexenyloxy, 3,3-dimethyl-1-propenyloxy, 2-ethyl-1-propenyloxy, 1,3,5-hexatrienyloxy, 1,3-hexadienyloxy, 1,4-hexadienyloxy groups.

As a lower alkanoyl group, a linear or branched alkanoyl group having 1 to 6 carbon atoms can be mentioned. More specifically, formyl, acetyl, propionyl, butyryl, isobutyryl, pentanoyl, tert-butylcarbonyl, hexanoyl groups are included.

As a lower alkanoyloxy group, a linear or branched alkanoyloxy group having 1 to 6 carbon atoms can be mentioned. More specifically, formyloxy, acetyloxy, propionyloxy, butyryloxy, isobutyryloxy, pentanoyloxy, tert-butylcarbonyloxy, hexanoyloxy groups are included.

As a cycloalkyl group, a cyclo C3-C8 alkyl group having 3 to 8 carbon atoms can be mentioned. Examples thereof include cyclopropyl, cyclobutyl, cyclopentyl, cyclohexyl, cycloheptyl, cyclooctyl groups.

As a cycloalkyl lower alkyl group, a lower alkyl group as illustrated above which has 1 to 3, preferably one cycloalkyl group (preferably, cyclo C3-C8 alkyl group having 3 to 8 carbon atoms) as illustrated above can be mentioned. More specifically included are cyclopropylmethyl, cyclohexylmethyl, 2-cyclopropylethyl, 1-cyclobutylethyl, cyclopentylmethyl, 3-cyclopentylpropyl, 4-cyclohexylbutyl, 5-cycloheptylpentyl, 6-cyclooctylhexyl, 1,1-dimethyl-2-cyclohexylethyl, 2-methyl-3-cyclopropylpropyl groups.

As a carbamoyl group which may have a lower alkyl group, a carbamoyl group which may have 1 to 2 lower alkyl group (preferably, alkyl group having 1 to 6 carbon atoms) as illustrated above can be mentioned. More specifically included are carbamoyl, N-methylcarbamoyl, N,N-dimethylcarbamoyl, N-methyl-N-ethylcarbamoyl groups.

As a lower alkoxycarbonyl group, those having a lower alkoxy moiety as illustrated above, preferably a linear or branched alkoxycarbonyl group having 1 to 6 carbon atoms can be mentioned. More specifically included are methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, n-pentyloxycarbonyl, neopentyloxy, n-hexyloxy carbonyl, isohexyloxycarbonyl, 3-methylpentyloxycarbonyl groups.

As an amino group which may have a lower alkanoyl group, those having one lower alkanoyl group as illustrated above (preferably a linear or branched alkanoyl group having 1 to 6 carbon atoms) can be mentioned. More specifically, examples include amino, N-formylamino, N-acetylamino groups.

As a hydroxy lower alkyl group, a lower alkyl group (preferably, a linear or branched alkyl group having 1 to 6 carbon atoms) as illustrated above having 1 to 5, preferably 1 to 3 hydroxy groups can be mentioned. More specifically included are hydroxymethyl, 2-hydroxyethyl, 1-hydroxyethyl, 3-hydroxypropyl, 2,3-dihydroxypropyl, 4-hydroxybutyl, 3,4-dihydroxybutyl, 1,1-dimethyl-2-hydroxyethyl, 5-hydroxypentyl, 6-hydroxyhexyl, 3,3-dimethyl-3-hydroxypropyl, 2-methyl-3-hydroxypropyl, 2,3,4-trihydroxybutyl, perhydroxyhexyl groups.

As an amino lower alkyl group which may have a lower alkyl group, a lower alkyl group (preferably, a linear or branched alkyl group having 1 to 6 carbon atoms) as illustrated above having 1 to 5, preferably one amino group which may have 1 to 2 lower alkyl-group (preferably, a linear or branched alkyl group having 1 to 6 carbon atoms) as illustrated above can be mentioned. More specifically, examples of such an amino lower alkyl group which may have a lower alkyl group include aminomethyl, 2-aminoethyl, 1-aminoethyl, 3-aminopropyl, 4-aminobutyl, 5-aminopentyl, 6-aminohexyl, 1,1-dimethyl-2-methyl-3-aminopropyl, N,N-dimethylaminomethyl, N-methyl-N-ethylaminomethyl, N-methylaminomethyl, 2-(N-methylamino)ethyl, 1-methyl-2-(N,N-dimethylamino)ethyl, 2-(N,N-dimethylamino)ethyl, 2-(N,N-diethylamino)ethyl, 2-(N,N-diisopropylamino)ethyl, 3-(N,N-dimethylamino)propyl, 3-(N,N-diethylamino)propyl groups.

As a saturated 3- to 8-membered heteromonocyclic group containing 1 to 2 nitrogen atoms group, for example, azetidinyl, pyrrolidinyl, imidazolidinyl, pyrazolidinyl, piperidinyl, piperazinyl morpholinyl, thiomorpholinyl groups (preferably a saturated 5- to 6-membered heteromonocyclic group containing 1 to 2 nitrogen atoms group such as pyrrolidinyl, imidazolidinyl, piperidinyl, piperidino, pyrazolidinyl and piperazinyl) can be mentioned.

As a saturated 3- to 8-membered heteromonocyclic group containing 1 to 2 nitrogen atoms-substituted lower alkyl group, a lower alkyl (preferably, a linear or branched alkyl group having 1 to 6 carbon atoms) as illustrated above having 1 to 2 (preferably one) a saturated 3- to 8-membered (preferably 5- to 6-membered) heteromonocyclic group containing 1 to 2 nitrogen atoms as illustrated above can be mentioned. More specifically, [(1-, 2- or 3-)azetidinyl] methyl, [(1-, 2- or 3-) pyrrolidinyl]methyl, [(1-, 2- or 4-)-imidazolidinyl]methyl, [(1-, 3- or 4-)-pyrazolidinyl]methyl, [(1-, 2-, 3- or 4-)-piperidyl]methyl, [(2-, 3- or 4-)morpholinyl]methyl, 2-[(1-, 2- or 3-)pyrrolidinyl]ethyl, 1-[(1-, 2- or 3-)-pyrrolidinyl]ethyl, 3-[(1-, 2- or 3-)piperidyl] propyl, 4-[(1-, 2- or 3-)pyrrolidinyl]butyl, 5-[(1-, 2- or 3-)-piperidyl] pentyl are included.

Examples of an alkylene group which may be substituted with a hydroxy group (wherein the alkylene group may contain one oxygen atom) include a linear or branched alkylene group (wherein the alkylene group may contain one oxygen atom) having 1 to 12 (preferably 1 to 6) carbon atoms such as methylene, ethylene, trimethylene, 2-methyltrimethylene, 2-hydroxytrimethylene, 3-hydroxytetramethylene, 3-methyltetramethylene, 2,2-dimethyltrimethylene, 1-methyltrimethylene, methylmethylene, ethylmethylene, tetramethylene, pentamethylene, hexamethylene, 2-ethoxyethylene (—$CH_2CH_2OCH_2CH_2$—), methoxymethylene (—$CH_2OCH_2$—), 1-ethoxyethylene (—$CH_2CH_2OCH$ ($CH_3$)—), 2-methoxyethylene (—$CH_2OCH_2CH_2$—), 2-propoxyethylene (—$CH_2CH_2CH_2OCH_2CH_2$—), 3-iso-propoxytrimethylene (—$CH(CH_3)CH_2OCH_2CH_2$—), 4-butoxytetramethylene (—$CH_2CH_2CH_2CH_2OCH_2CH_2CH_2CH_2$—), 5-pentyloxypentamethylene (—$CH_2CH_2CH_2CH_2OCH_2CH_2CH_2CH_2CH_2$—), 6-hexyl oxyhexamethylene (—$CH_2CH_2CH_2CH_2CH_2CH_2OCH_2CH_2CH_2CH_2CH_2CH_2$—), 1,1-dimethyl-2-methoxyethylene (—$CH_2OCH_2C(CH_3)_2$—), 2-methyl-3-ethoxytrimethylene (—$CH_2CH_2OCH_2CH(CH_3)CH_2$—) 3-methoxytrimethylene (—$CH_2OCH_2CH_2CH_2CH_2$—) groups.

Examples of a lower alkenylene group include a linear or branched alkenylene group having 1 to 3 double bonds and 2 to 6 carbon atoms such as vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-pentene-4-ylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, 1,4-hexadienylene groups.

Examples of a lower alkylene group include a linear or branched alkenylene group having 1 to 6 carbon atoms such as methylene, ethylene, trimethylene, 2-methyltrimethylene, 3-methyltetramethylene, 2,2-dimethyltrimethylene, 1-methyltrimethylene, methylmethylene, ethylmethylene, tetramethylene, pentamethylene and hexamethylene groups.

The heterocyclic compound represented by the above-described general formula (1) can be produced in various kinds of methods, but, for example, it can be produced by a method shown in the following reaction formula.

[Reaction Formula 1]

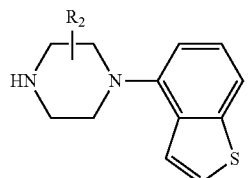

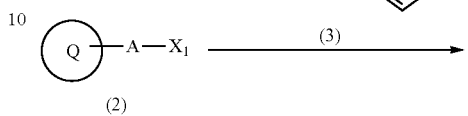

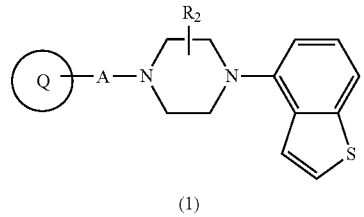

(wherein ring Q, A and $R_2$ are the same as defined above, and $X_1$ represents a halogen atom or a group which causes a substitution reaction the same as in a halogen atom).

Here, examples of a group which causes a substitution reaction the same as in a. halogen atom include a lower alkanesulfonyloxy group, an arylsulfonyloxy group and an aralkylsulfonyloxy group.

A halogen atom shown as $X_1$ in the general formula (2) is the same as defined above.

As a lower alkanesulfonyloxy group shown as $X_1$, examples include a linear or branched alkanesulfonyloxy group having 1 to 6 carbon atoms such as methanesulfonyloxy, ethanesulfonloxy, n-propanesulfonyloxy, isopropanesulfonyloxy, n-butanesulfonyloxy, tert-butanesulfonyloxy, n-pentanesulfonyloxy and n-hexanesulfonyloxy groups.

As an arylsulfonyloxy group shown as $X_1$, examples include phenylsulfonyloxy and naphthylsulfonyloxy groups which may have 1 to 3 substituents selected from the group consisting of a linear or branched alkyl group having 1 to 6 carbon atoms, a linear or branched alkoxy group having 1 to 6 carbon atoms, a nitro group and a halogen atom on the phenyl ring, for example. Specific examples of a phenylsulfonyloxy group which may have a substituent include phenylsulfonyloxy, 4-methylphenylsulfonyloxy, 2-methylphenylsulfonyloxy, 4-nitrophenylsulphonyloxy, 4-methoxyphenylsulfonyloxy, 2-nitrophenylsulphonyloxy, 3-chlorophenylsulphonyloxy groups. Specific examples of a naphthylsulfonyloxy group include α-naphthyl sulfonyloxy, β-naphthyl sulfonyloxy groups.

As an aralkylsulfonyloxy group shown as $X_1$, examples include a linear or branched alkanesulfonyloxy group having 1 to 6 carbon atoms and substituted with a phenyl group, a linear or branched alkanesulfonyloxy group having 1 to 6 carbon atoms and substituted with a naphthyl group, which groups which may have 1 to 3 substituents selected from the group consisting of a linear or branched alkyl group having 1 to 6 carbon atoms, a linear or branched alkoxy group having 1 to 6 carbon atoms, a nitro group and a halogen atom on the phenyl ring, for example. Specific examples of a phenylsulfonyloxy group substituted with a naphthyl group as mentioned above include benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy groups. Specific examples of an alkanesulfonyloxy group substituted with a naphthyl group as mentioned above include α-naphthylmethyl sulfonyloxy, β-naphthylmethyl sulfonyloxy groups.

The reaction of a compound represented by the general formula (2) and a compound represented by the general formula (3) is performed without solvent or in an inert solvent in the absence or presence of a basic compound.

Examples of an inert solvent include water; ethers such as dioxane, tetrahydrofuran, diethyl ether, diethylene glycol dimethyl ether, ethylene glycol dimethyl ether; aromatic hydrocarbons such as benzene, toluene, xylene; lower alcohols such as methanol, ethanol, isopropanol; ketones such as acetone, methyl ethyl ketone; polar solvents such as N,N-dimethylformamide (DMF), dimethylsulfoxide (DMSO), hexamethylphosphoric triamide, acetonitrile.

As a basic compound, known compounds can be widely used and examples include alkali metal hydroxides such as sodium hydroxide, potassium hydroxide, cesium hydroxide, lithium hydroxide; alkali metal carbonates such as sodium carbonate, potassium carbonate, cesium carbonate, lithium carbonate; alkaline metal hydrogen carbonates such as lithium hydrogen carbonate, sodium hydrogen carbonate, potassium bicarbonate; alkaline metals such as sodium, potassium; inorganic bases such as sodium amide, sodium hydride, potassium hydride and alkaline metal alcoholates such as sodium methoxide, sodium ethoxide, potassium methoxide, potassium ethoxide; organic bases such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO).

As for these basic compounds, one kind of compound alone or two or more in combination can be used.

The amount to be used of a basic compound is usually 0.5 to 10 times, preferably 0.5 to 6 times molar amount of a compound of the general formula (2).

The above-described reaction can be performed with addition of an alkaline metal iodide such as potassium iodide, sodium iodide as a reaction accelerator, if necessary.

As for the ratio to be used of a compound of the general formula (2) and a compound of the general formula (3) in the above-mentioned reaction Formula 1, the latter may be usually at least 0.5 times, preferably, 0.5 to 5 times molar amount of the former.

The above-described reaction is performed usually from room temperature to 200° C., preferably from room temperature to 150° C. and generally completed in about 1 to 30 hours.

-continued

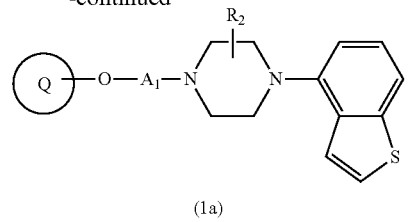

(1a)

(wherein ring Q, $R_2$ and $A_1$ are the same as defined above. $X_2$ represents a hydroxy group, a halogen atom or a group which causes a substitution reaction similar to a halogen atom).

The reaction of a compound represented by the general formula (4) and a compound represented by the general formula (5a) is performed under similar reaction condition as in the reaction of a compound represented by the general formula (2) and a compound represented by the general formula (3) in the above-mentioned Reaction Formula 1.

In the case of a compound (5a) in which $X_2$ represents a hydroxy group, the reaction of a compound (4) and a compound (5a) can be performed in an appropriate solvent in the presence of a condensing agent.

As for the solvent usable here, specific examples include halogenated hydrocarbons such as chloroform, dichloromethane, dichloroethane, carbon tetrachloride; aromatic hydrocarbons such as benzene, toluene, xylene; ethers such as diethyl ether, diisopropyl ether, tetrahydrofuran, dimethoxyethane; esters such as methyl acetate, ethyl acetate, isopropyl acetate; polar solvent such as acetonitrile, pyridine, acetone, DMF, DMSO, hexamethylphosphoric triamide or a mixed solvent of these.

As a condensing agent, azocarboxylates such as diethyl azodicarboxylate and a mixture of phosphorus compounds such as triphenylphosphine can be mentioned.

The amount of a condensing agent to be used is usually at least equimolar, preferably equimolar to 2 times the amount of compound (4).

The amount of compound (5a) to be used is usually at least equimolar, preferably equimolar to 2 times the amount of compound (4).

This reaction precedes usually 0 to 200° C., preferably 0 to 150° C. and generally completed in about 1 to 10 hours.

[Reaction Formula 2]

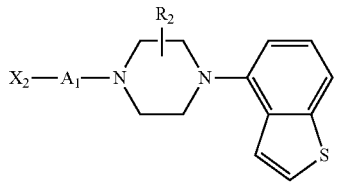

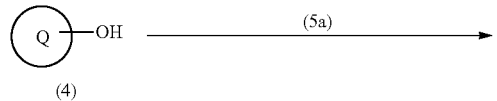

[Reaction Formula 3]

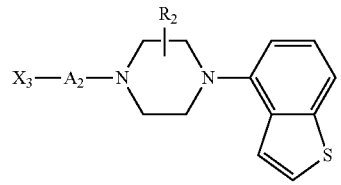

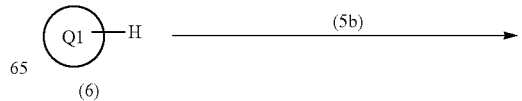

-continued

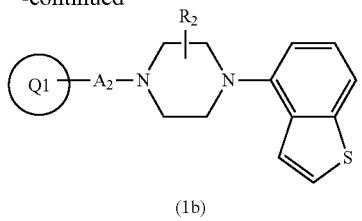

(1b)

[wherein $R_2$ is the same as above, $X_3$ represents a halogen atom or a group which causes a substitution reaction similar to a halogen atom, $A_2$ represents a lower alkylene group, and the ring Q1 represents a bicyclic group selected from the group consisting of:

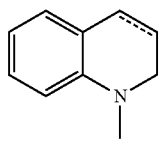 and 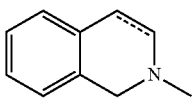

(wherein the carbon-carbon bond

===== represents a single bond or a double bond);

the ring Q1 may have at least one substituent selected from the group consisting of a lower alkyl group, a lower alkenyl group, a lower alkynyl group, a hydroxy group, a lower alkoxy group, an aryl group, an aryl lower alkyl group, an aryl lower alkoxy group, a lower alkenyloxy group, a lower alkanoyl group, a lower alkanoyloxy group, a cycloalkyl group, a cycloalkyl (lower) alkyl group, a halogen atom, a carbamoyl group which may have a lower alkyl group, a carboxy group, a lower alkoxycarbonyl group, an amino group which may have a lower alkanoyl group, a nitro group, a hydroxy lower alkyl group, an amino lower alkyl group which may have a lower alkyl group, a thienyl group, a saturated 3- to 8-membered heteromonocyclic group containing 1 to 2 nitrogen atoms-substituted lower alkyl group and an oxo group].

The reaction of a compound represented by the general formula (6) and a compound represented by the general formula (5b) is performed under similar reaction condition as in the reaction of a compound represented by the general formula (2) and a compound represented by the general formula (3) in the above-mentioned Reaction Formula 1.

The compound represented by the general formula (2), which is used as a starting material, can be produced, for example, according to the following reaction Formula 4 and the compound represented by the general formula (5) can be produced, for example, according to the Reaction Formula 5 below respectively.

[Reaction Formula 4]

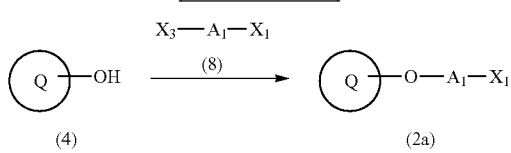

(wherein ring Q, $A_1$, $X_1$ and $X_3$ are the same as above).

The reaction of a compound represented by the general formula (4) and a compound represented by the general formula (8) is performed under similar reaction condition as in the reaction of a compound represented by the general formula (4) and a compound represented by the general formula (5a) in the above-mentioned Reaction Formula 2.

[Reaction Formula 5]

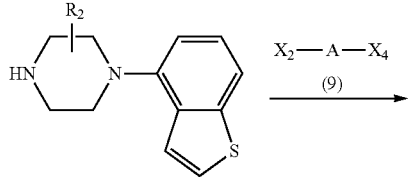

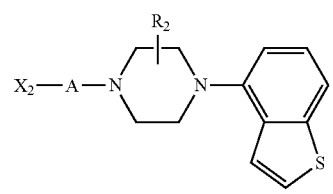

(wherein $R_2$, A and $X_2$ are the same as above, and $X_4$ represents a halogen atom or a group which causes a substitution reaction the same as in a halogen atom).

The reaction of a compound represented by the general formula (3) and a compound represented by the general formula (9) is performed under similar reaction condition as in the reaction of a compound represented by the general formula (2) and a compound represented by the general formula (3) in the above-mentioned Reaction Formula 1. Both the compound of the general formula (3) and the compound of the general formula (9) are well-known compounds readily available.

In compound (1), a compound having a hydroxy group at ring Q can be produced by treating a compound having a methoxy group at ring Q in compound (1) in the presence of an acid in an appropriate solvent or without solvent.

As for inert solvent usable here, examples include water; aromatic hydrocarbons such as benzene, toluene, xylene; ethers such as diethyl ether, tetrahydrofuran, dioxane, monoglyme, diglyme; halogenated hydrocarbons such as dichloromethane, dichloroethane, chloroform, carbon tetrachloride; lower alcohols such as methanol, ethanol, isopropanol, butanol, tert-butanol, ethylene glycol; fatty acids such as acetic acid; esters such as ethyl acetate, methyl acetate; ketones such as acetone, methyl ethyl ketone; acetonitrile, pyridine, DMF, DMSO, hexamethylphosphoric triamide or a mixed solvent of these.

As for the acid, examples include mineral acids such as hydrobromic acid, hydrochloric acid, concentrated sulfuric acid; fatty acids such as formic acid, acetic acid, organic acids such as p-toluenesulfonic acid; Lewis acids such as aluminum chloride, zinc chloride, iron chloride, tin chloride, boron trifluoride, boron tribromide; iodides such as sodium iodide, potassium iodides; a mixture of a Lewis acid and an iodide as mentioned above.

It is suitable that such an acid is usually used at 0.1 to 15 times, preferably 0.5 to 10 times molar amount of compound (1). When the reaction is effected without solvent, the acid is usually used in a large excess amount.

This reaction is performed usually 0 to 150° C., preferably at around 0 to 100° C., and generally completed for about 0.5 to 75 hours.

The starting compounds used in each of the above reaction formula may be suitable salt, the object compound obtained by each of the reaction may form a suitable salt. Such suitable salts include the preferable salts of compound (1) exemplified below.

The preferable salts of compound (1) are pharmacologically acceptable salts and examples include metal salts such as alkali metal salts (for example, sodium salt potassium salt, etc.), alkaline earth metal salts (for example, calcium salt, magnesium salt, etc.), salts of inorganic bases such as ammonium salt, alkaline metal carbonates (for example, lithium carbonate, potassium carbonate, sodium carbonate, cesium carbonate, etc.), alkaline metal hydrogen carbonates (for example, lithium hydrogen carbonate, sodium hydrogen carbonate, potassium bicarbonate, etc.), alkali metal hydroxides (for example, lithium hydroxide, sodium hydroxide, potassium hydroxide, cesium hydroxide, etc.); for example, salts of organic bases such as tri(lower)alkylamine (for example, trimethylamine, triethylamine, N-ethyldiisopropylamine), pyridine, quinoline, piperidine, imidazole, picoline, dimethylaminopyridine, dimethylaniline, N-(lower) alkyl-morpholine (for example, N-methylmorpholine), 1,5-diazabicyclo[4.3.0]nonene-5 (DBN), 1,8-diazabicyclo [5.4.0]undecene-7 (DBU), 1,4-diazabicyclo[2.2.2] octane (DABCO); salts of inorganic acids such as hydrochloride, hydrobromide, hydroiodide, sulfate, nitrate, phosphate; salts of organic acids such as formate, acetate, propionate, oxalate, malonate, succinate, fumarate, maleate, lactate, malate, citrate, tartrate, carbonate, picrate, methanesulfonate, ethanesulfonate, p-toluenesulfonate, glutamate.

In addition, compounds in the form in which solvate (for example, hydrate, ethanolate, etc.) was added to the starting compounds and object compound shown in each of the reaction formulae are included in each of the general formulas. As a preferable solvate, hydrate can be mentioned.

Each of the object compounds obtained by each of the general formulas can be isolated and purified from the reaction mixture by, for example, subjecting the reaction mixture to isolation operation such as filtration, concentration and extraction after cooling to separate a crude reaction product followed by conventional purification operation such as column chromatography or recrystallization.

The compound represented by the general formula (1) of the present invention naturally encompasses isomers such as geometrical isomer, stereoisomer and enantiomer.

The compound of the general formula (1) and a salt thereof can be used in a common form of pharmaceutical preparation. The pharmaceutical preparation is prepared by using usually used diluent or excipient such as filler, extending agent, binder, humectant, disintegrating agent, surfactant and lubricant. As for this pharmaceutical preparation, various forms can be selected depending on the purpose of treatment, and typical examples include a tablet, pill, powder, solution, suspension, emulsion, granule, capsule, suppository, and injection (solution, suspension).

For shaping in tablet form, various materials conventionally well known as carrier in the art can be widely used. As examples, excipient such as lactose, saccharose, sodium chloride, glucose, urea, starch, calcium carbonate, kaolin, crystalline cellulose, silicate; binder such as water, ethanol, propanol, simple syrup, glucose solution, starch liquid, gelatine solution, carboxymethylcellulose, shellac, methylcellulose, potassium phosphate, polyvinylpyrrolidone; disintegrating agent such as dried starch, sodium alginate, agar powder, laminaran powder, sodium hydrogen carbonate, calcium carbonate, polyoxyethylene sorbitan fatty acid ester, sodium lauryl sulfate, stearic acid monoglyceride, starch, lactose; disintegration preventing agent such as saccharose, stearin, cacao butter, hydrogenated oil; sorbefacient such as quaternary ammonium base, sodium lauryl sulfate; moisturizing agent such as glycerine, starch; absorbing agent such as starch, lactose, kaolin, bentonite, colloidal silica; lubricant such as purified talc, stearate, borate powder, polyethylene glycol can be used, for example. Furthermore, the tablet may be a tablet provided with conventional coating as required, for example, sugar-coated tablet, gelatine encapsulated tablet, enteric coating tablet, film coated tablet or double tablet, multilayer tablet.

For shaping in pill form, various materials conventionally well known as carrier in the art can be widely used. As examples, excipient such as glucose, lactose, starch, cacao butter, hydrogenated vegetable oil, kaolin, talc; binder such as powdered gum arabic, powdered tragacanth, gelatine, ethanol; disintegrating agent such as laminaran, agar can be used, for example.

For shaping in suppository form, various materials conventionally well known as carrier can be widely used. Examples thereof include polyethylene glycol, cacao butter, higher alcohol, esters of higher alcohol, gelatine, semisynthesized glyceride, for example.

A capsule is usually prepared according to a conventional method by mixing active ingredient compounds with various carrier exemplified above and filling them into a hard gelatin capsule, a soft capsule or the like.

When prepared as injection liquid, it is preferable that solution, emulsion and suspension are sterilized and isotonic to the blood and for forming in these modes, any of those conventionally used in the art as diluent can be used, and, for example, water, ethyl alcohol, macrogol, propylene glycol, ethoxylated isostearyl alcohol, polyoxylated isostearyl alcohol, polyoxyethylene sorbitan fatty acid ester, etc. can be used.

The pharmaceutical preparation may contain common salt, glucose or glycerine in an amount sufficient to prepare an isotonic solution in this case, and conventional solubilizer, buffer, soothing agent may be also added. Pigment, preservative, aromatic, flavor, sweetening and other pharmaceuticals may be further contained as required.

The amount of a compound of the general formula (1) or a salt thereof to be contained in the pharmaceutical preparation of the present invention is not particularly limited but usually about 1 to 70% by weight in the preparation composition is suitable and preferably about 1 to 30% by weight.

There is not limitation in particular in the way of administration of the pharmaceutical preparation of the present invention and may be administered by a method in accordance with specific form of the preparation, age, sex and the other conditions of a patient, severity of disease, etc. For example, in the case of tablet, pill, solution, suspension, emulsion, granule and capsule, it is orally administered. In the case of injection, it is intravenously administered alone or in a mixture with conventional replacement fluid such as glucose and amino acids, and if necessary, and the preparation alone may be also administered intramuscularly, intracutaneously, subcutaneously or interperitoneally. It is administered in rectum in the case of suppository.

Applied dose of the pharmaceutical preparation of the present invention is appropriately selected in accordance with dosage regimen, age, sex and the other conditions of a patient, severity of disease, etc., but it is suitable that the amount of the active ingredient compound is usually about 0.1 to 10 mg per 1 kg of body weight per day. In addition, it is desirable that the active ingredient compound is contained in the preparation of a dosage unit form in the range of about 1 to 200 mg.

The compound of the present invention has $D_2$ receptor partial agonist effect, 5-$HT_{2A}$ receptor antagonist effect and serotonin uptake inhibitory effect (or serotonin uptake inhibitory effect).

The $D_2$ receptor partial agonist effect suppresses dopaminergic (DA) neurotransmission when it is enhanced, and accelerates the DA neurotransmission when it is lowered and thus has a function to stabilize the DA neurotransmission to a normal state (dopamine system stabilizer). According to this function, excellent clinically improving effect on the conditions based on the DA abnormal neurotransmission (enhancement and lowering), for example, improving effect on positive and negative symptoms, improving effect on cognitive impairment, improving effect on depressive symptom, etc. are developed without developing side effects (See Michio Toru: Seishin-Igaku (Psychiatry), Vol. 46, pp. 855-864 (2004), Tetsuro Kikuchi. and Tsuyoshi Hirose: Nou-no-Kagaku (Brain Science), Vol. 25, pp. 579-583 (2003) and Harrison, T. S. and Perry, C. M.: Drugs 64: 1715-1736, 2004).

5-$HT_{2A}$ receptor antagonist effect reduces extrapyramidal side effects, develops superior clinical effects, and is effective for improvement of negative symptoms, improvement of cognitive impairment, improvement of depression condition, improvement of insomnia, for example (See Jun Ishigooka and Ken Inada: Rinsho-Seishin-Yakuri (Japanese Journal of Clinical Psychopharmacology), Vol. 4, pp. 1653-1664 (2001), Mitsukuni Murasaki: Rinsho-Seishin-Yakuri (Japanese Journal of Clinical Psychopharmacology), Vol. 1, pp. 5-22 (1998), Puller, I. A. et al., Eur. J. Pharmacol., 407:39-46, 2000, and Meltzer, H. Y. et al, Frog. Neuro-Psychopharmacol. Biol. Psychiatry 27: 1159-1172, 2003).

Serotonin uptake inhibitory effect (or serotonin reuptake inhibitory effect) is effective for improving depressive symptoms, for example (See Mitsukuni Murasaki: Rinsho-Seishin-Yakuri (Japanese Journal of Clinical Psychopharmacology), Vol. 1, pp. 5-22 (1998)).

The compounds of the present invention are excellent in all of these three effects, or remarkably excellent in one or two of these effects.

In addition, some of the compounds of the present invention have $\alpha_1$ receptor antagonist effect in addition to the above-described effects. The $\alpha_1$ receptor antagonist effect is effective for improving positive symptoms of schizophrenia (See Svensson, T. H.: Prog. Neuro-Psychopharmacol. Biol. Psychiatry 27: 1145-1158, 2003).

Therefore, the compounds of the present invention have a wide treatment spectrum for and excellent clinical effect on schizophrenia and other central nervous system disorders.

Accordingly, the compounds of the present invention are extremely effective for the treatment or prevention of central nervous system disorders including the group consisting of schizophrenia; refractory, intractable or chronic schizophrenia; emotional disturbance; psychotic disorder; mood disorder; bipolar disorder (for example, bipolar I type disorder and bipolar II type disorder); depression; endogenous depression; major depression; melancholy and refractory depression; dysthymic disorder; cyclothymic disorder; anxiety disorder (for example, panic attack, panic disorder, agoraphobia, social phobia, obsessive-compulsive disorder, post-traumatic stress disorder, generalized anxiety disorder, acute stress disorder, etc.); somatoform disorder (for example, hysteria, somatization disorder, conversion disorder, pain disorder, hypochondriasis, etc.); factitious disorder; dissociative disorder; sexual disorder (for example, sexual dysfunction, sexual desire disorder, sexual arousal disorder, erectile dysfunction, etc.); eating disorder (for example, anorexia nervosa, bulimia nervosa, etc.); sleep disorder; adjustment disorder; substance-related disorder (for example, alcohol abuse, alcohol intoxication, drug addiction, stimulant intoxication, narcotism, etc.); anhedonia (for example, iatrogenic anhedonia, anhedonia of a psychic or mental cause, anhedonia associated with depression, anhedonia associated with schizophrenia, etc.); delirium; cognitive impairment; cognitive impairment associated with Alzheimer's disease, Parkinson's disease, and other neurodegenerative diseases; cognitive impairment caused by Alzheimer's disease, Parkinson's disease and associated neurodegenerative diseases; cognitive impairment of schizophrenia; cognitive impairment caused by refractory, intractable or chronic schizophrenia; vomiting; motion sickness; obesity; migraine; pain (ache); mental retardation; autism disorder (autism); Tourette's disorder; tic disorder; attention-deficit/hyperactivity disorder; conduct disorder; and Down's syndrome.

Furthermore, the compounds of the present invention have little or no side effects and they are excellent in safety and tolerability.

EXAMPLES

Hereinbelow, the present invention will be further made clear with reference to Reference Examples, Examples, Pharmacological Test Examples and Preparation Examples.

Reference Example 1

Preparation of 7-(4-chlorobutoxy)-1H-quinolin-2-one

After 14.7 g of potassium hydroxide was added to a methanol (250 ml) suspension of 30 g of 7-hydroxy-1H-quinolin-2-one, which was stirred at 50° C. to form a solution, 65 ml of 1-bromo-4-chlorobutane was added thereto and refluxed for 8 hours. After cooling to room temperature, precipitated crystals were separated by filtration. They were purified by silica gel column chromatography (dichloromethane:methanol=100:3), and 29.6 g of 7-(4-chlorobutoxy)-1H-quinolin-2-one was obtained in the form of a white powder.

$^1$H-NMR (CDCl$_3$) δppm:
1.95-2.15 (4H, m), 3.60-3.70 (2H, m), 4.10 (2H, t, J=5.6 Hz), 6.56 (1H, dd, J=9.0 Hz, 3.8 Hz), 6.81 (1H, dd, J=8.7 Hz, 2.4 Hz), 6.85 (1H, d, J=2.3 Hz), 7.45 (1H, d, J=8.7 Hz), 7.75 (1H, d, J=9.4 Hz), 12.54 (1H, brs).

Reference Example 2

Preparation of 7-(4-chlorobutoxy)-4-methyl-1H-quinolin-2-one 7-(4-chlorobutoxy)-4-methyl-1H-quinolin-2-one was prepared from 7-hydroxy-4-methyl-1H-quinolin-2-one by a similar method as in Reference Example 1.

White Powder $^1$H-NMR (DMSO-d$_6$) δppm:
1.80-2.00 (4H, m), 2.37 (3H, s), 3.72 (2H, t, J=6.0 Hz), 4.05 (2H, t, J=6.0 Hz), 6.20 (1H, s), 6.75-6.90 (2H, m), 7.60 (1H, d, J=8.5 Hz), 11.42 (1H, brs).

Reference Example 3

Preparation of 7-methoxy-3-methyl-1H-quinolin-2-one 30.7 ml of triethylsilane was added to a trifluoroacetic acid (300 ml) solution of 13 g of 7-methoxy-2-oxo-1,2-dihydroquinoline3-carbaldehyde while being stirred under ice-cooling and stirred at room temperature overnight. The reaction solution was poured into ice water and extracted with dichloromethane and, after washed with water, dried over magnesium sulfate, and the solvent was evaporated under reduced pressure. The residue was purified by silica gel column chromatography (dichloromethane:methanol=30:1), and 11.1 g of 7-methoxy-3-methyl-1H-quinolin-2-one was obtained in the form of a white powder.

$^1$H-NMR (DMSO-$d_6$) δppm:
2.02 (3H, s), 3.77 (3H, s), 6.70-6.80 (2H, m), 7.45 (1H, d, J=8.4 Hz), 7.64 (1H, s), 11.56 (1H, brs).

Reference Example 4

Preparation of 7-hydroxy-3-methyl-1H-quinolin-2-one

47% hydrobromic acid (60 ml) suspension of 2.12 g of 7-methoxy-3-methyl-1H-quinolin-2-one was refluxed for six hours. After cooling, water was added to the reaction solution and precipitated crystals were separated by filtration. The crystals were dissolved in a mixed solvent of dichloromethane and methanol and dried over magnesium sulfate, and the solvent was evaporated under reduced pressure and 1.7 g of 7-hydroxy-3-methyl-1H-quinolin-2-one was obtained in the form of a brown powder.

$^1$H-NMR (DMSO-$d_6$) δppm:
1.99 (3H, s), 6.57 (1H, dd, J=8.5 Hz, 2.5 Hz), 6.65 (1H, d, J=2.5 Hz), 7.34 (1H, d, J=8.5 Hz), 7.58 (1H, s), 9.90 (1H, s), 11.48 (1H, brs).

Reference Example 5

Preparation of 7-(3-chloropropoxy)-3-methyl-1H-quinolin-2-one

By a similar method as in Reference Example 1, 7-(3-chloropropoxy)-3-methyl-1H-quinolin-2-one in the form of a white powder was prepared from 7-hydroxy-3-methyl-1H-quinolin-2-one using 1-bromo-3-chloropropane.

$^1$H-NMR (DMSO-$d_6$) δppm:
2.05 (3H, s), 2.15-2.25 (2H, m), 3.81 (2H, t, J=6.5 Hz), 4.11 (2H, t, J=6.0 Hz), 6.75-6.85 (2H, m), 7.48 (1H, d, J=8.5 Hz), 7.67 (1H, s), 11.59 (1H, brs).

Reference Example 6

Preparation of 7-(4-chlorobutoxy)-3-methyl-1H-quinolin-2-one

By a similar method as in Reference Example 1, 7-(4-chlorobutoxy)-3-methyl-1H-quinolin-2-one in the form of a white powder was prepared from 7-hydroxy-3-methyl-1H-quinolin-2-one using 1-bromo-4-chlorobutane.

$^1$H-NMR (DMSO-$d_6$) δppm:
1.80-1.95 (4H, m), 2.04 (3H, s), 3.72 (2H, t, J=6.0 Hz), 4.03 (2H, t, J=6.0 Hz), 6.75-6.80 (2H, m), 7.47 (1H, d, J=8.5 Hz), 7.66 (1H, s), 11.58 (1H, brs).

Reference Example 7

Preparation of 1-(4-chlorobutyl)-1H-quinolin-2-one 0.30 g of sodium hydride (60% oily) was added to a dimethylformamide (20 ml) solution of 1.0 g of 1H-quinolin-2-one while being stirred under ice-cooling and stirred at room temperature for 0.5 hour, and after that 1.6 ml of 1-bromo-4-chlorobutane was added and stirred at room temperature for 14 hours. Water was added to the reaction solution, which was then extracted with ethyl acetate and, after washed with water, dried over magnesium sulfate, and the solvent was evaporated under reduced pressure. The residue was purified by silica gel column chromatography (n-hexane:ethyl acetate=3:1), and 1.02 g of 1-(4-chlorobutyl)-1H-quinolin-2-one was obtained in the form of colorless oil.

$^1$H-NMR (CDCl$_3$) δppm:
1.85-2.00 (4H, m), 3.60-3.65 (2H, m), 4.35 (2H, t, J=7.0 Hz), 6.70 (1H, d, J=9.5 Hz), 7.23 (1H, dd, J=8.6 Hz, 7.5 Hz), 7.38 (1H, d, J=8.9 Hz), 7.54-7.62 (2H, m), 7.68 (1H, d, J=9.5 Hz).

Reference Example 8

Preparation of 1-(5-chloropentyl)-1H-quinolin-2-one

By a similar method as in Reference Example 7, 1-(5-chloropentyl)-1H-quinolin-2-one in the form of colorless oil was prepared from 1H-quinolin-2-one using 1-bromo-5-chloropentane.

$^1$H-NMR (CDCl$_3$) δppm:
1.55-1.70 (2H, m), 1.75-1.95 (4H, m), 3.56 (2H, t, J=6.6 Hz), 4.31 (2H, t, J=7.8 Hz), 6.70 (1H, d, J=9.5 Hz), 7.23 (1H, dd, J=7.3 Hz, 7.3 Hz), 7.35 (1H, d, J=8.9 Hz), 7.54-7.60 (2H, m), 7.67 (1H, d, J=9.4 Hz).

Reference Example 9

Preparation of 7-(4-chloro-(Z)-2-butenyloxy)-3,4-dihydro-1H-quinolin-2-one

A mixture of 1.0 g of 7-hydroxy-3,4-dihydro-1H-quinolin-2-one, 1.7 g of potassium carbonate, 3.2 ml of cis-1,4-dichloro-2-butene and 50 ml of dimethylformamide was stirred at room temperature overnight. Water was added to the reaction solution, which was then extracted with ethyl acetate and, after washed with water, dried over magnesium sulfate, and the solvent was evaporated under reduced pressure. The residue was purified by silica gel column chromatography (n-hexane:ethyl acetate=3:1), and 7-(4-chloro-(Z)-2-butenyloxy)-3,4-dihydro-1H-quinolin-2-one (1.3 g) was obtained in the form of a white powder.

$^1$H-NMR (CDCl$_3$) δppm:
2.62 (2H, t, J=6.3 Hz), 2.90 (2H, t, J=6.3 Hz), 4.16 (2H, d, J=6.3 Hz), 4.62 (2H, d, J=4.6 Hz), 5.86-5.90 (2H, m), 6.31 (1H, d, J=2.5 Hz), 6.54 (1H, dd, J=8.3 Hz, 2.5 Hz), 7.06 (1H, d, J=8.3 Hz), 7.56 (1H, brs).

Reference Example 10

Preparation of 2-methyl-4-(2-oxo-1,2,3,4-tetrahydroquinolin-7-yloxy)butyric acid methyl ester 4.98 g of sodium iodide was added to an acetonitrile (70 ml) solution of 5 g of 4-chloro-2-methylbutyric acid methyl ester and it was refluxed for 3 hours. Water was added to the reaction solution, which was then extracted with dichloromethane and, after washed with water, dried over magnesium sulfate, and the solvent was evaporated under reduced pressure. The residue was added to a mixture of 4.33 g of 7-hydroxy-3, 4-dihydro-1H-quinolin-2-one, 6.0 g of potassium carbonate and dimethylformamide (90 ml) and stirred at 80° C. for 6 hours. Water was added to the reaction solution, which was then extracted with ethyl acetate and, after washed with water, dried over magnesium sulfate, and the solvent was evaporated under reduced pressure. The residue was purified by silica gel column chromatography (dichloromethane:methanol=100:3), and 6.0 g of 2-methyl-4-(2-oxo-1,2,3,4-tetrahydroquinolin-7-yloxy)butyric acid methyl ester was obtained in the form of a yellow oil.

$^1$H-NMR (CDCl$_3$) δppm:
1.23 (3H, d, J=7.1 Hz), 1.75-1.90 (1H, m), 2.10-2.25 (1H, m), 2.55-2.65 (2H, m), 2.72 (1H, q, J=7.0 Hz), 2.80-2.90 (2H, m), 3.68 (3H, s), 3.95 (2H, t, J=6.2 Hz), 6.33 (1H, d, J=2.3 Hz), 6.49 (1H, dd, J=8.3 Hz, 2.21 Hz), 7.02 (1H, d, J=8.3 Hz), 8.41 (1H, brs).

Reference Example 11

Preparation of 7-(4-hydroxy-3-methylbutoxy)-3,4-dihydro-1H-quinolin-2-one 6 g of 2-methyl-4-(2-oxo-1,2,3,4-tetrahydroquinolin-7-yloxy)butyric acid methyl ester was added dropwise to a tetrahydrofuran (200 ml) suspension of 1.6 g of lithium aluminum hydride while being stirred under ice-cooling and stirred at the same temperature for 2 hours. While being stirred under ice-cooling, saturated Rochelle salt aqueous solution was added, which was extracted with diethyl ether and, after washed with water, dried over magnesium sulfate, and the solvent was evaporated under reduced pressure. The residue was purified by silica gel column chromatography (dichloromethane:methanol=40:1), and 2.8 g of 7-(4-hydroxy-3-methylbutoxy)-3,4-dihydro-1H-quinolin-2-one was obtained in the form of a yellow oil.

$^1$H-NMR (CDCl$_3$) δppm:
0.99 (3H, d, J=6.5 Hz), 1.60-2.05 (3H, m), 2.60-2.65 (2H, m), 2.85-2.95 (2H, m), 3.55 (2H, t, J=5.3 Hz), 3.95-4.10 (2H, m), 6.38 (1H, d, J=2.5 Hz), 6.53 (1H, dd, J=8.3 Hz, 2.4 Hz), 7.04 (1H, d, J=8.3 Hz), 8.59 (1H, brs).

Reference Example 12

Preparation of methanesulfonic acid 2-methyl-4-(2-oxo-1,2,3,4-tetrahydroquinolin-7-yloxy)butyl ester Methanesulfonyl chloride (1.0 ml) was added to a dichloromethane (80 ml) solution of 2.8 g of 7-(4-hydroxy-3-methyl butoxy)-3,4-dihydro-1H-quinolin-2-one and 2.4 ml of triethylamine while being stirred under ice-cooling and stirred at room temperature overnight. Water was added to the reaction solution, which was then extracted with dichloromethane and, after washed with water, dried over magnesium sulfate, and the solvent was evaporated under reduced pressure. The residue was purified by silica gel column chromatography (dichloromethane:methanol=30:1), and methanesulfonic acid 2-methyl-4-(2-oxo-1,2,3,4-tetrahydroquinolin-7-yloxy)butyl ester (2.8 g) was obtained in the form of a green powder.

$^1$H-NMR (CDCl$_3$) δppm:
1.07 (3H, d, J=6.8 Hz), 1.60-1.80 (1H, m), 1.90-2.00 (1H, m), 2.15-2.25 (1H, m), 2.50-2.65 (2H, m), 2.90 (2H, t, J=7.3 Hz), 3.95-4.10 (2H, m), 4.10-4.20 (2H, m), 6.33 (1H, d, J=2.5 Hz), 6.51 (1H, dd, J=8.3 Hz, 2.5 Hz), 7.05 (1H, d, J=8.3 Hz), 8.16 (1H, brs).

Reference Example 13

Preparation of 7-(4-bromo-(E)-2-butenyloxy)-3,4-dihydro-1H-quinolin-2-one

By a similar method as in Reference Example 9, 7-(4-bromo-(E)-2-butenyloxy)-3,4-dihydro-1H-quinolin-2-one in the form of a white powder was prepared from 7-hydroxy-3,4-dihydro-1H-quinolin-2-one using trans-1,4-dibromo-2-butene.

$^1$H-NMR (CDCl$_3$) δppm:
2.61 (2H, t, J=7.5 Hz), 2.89 (2H, t, J=7.5 Hz), 3.98 (2H, d, J=7.0 Hz), 4.51 (2H, d, J=4.8 Hz), 5.90-6.10 (2H, m), 6.43 (1H, d, J=2.1 Hz), 6.51 (1H, dd, J=8.2 Hz, 2.1 Hz), 7.03 (1H, d, J=8.2 Hz), 9.35 (1H, brs).

Reference Example 14

Preparation of 7-(4-chlorobutoxy)-4-methyl-3,4-dihydro-1H-quinolin-2-one

Boron tribromide (1 M dichloromethane solution, 6.2 ml) was added to a dichloromethane solution (5 ml) of 0.54 g of 7-methoxy-4-methyl-3,4-dihydro-1H-quinolin-2-one while being stirred under ice-cooling and 0.23 g of precipitated crude crystals were separated by filtration. 0.2 g of potassium carbonate and 0.45 ml of 1-bromo-4-chlorobutane were added to an acetonitrile (2.5 ml)-water (2.5 ml) solution of the crude crystals and refluxed for 6 hours. Water was added to the reaction solution, which was then extracted with ethyl acetate and, after washed with water, dried over magnesium sulfate, and the solvent was evaporated under reduced pressure. The residue was purified by silica gel column chromatography (dichloromethane:methanol=50:1), and 7-(4-chlorobutoxy)-4-methyl-3,4-dihydro-1H-quinolin-2-one (0.29 g) was obtained in the form of a white powder.

$^1$H-NMR (DMSO-d$_6$) δ ppm:
1.28 (3H, d, J=7.0 Hz), 1.85-2.05 (4H, m), 2.35-2.45 (1H, m), 2.65-2.75 (1H, m), 3.00-3.15 (1H, m), 3.62 (2H, t, J=6.0 Hz), 3.97 (2H, t, J=6.0 Hz), 6.32 (1H, d, J=2.5 Hz), 6.55 (1H, dd, J=8.5 Hz, 2.5 Hz), 7.08 (1H, d, J=8.5 Hz), 7.96 (1H, brs).

Reference Example 15

Preparation of 7-[2-(2-chloroethoxy)ethoxy]-3,4-dihydro-1H-quinolin-2-one

A mixture of 7.0 g of 7-hydroxy-3,4-dihydro-1H-quinolin-2-one, 7.1 g of potassium carbonate, 30 ml of bis-2-chloroethyl ether and 400 ml of acetonitrile was refluxed for 2 days. Water was added to the reaction solution, which was then extracted with dichloromethane and, after washed with water, dried over magnesium sulfate, and the solvent was evaporated under reduced pressure. The residue was purified by silica gel column chromatography (dichloromethane:methanol=40:1), and 8.3 g of 7-[2-(2-chloroethoxy)ethoxy]-3,4-dihydro-1H-quinolin-2-one was obtained in the form of a white powder.

$^1$H-NMR (CDCl$_3$) δ ppm:
2.61 (2H, t, J=7.4 Hz), 2.90 (2H, t, J=7.4 Hz), 3.66 (2H, t, J=5.8 Hz), 3.74-3.88 (4H, m), 4.11 (2H, t, J=4.7 Hz), 6.36 (1H, d, J=2.2 Hz), 6.54 (1H, dd, J=8.3 Hz, 2.2 Hz), 7.05 (1H, d, J=8.3 Hz), 8.01 (1H, m).

Reference Example 16

Preparation of 6-(3-chloropropoxy)-3,4-dihydro-1H-quinolin-2-one

By a similar method as in Reference Example 9, 6-(3-chloropropoxy)-3,4-dihydro-1H-quinolin-2-one in the form of a white powder was prepared from 6-hydroxy-3,4-dihydro-1H-quinolin-2-one using 1-bromo-3-chloropropane.

$^1$H-NMR (CDCl$_3$) δppm:
2.15-2.35 (2N, m), 2.55-2.65 (2H, m), 2.90-3.00 (2H, m), 3.50-3.80 (2H, m), 4.00-4.10 (2H, m), 6.73 (3H, brs), 8.68 (1H, brs).

Reference Example 17

Preparation of 6-(4-bromobutoxy)-3,4-dihydro-1H-quinolin-2-one

By a similar method as in Reference Example 9, 6-(4-bromobutoxy)-3,4-dihydro-1H-quinolin-2-one in the form of a white powder was prepared from 6-hydroxy-3,4-dihydro-1H-quinolin-2-one using 1,4-dibromobutane.

$^1$H-NMR (DMSO-d$_6$) δppm:
1.75-1.85 (2H, m), 1.90-2.00 (2H, m), 2.30-2.45 (2H, m), 2.75-2.85 (2H, m), 3.58 (2H, t, J=6.5 Hz), 3.91 (2H, t, J=6.5 Hz), 6.70-6.80 (3H, m), 9.88 (1H, brs).

Reference Example 18

Preparation of 1-(5-chloropentyl)-3,4-dihydro-1H-quinolin-2-one

By a similar method as in Reference Example 7, 1-(5-chloropentyl)-3,4-dihydro-1H-quinolin-2-one in the form of colorless oil was prepared from 3,4-dihydro-1H-quinolin-2-one using 1-bromo-5-chloropentane.

$^1$H-NMR (CDCl$_3$) δ ppm:
1.45-1.60 (2H, m), 1.60-1.75 (2H, m), 1.75-1.90 (2H, m), 2.60-2.70 (2H, m), 2.85-2.95 (2H, m), 3.54 (2H, d, J=6.6 Hz), 3.59 (2H, d, J=7.7 Hz), 6.76-7.04 (2H, m), 7.15-7.29 (2H, m).

Reference Example 19

Preparation of 2-(5-chloropentyl)-3,4-dihydro-2H-isoquinolin-1-one

By a similar method as in Reference Example 7, 2-(5-chloropentyl)-3,4-dihydro-2H-isoquinolin-1-one in the form of brown oil was prepared from 3,4-dihydro-2H-isoquinolin-1-one using 1-bromo-5-chloropentane.

$^1$H-NMR (CDCl$_3$) δppm:
1.50-2.00 (6H, m), 2.99 (2H, t, J=6.6 Hz), 3.52-3.60 (6H, m), 7.17 (1H, d, J=7.3 Hz), 7.31-7.44 (2H, m), 8.07 (1H, dd, J=1.3 Hz, 7.5 Hz).

Reference Example 20

Preparation of 7-(3-chloropropoxy)-3,4-dihydro-2H-isoquinolin-1-one

By a similar method as in Reference Example 9, 7-(3-chloropropoxy)-3,4-dihydro-2H-isoquinolin-1-one in the form of brown oil was prepared from 7-hydroxy-3,4-dihydro-2H-isoquinolin-1-one using 1-bromo-3-chloropropane.

$^1$H-NMR (CDCl$_3$) δppm:
2.20-2.40 (2H, m), 2.90-3.00 (2H, m), 3.50-3.80 (4H, m), 4.15-4.20 (4H, m), 6.48 (1H, brs), 7.01 (1H, dd, J=4.0 Hz, 1.5 Hz), 7.13 (1H, d, J=4.0 Hz), 7.59 (1H, d, J=1.4 Hz).

Reference Example 21

Preparation of 7-hydroxy-2-methyl-3,4-dihydro-2H-isoquinolin-1-one

By a similar method as in Reference Example 4, 7-hydroxy-2-methyl-3,4-dihydro-2H-isoquinolin-1-one in the form of a brown powder was prepared from 7-methoxy-2-methyl-3,4-dihydro-2H-isoquinolin-1-one.

$^1$H-NMR (DMSO-d$_6$) δppm:
2.84 (2H, t, J=6.5 Hz), 3.01 (3H, s), 3.47 (2H, t, J=6.6 Hz), 6.85 (1H, dd, J=8.1 Hz, 2.5 Hz), 7.08 (1H, d, J=8.1 Hz), 7.29 (1H, d, J=2.5 Hz), 9.49 (1H, s).

Reference Example 22

Preparation of 7-(4-chlorobutoxy)-2-methyl-3,4-dihydro-2H-isoquinolin-1-one

By a similar method as in Reference Example 9, 7-(4-chlorobutoxy)-2-methyl-3,4-dihydro-2H-isoquinolin-1-one in the form of a brown oil was prepared from 7-hydroxy-2-methyl-3,4-dihydro-2H-isoquinolin-1-one using 1-bromo-4-chlorobutane.

$^1$H-NMR (CDCl$_3$) δppm:
1.90-2.00 (4H, m), 2.93 (2H, t, J=6.8 Hz), 3.15 (3H, s), 3.45-3.65 (4H, m), 4.04 (2H, t, J=5.8 Hz), 6.95 (1H, dd, J=8.3 Hz, 2.5 Hz), 7.07 (1H, d, J=8.3 Hz), 7.59 (1H, d, J=2.5 Hz).

Reference Example 23

Preparation of 7-(4-chlorobutoxy)-3,4-dihydro-2H-isoquinolin-1-one

By a similar method as in Reference Example 9, 7-(4-chlorobutoxy)-3,4-dihydro-2H-isoquinolin-1-one in the form of a white powder was prepared from 7-hydroxy-3,4-dihydro-2H-isoquinolin-1-one using 1-bromo-4-chlorobutane.

$^1$H-NMR (CDCl$_3$) δppm:
1.93-2.00 (4H, m), 2.88-2.96 (2H, m), 3.51-3.58 (2H, m), 3.62 (2H, t, J=6.2 Hz), 4.05 (2H, t, J=5.7 Hz), 6.25 (1H, s), 7.00 (1H, dd, J=8.3 Hz, 2.7 Hz), 7.13 (1H, d, J=8.3 Hz), 7.57 (1H, d, J=2.7 Hz).

Reference Example 24

Preparation of 2-(4-chlorobutyl)-2H-isoquinolin-1-one

By a similar method as in Reference Example 7, 2-(4-chlorobutyl)-2H-isoquinolin-1-one in the form of a yellow oil was prepared from 2H-isoquinolin-1-one using 1-bromo-4-chlorobutane.

¹H-NMR (CDCl₃) δ ppm:
1.80-2.00 (4H, m), 3.59 (2H, t, J=6.3 Hz), 4.05 (2H, t, J=7.0 Hz), 6.51 (1H, d, J=7.4 Hz), 7.05 (1H, d, J=7.4 Hz), 7.46-7.52 (2H, m), 7.63 (1H, m), 8.42 (1H, d, J=8.1 Hz).

Reference Example 25

Preparation of 7-(3-chloropropoxy)-2H-isoquinolin-1-one

By a similar method as in Reference Example 9, 7-(3-chloropropoxy)-2H-isoquinolin-1-one in the form of a white powder was prepared from 7-hydroxy-2H-isoquinolin-1-one using 1-bromo-3-chloropropane.
¹H-NMR (CDCl₃) δppm:
2.30 (2H, quint, J=6.1 Hz), 3.78 (2H, t, J=6.4 Hz), 4.28 (2H, t, J=5.9 Hz), 6.54 (1H, d, J=7.1 Hz), 7.06 (1H, d, J=6.6 Hz), 7.29 (1H, dd, J=8.7 Hz, 2.7 Hz), 7.51 (1H, d, J=8.7 Hz), 7.82 (1H, d, J=2.7 Hz), 10.64 (1H, s).

Reference Example 26

Preparation of 7-(3-chloropropoxy)-2-ethyl-2H-isoquinolin-1-one

By a similar method as in Reference Example 7, 7-(3-chloropropoxy)-2-ethyl-2H-isoquinolin-1-one in the form of a colorless oil was prepared from 7-(3-chloropropoxy)-2H-isoquinolin-1-one using ethyl iodide.
¹H-NMR (CDCl₃) δppm:
1.38 (3H, t, J=7.2 Hz), 2.29 (2H, quint, J=6.1 Hz), 3.76 (2H, t, J=6.4 Hz), 4.07 (2H, q, J=7.2 Hz), 4.25 (2H, d, J=5.8 Hz), 6.48 (1H, d, J=7.3 Hz), 6.98 (1H, d, J=7.3 Hz), 7.23 (1H, dd, J=8.7 Hz, 2.7 Hz), 7.44 (1H, d, J=8.7 Hz), 7.85 (1H, d, J=2.6 Hz).

Reference Example 27

Preparation of 2-(4-chlorobutyl)-7-methoxy-2H-isoquinolin-1-one

By a similar method as in Reference Example 7, 2-(4-chlorobutyl)-7-methoxy-2H-isoquinolin-1-one in the form of colorless oil was prepared from 7-methoxy-2H-isoquinolin-1-one using 1-bromo-4-chlorobutane.
¹H-NMR (CDCl₃) δppm:
1.64-2.00 (4H, m), 3.59 (2H, t, J=6.3 Hz), 3.93 (3H, s), 4.06 (2H, t, J=6.9 Hz), 6.49 (1H, d, J=7.3 Hz), 6.96 (1H, d, J=7.3 Hz), 7.25 (1H, dd, J=8.6 Hz, 2.7 Hz), 7.45 (1H, d, J=8.7 Hz), 7.83 (1H, d, J=2.7 Hz).

Reference Example 28

Preparation of 6-(3-chloropropoxy)-2H-isoquinolin-1-one

By a similar method as in Reference Example 9, 6-(3-chloropropoxy)-2H-isoquinolin-1-one in the form of a pale yellow powder was prepared from 6-hydroxy-2H-isoquinolin-1-one using 1-bromo-3-chloropropane.
¹H-NMR (CDCl₃) δ ppm:
2.30 (2H, quint, J=6.0 Hz), 3.78 (2H, t, J=6.2 Hz), 4.24 (2H, t, J=5.9 Hz), 6.46 (1H, d, J=7.2 Hz), 6.93 (1H, d, J=2.4 Hz), 7.05-7.12 (2H, m), 8.33 (1H, d, J=8.9 Hz), 10.33 (1H, s).

Reference Example 29

Preparation of 7-(3-chloropropoxy)-2-methyl-3,4-dihydro-2H-isoquinolin-1-one

By a similar method as in Reference Example 9, 7-(3-chloropropoxy)-2-methyl-3,4-dihydro-2H-isoquinolin-1-one in the form of a brown powder was prepared from 7-hydroxy-2-methyl-3,4-dihydro-2H-isoquinolin-1-one using 1-bromo-3-chloropropane.
¹H-NMR (CDCl₃) δppm:
2.15-2.35 (2H, m), 2.85-3.00 (2H, m), 3.15 (3H, s), 3.50-3.80 (4H, m), 4.10-4.20 (2H, m), 6.96 (1H, dd, J=8.3 Hz, 2.7 Hz), 7.08 (1H, d, J=8.3 Hz), 7.62 (1H, d, J=2.7 Hz).

Reference Example 30

Preparation of 1-benzo[b]thiophen-4-yl-piperazine hydrochloride

A mixture of 14.4 g of 4-bromobenzo[b]thiophene, 29.8 g of piperazine anhydride, 9.3 g of sodium t-butoxide, 0.65 g of (R)-(+)-2,2'-bis(diphenylphosphino)-1,1'-binaphthyl (BINAP), 0.63 g of dipalladium tris(dibenzylideneacetone) and 250 ml of toluene was refluxed for 1 hour under nitrogen atmosphere. Water was poured to the reaction solution, which was then extracted with ethyl acetate and, after washed with water, dried over magnesium sulfate, and the solvent was evaporated under reduced pressure. The residue was purified by silica gel column chromatography (dichloromethane:methanol:25% ammonia water=100:10:1), and 9.5 g of 1-benzo[b]thiophen-4-yl-piperazine in the form of yellow oil was obtained.

3.7 ml of concentrated hydrochloric acid was added to a methanol solution of 9.5 g of 1-benzo[b]thiophen-4-yl-piperazine, and the solvent was evaporated under reduced pressure. Ethyl acetate was added to the residue and precipitated crystals were filtrated and recrystallized from methanol and 1-benzo[b]thiophen-4-yl-piperazine hydrochloride was obtained as colorless needle-like crystals.
Melting point 276-280° C.
¹H-NMR (DMSO-d₆) δ ppm:
3.25-3.35 (8H, m), 6.94 (1H, d, J=7.6 Hz), 7.30 (1H, dd, J=7.8 Hz, 7.8 Hz), 7.51 (1H, d, J=5.5 Hz), 7.68 (1H, d, J=8.1 Hz), 7.73 (1H, d, J=5.5 Hz), 9.35 (2H, brs).

Reference Example 31

Preparation of tert-butyl 4-benzo[b]thiophen-4-yl-3-methylpiperazin-1-carboxylate In the same manner as in Reference Example 30, tert-butyl 4-benzo[b]thiophen-4-yl-3-methylpiperazin-1-carboxylate was prepared from tert-butyl 3-methylpiperazin-1-carboxylate and 4-bromobenzo[b]thiophene.
¹H-NMR (CDCl₃) δ ppm:
1.85-1.95 (3H, m), 1.50 (9H, s), 2.8-2.9 (1H, m), 3.15-3.35 (2H, m), 3.4-3.5 (1H, m), 3.5-3.65 (1H, m), 3.65-3.7 (1H, m), 3.7-3.9 (1H, m), 6.98 (1H, d, J=7.5 Hz), 7.29 (1H, dd, J=8, 8 Hz), 7.38 (1H, d, J=5.5 Hz), 7.61 (1H, d, J=8 Hz).

Reference Example 32

Preparation of 1-benzo[b]thiophen-4-yl-2-methylpiperazine dihydrochloride

A solution of 1.22 g (3.7 mmol) of tert-butyl 4-benzo[b]thiophen-4-yl-3-methylpiperazin-1-carboxylate in methylene chloride (12 ml) was added to trifluoroacetic acid (6 ml), and the mixture was stirred at room temperature for 1 hour. The reaction mixture was concentrated under reduced pressure, then an aqueous solution of 5% potassium carbonate was added to the residue and the resulting mixture was extracted with methylene chloride. The organic phase was dried over magnesium sulfate and concentrated under reduced pressure. Concentrated hydrochloric acid (6 ml) and methanol (10 ml) were added to the residue and the resulting mixture was concentrated under reduced pressure. The residue was recrystallized from acetonitrile to obtain 1-benzo[b]thiophen-4-yl-2-methylpiperazine dihydrochloride (0.98 g) as light brown powder.

$^1$H-NMR (DMSO-$d_6$) δ ppm:
0.92 (3H, d, J=6.5 Hz), 2.8-3.6 (6H, m), 3.6-4.0 (1H, m), 5.3-6.8 (1H, m), 7.20 (1H, br), 7.38 (1H, dd, J=8, 8 Hz), 7.5-8.0 (3H, m), 9.4-10.1 (2H, m).

Reference Example 33

Preparation of 1-benzo[b]thiophen-4-yl-3-methylpiperazine dihydrochloride

In the same manner as in Reference Example 30, 1-benzo[b]thiophen-4-yl-3-methylpiperazine dihydrochloride was prepared from 2-methylpiperazine and 4-bromobenzo[b]thiophene.

$^1$H-NMR (DMSO-$d_6$) δ ppm:
1.34 (3H, d, J=6.5 Hz), 2.85-2.95 (1H, m), 3.05-3.15 (1H, m), 3.2-3.6 (6H, m), 6.97 (1H, d, J=7.5 Hz), 7.31 (1H, dd, J=8, 8 Hz), 7.54 (1H, d, J=5.5 Hz), 7.69 (1H, d, J=8 Hz), 7.75 (1H, d, J=5.5 Hz), 9.2-9.3 (1H, m), 9.64 (1H, br).

Reference Example 34

Preparation of ethyl 3-(4-benzo[b]thiophen-4-yl-piperazin-1-yl)propionate 5.05 g (19.8 mmol) of 1-Benzo[b]thiophen-4-yl-piperazine hydrochloride was added to an aqueous solution of sodium hydroxide, and the mixture was extracted with methylene chloride. The organic phase was dried over magnesium sulfate and concentrated under reduced pressure. The residue was dissolved in 50 ml of ethanol and ethyl acrylate (2.44 ml, 21.8 mmol) was added thereto, then the reaction mixture was refluxed for 4 hours. The reaction mixture was cooled to room temperature and concentrated under reduced pressure. Isopropyl ether was added to the residue to filter out insoluble matters. The insoluble matters were washed with isopropyl ether and dried to obtain ethyl 3-(4-benzo[b]thiophen-4-yl-piperazin-1-yl)propionate (5.26 g) as white powder.

Reference Example 35

Preparation of 3-(4-benzo[b]thiophen-4-yl-piperazine-1-yl)propan-1-ol

Lithium aluminum hydride (1.18 g, 24.8 mmol) was added to a solution of 5.26 g (16.5 mmol) of ethyl 3-(4-benzo[b]thiophen-4-yl-piperazin-1-yl)propionate in tetrahydrofuran (55 ml) with cooling in an ice-bath, followed by stirring at room temperature for 4 hours. Water (1.2 ml), 15% sodium hydroxide aqueous solution (1.2 ml), and water (3.6 ml) were added to the reaction mixture in this order with stirring at room temperature. Insoluble matters were removed by filtration, and the filtrate was concentrated under reduced pressure. The residue was purified by silica gel column chromatography (n-hexane:ethyl acetate=3:2→ethyl acetate), then concentrated and dried under reduced pressure to obtain 3-(4-benzo[b]thiophen-4-yl-piperazin-1-yl)propane-1-ol (0.23 g) as white powder.

$^1$H-NMR (CDCl$_3$) δ ppm:
1.75-1.85 (2H, m), 2.74 (2H, t, J=5.8 Hz), 2.75-2.85 (4H, m), 3.15-3.25 (4H, m), 3.85 (2H, t, J=5.3 Hz), 5.19 (1H, brs), 6.88 (1H, d, J=7.6 Hz), 7.27 (1H, dd, J=7.9, 7.8 Hz), 7.39 (2H, s), 7.56 (1H, d, J=8.0 Hz).

Reference Example 36

Preparation of 4-(4-benzo[b]thiophen-4-yl-piperazin-1-yl)butyl acetate 1.0 g (3.9 mmol) of 1-Benzo[b]thiophen-4-yl-piperazine hydrochloride was suspended in 20 ml of dimethylformamide (DMF), and potassium carbonate (1.3 g, 9.4 mmol) and 4-bromobutyl acetate (0.7 ml, 4.8 mmol) were added thereto followed by stirring at 80° C. for 6 hours. The reaction mixture was cooled to room temperature, then water was added thereto and the resulting mixture was extracted with ethyl acetate. The organic phase was washed with water, dried over magnesium sulfate, and concentrated under reduced pressure. The residue was purified by silica gel column chromatography (methylene chloride:methanol=30:1), then concentrated under reduced pressure to obtain 4-(4-benzo[b]thiophen-4-yl-piperazin-1-yl)butyl acetate (0.72 g) as light yellow oil.

Reference Example 37

Preparation of 4-(4-benzo[b]thiophen-4-yl-piperazin-1-yl)butan-1-ol

Potassium carbonate (3.87 g, 28 mmol) was added to a solution of 7.76 g (23.3 mmol) of butyl 4-(4-benzo[b]thiophen-4-yl-piperazin-1-yl) acetate in 90% methanol (150 ml) followed by stirring at room temperature for 2 hours. Water was added thereto and the reaction mixture was extracted with methylene chloride. The organic phase was dried over magnesium sulfate and concentrated under reduced pressure. The residue was purified by silica gel column chromatography (n-hexane:ethyl acetate=2:1→1:1), then concentrated under reduced pressure to obtain 4-(4-benzo[b]thiophen-4-yl-piperazin-1-yl)butane-1-ol (6.65 g) as colorless oil.

Reference Example 38

Preparation of 1-benzo[b]thiophen-4-yl-4-(3-chloropropyl)piperazine 3.56 g (12.9 mmol) of 3-(4-Benzo[b]thiophen-4-yl-piperazin-1-yl)propan-1-ol was suspended in 30 ml of methylene chloride, and carbon tetrachloride (30 ml) and triphenyl phosphine (4.06 g, 15.5 mmol) were added thereto followed by stirring under reflux for 3 hours. The reaction mixture was cooled to room temperature, then methanol and methylene chloride were added thereto so as to make the mixture uniform. Silica gel (30 g) was added to the uniform solution, and the solvent was evaporated under reduced pressure. The residue was purified by silica gel column chromatography (silica gel: 300 g, n-hexane:ethyl acetate=2:1), then concentrated under reduced pressure to obtain 1-benzo[b]thiophen-4-yl-4-(3-chloropropyl)piperazine (2.36 g) as colorless oil.

$^1$H-NMR (CDCl$_3$) δ ppm:

1.95-2.10 (2H, m), 2.60 (2H, t, J=7.2 Hz), 2.65-2.75 (4H, m), 3.15-3.25 (4H, m), 3.65 (2H, t, J=6.6 Hz), 6.89 (1H, dd, J=7.6, 0.7 Hz), 7.27 (1H, dd, J=7.9, 7.8 Hz), 7.38 (1H, d, J=5.6 Hz), 7.41 (1H, d, J=5.7 Hz), 7.55 (1H, d, J=8.0 Hz)

Example 1

Preparation of 7-[4-(4-benzo[b]thiophen-4-yl-piperazin-1-yl)butoxy]-1H-quinolin-2-one A mixture of 9.0 g of 7-(4-chlorobutoxy)-1H-quinolin-2-one, 10 g of 1-benzo[b]thiophene-4-yl-piperazine hydrochloride, 14 g of potassium carbonate, 6 g of sodium iodide and 90 ml of dimethylformamide was stirred for 2 hours at 80° C. Water was added to the reaction solution and precipitated crystals were separated by filtration. The crystals were dissolved in a mixed solvent of dichloromethane and methanol, dried over magnesium sulfate, and the solvent was evaporated under reduced pressure. The residue was purified by silica gel column chromatography (dichloromethane:methanol=100:3). Recrystallized from ethanol, 13.6 g of 7-[4-(4-benzo[b]thiophen-4-yl-piperazin-1-yl)butoxy]-1H-quinolin-2-one in the form of a white powder was obtained.

Melting point 183.5-184.5° C.

$^1$H-NMR (DMSO-d$_6$) δ ppm:

1.6-1.75 (2H, m), 1.75-1.9 (2H, m), 2.44 (2H, t, J=7 Hz), 2.5-2.8 (4H, m), 2.9-3.2 (4H, m), 4.06 (2H, t, J=6.5 Hz), 6.30 (1H, d, J=9.5 Hz), 6.75-6.85 (2H, m), 6.88 (1H, d, J=7.5 Hz), 7.27 (1H, dd, J=8 Hz, 8 Hz), 7.40 (1H, d, J=5.5 Hz), 7.55 (1H, d, J=9.5 Hz), 7.61 (1H, d, J=8 Hz), 7.69 (1H, d, J=5.5 Hz), 7.80 (1H, d, J=9.5 Hz), 11.59 (1H, bs).

Example 2

Preparation of 3-[2-(4-benzo[b]thiophen-4-yl-piperazin-1-yl)ethoxy]-1H-quinolin-2-one By a similar method as in Example 1, 3-[2-(4-benzo[b]thiophen-4-yl-piperazin-1-yl)ethoxy]-1H-quinolin-2-one was prepared from 3-(2-bromoethoxy)-1H-quinolin-2-one.

White powder (chloroform)

Melting point 201.9-204.5° C.

$^1$H-NMR (CDCl$_3$) δ ppm:

2.90-2.95 (4H, m), 3.10 (2H, t, J=5.9 Hz), 3.23-3.27 (4H, m), 4.30 (2H, t, J=5.9 Hz), 6.90 (1H, d, J=7.7 Hz), 7.08 (1H, s), 7.15-7.32 (2H, m), 7.37-7.41 (4H, m), 7.47-7.49 (1H, m), 7.55 (1H, d, J=8.1 Hz), 11.33 (1H, br).

Example 3

Preparation of 7-[3-(4-benzo[b]thiophen-4-yl-piperazin-1-yl)propoxy]-4-methyl-1H-quinolin-2-one By a similar method as in Example 1, 7-[3-(4-benzo[b]thiophen-4-yl-piperazin-1-yl)propoxy]-4-methyl-1H-quinolin-2-one was prepared from 7-(3-chloropropoxy)-4-methyl-1H-quinolin-2-one.

Slightly brown powder (ethyl acetate)

Melting point 202-208° C.

$^1$H-NMR (DMSO-d$_6$) δ ppm:

1.95-2.0 (2H, m), 2.37 (3H, s), 2.55 (2H, t, J=7 Hz), 2.6-2.7 (4H, m), 3.05-3.2 (4H, m), 4.09 (2H, t, J=6.5 Hz), 6.21 (1H, bs), 6.8-6.85 (2H, m), 6.90 (1H, d, J=7.5 Hz), 7.28 (1H, dd, J=8 Hz, 8 Hz), 7.41 (1H, d, J=5.5 Hz), 7.6-7.7 (2H, m), 7.69 (1H, d, J=5.5 Hz), 11.41 (1H, bs).

Example 4

Preparation of 7-[4-(4-benzo[b]thiophen-4-yl-piperazin-1-yl)butoxy]-4-methyl-1H-quinolin-2-one By a similar method as in Example 1, 7-[4-(4-benzo[b]thiophen-4-yl-piperazin-1-yl)butoxy]-4-methyl-1H-quinolin-2-one was prepared from 7-(4-chlorobutoxy)-4-methyl-1H-quinolin-2-one.

White powder (ethyl acetate)

Melting point 164-168° C.

$^1$H-NMR (DMSO-d$_6$) δppm:

1.6-1.7 (2H, m), 1.75-1.85 (2H, m), 2.37 (3H, s), 2.44 (2H, t, J=7 Hz), 2.55-2.7 (4H, m), 3.0-3.2 (4H, m), 4.0-4.15 (2H, m), 6.20 (1H, bs), 6.8-6.85 (2H, m), 6.88 (1H, d, J=7.5 Hz), 7.27 (1H, dd, J=8 Hz, 8 Hz), 7.40 (1H, d, J=5.5 Hz), 7.6-7.7 (2H, m), 7.69 (1H, d, J=5.5 Hz), 11.42 (1H, bs).

Example 5

Preparation of 7-[3-(4-benzo[b]thiophen-4-yl-piperazin-1-yl)propoxy]-3-methyl-1H-quinolin-2-one By a similar method as in Example 1, 7-[3-(4-benzo[b]thiophen-4-yl-piperazin-1-yl)propoxy]-3-methyl-1H-quinolin-2-one was prepared from 7-(3-chloropropoxy)-3-methyl-1H-quinolin-2-one.

White powder (ethyl acetate)

Melting point 185-187° C.

$^1$H-NMR (DMSO-d$_6$) δppm:

1.9-2.0 (2H, m), 2.04 (3H, s), 2.55 (2H, t, J=7 Hz), 2.6-2.75 (4H, m), 3.0-3.2 (4H, m), 4.07 (2H, t, J=6.5 Hz), 6.75-6.85 (2H, m), 6.90 (1H, d, J=7.5 Hz), 7.28 (1H, dd, J=8 Hz, 8 Hz), 7.40 (1H, d, J=5.5 Hz), 7.48 (1H, d, J=8.5 Hz), 7.61 (1H, d, J=8 Hz), 7.65-7.7 (2H, m), 11.57 (1H, bs).

Example 6

Preparation of 7-[4-(4-benzo[b]thiophen-4-yl-piperazin-1-yl)butoxy]-3-methyl-1H-quinolin-2-one By a similar method as in Example 1, 7-[4-(4-benzo[b]thiophen-4-yl-piperazin-1-yl)butoxy]-3-methyl-1H-quinolin-2-one was prepared from 7-(4-chlorobutoxy)-3-methyl-1H-quinolin-2-one.

White powder (ethyl acetate)

Melting point 197-199° C.

$^1$H-NMR (DMSO-d$_6$) δ ppm:

1.6-1.7 (2H, m), 1.75-1.9 (2H, m), 2.04 (3H, s), 2.44 (2H, t, J=7 Hz), 2.55-2.7 (4H, m), 3.0-3.15 (4H, m), 4.04 (2H, t, J=6.5 Hz), 6.75-6.85 (2H, m), 6.88 (1H, d, J=7.5 Hz), 7.27 (1H, dd, J=8 Hz, 8 Hz), 7.40 (1H, d, J=5.5 Hz), 7.47 (1H, d, J=8.5 Hz), 7.61 (1H, d, J=8 Hz), 7.65-7.75 (2H, m), 11.59 (1H, bs).

Example 7

Preparation of 7-[3-(4-benzo[b]thiophen-4-yl-piperazin-1-yl)propoxy]-1H-quinolin-2-one By a similar method as in Example 1, 7-[3-(4-benzo[b]thiophen-4-yl-piperazin-1-yl)propoxy]-1H-quinolin-2-one was prepared from 7-(3-chloropropoxy)-1H-quinolin-2-one.

White powder (ethyl acetate-diethyl ether)

Melting point 204-207° C.

¹H-NMR (DMSO-d₆) δ ppm:
1.97 (2H, t, J=6.8 Hz), 2.50-2.60 (2H, m), 2.60-2.65 (4H, m), 3.05-3.10 (4H, m), 4.08 (2H, t, J=6.4 Hz), 6.29 (1H, d, J=9.5 Hz), 6.75-6.85 (2H, m), 6.90 (1H, d, J=7.7 Hz), 7.25-7.30 (1H, m), 7.40 (1H, d, J=5.6 Hz), 7.55 (1H, d, J=8.4 Hz), 7.60-7.65 (1H, m), 7.69 (1H, d, J=5.5 Hz), 7.80 (1H, d, J=9.5 Hz), 11.57 (1H, s).

Example 8

Preparation of 1-[4-(4-benzo[b]thiophen-4-yl-piperazin-1-yl)butyl]-1H-quinolin-2-one hydrochloride By a similar method as in Example 1, 1-[4-(4-benzo[b]thiophen-4-yl-piperazin-1-yl)butyl]-1H-quinolin-2-one was prepared from 1-(4-chlorobutyl)-1H-quinolin-2-one, and after it was made into an ethanol solution, 1N hydrochloric acid ethanol solution was added thereto, precipitated crystals were separated by filtration, and thereby 1-[4-(4-benzo[b]thiophen-4-yl-piperazin-1-yl)butyl]-1H-quinolin-2-one hydrochloride was obtained in the form of a white powder.
Melting point 282.0° C. (decomposed)
¹H-NMR (DMSO-d₆) δ ppm:
1.60-2.00 (4H, m), 3.10-3.40 (6H, m), 3.50-3.60 (4H, m), 4.31 (2H, t, J=7.4 Hz), 6.63 (1H, d, J=9.4 Hz), 6.96 (1H, d, J=7.6 Hz), 7.24-7.35 (2H, m), 7.48 (1H, d, J=5.4 Hz), 7.59-7.78 (5H, m), 7.93 (1H, d, J=9.5 Hz), 10.00-10.20 (1H, m).

Example 9

Preparation of 1-[5-(4-benzo[b]thiophen-4-yl-piperazin-1-yl)pentyl]-1H-quinolin-2-one hydrochloride By a similar method as in Example 1, 1-[5-(4-benzo[b]thiophen-4-yl-piperazin-1-yl)pentyl]-1H-quinolin-2-one was prepared from 1-(5-chloropentyl)-1H-quinolin-2-one, and after it was made into an ethanol solution, 1N hydrochloric acid ethanol solution was added thereto, precipitated crystals were separated by filtration, and thereby 1-[5-(4-benzo[b]thiophen-4-yl-piperazin-1-yl)pentyl]-1H-quinolin-2-one hydrochloride was obtained in the form of a white powder.
Melting point 225.0-227.0° C.
¹H-NMR (DMSO-d₆) δppm:
1.35-1.50 (2H, m), 1.60-1.80 (4H, m), 3.10-3.30 (6H, m), 3.50-3.60 (4H, m), 4.27 (2H, t, J=7.4 Hz), 6.61 (1H, d, J=9.5 Hz), 6.96 (1H, d, J=7.5 Hz), 7.20-7.34 (2H, m), 7.47 (1H, d, J=5.5 Hz), 7.61-7.77 (5H, m), 7.91 (1H, d, J=9.5 Hz), 10.30-10.50 (1H, m).

Example 10

Preparation of 7-[3-(4-benzo[b]thiophen-4-yl-piperazin-1-yl)propoxy]-3,4-dihydro-1H-quinolin-2-one By a similar method as in Example 1, 7-[3-(4-benzo[b]thiophen-4-yl-piperazin-1-yl)propoxy]-3,4-dihydro-1H-quinolin-2-one was prepared from 7-(3-chloropropoxy)-3,4-dihydro-1H-quinolin-2-one.
White powder (methanol)
Melting point 163-165° C.
¹H-NMR (DMSO-d₆) δppm:
1.8-2.0 (2H, m), 2.41 (2H, t, J=7.5 Hz), 2.45-2.6 (2H, m), 2.6-2.7 (4H, m), 2.78 (2H, t, J=7.5 Hz), 2.95-3.2 (4H, m), 3.97 (2H, t, J=6.3 Hz), 6.46 (1H, d, J=2.3 Hz), 6.50 (1H, dd, J=2.4 Hz, 8.2 Hz), 6.90 (1H, d, J=7.6 Hz), 7.04 (1H, d, J=8.2 Hz), 7.27 (1H, dd, J=7.8 Hz, 7.8 Hz), 7.40 (1H, d, J=5.6 Hz), 7.61 (1H, d, J=8.0 Hz), 7.69 (1H, d, J=5.5 Hz), 9.97 (1H, bs).

Example 11

Preparation of 7-[4-(4-benzo[b]thiophen-4-yl-piperazin-1-yl)butoxy]-3,4-dihydro-1H-quinolin-2-one By a similar method as in Example 1, 7-[4-(4-benzo[b]thiophen-4-yl-piperazin-1-yl)butoxy]-3,4-dihydro-1H-quinolin-2-one was prepared from 7-(4-chlorobutoxy)-3,4-dihydro-1H-quinolin-2-one.
White powder (methanol)
Melting point 147-148° C.
¹H-NMR (DMSO-d₆) δppm:
1.55-1.65 (2H, m), 1.65-1.8 (2H, m), 2.35-2.5 (4H, m), 2.55-2.7 (4H, m), 2.78 (2H, t, J=7.5 Hz), 3.0-3.15 (4H, m), 3.93 (2H, t, J=6.4 Hz), 6.44 (1H, d, J=2.5 Hz), 6.49 (1H, dd, J=2.5 Hz, 8.3 Hz), 6.89 (1H, d, J=7.5 Hz), 7.04 (1H, d, J=8.3 Hz), 7.27 (1H, dd, J=7.8 Hz, 7.8 Hz), 7.35-7.45 (1H, m), 7.61 (1H, d, J=8.1 Hz), 7.68 (1H, d, J=5.6 Hz), 9.97 (1H, bs).

Example 12

Preparation of 7-[4-(4-benzo[b]thiophen-4-yl-piperazin-1-yl)butoxy]-3,4-dihydro-1H-quinolin-2-one hydrochloride 1N hydrochloric acid ethanol solution was added to an ethanol solution of 7-[4-(4-benzo[b]thiophen-4-yl-piperazin-1-yl)butoxy]-3,4-dihydro-1H-quinolin-2-one prepared in Example 11, and precipitated crystals were filtrated and recrystallized from 90% aqueous ethanol and 7-[4-(4-benzo[b]thiophen-4-yl-piperazin-1-yl)butoxy]-3,4-dihydro-1H-quinolin-2-one hydrochloride was obtained as slightly brown needle-like crystals.
Melting point 237-239° C.
¹H-NMR (DMSO-d₆) δ ppm:
1.75-1.85 (2H, m), 1.85-2.0 (2H, m), 2.42 (2H, t, J=7.5 Hz), 2.79 (2H, t, J=7.5 Hz), 3.15-3.5 (6H, m), 3.5-3.7 (4H, m), 3.96 (2H, t, J=6 Hz), 6.46 (1H, d, J=2.5 Hz), 6.5-6.55 (1H, m), 6.97 (1H, d, J=7.5 Hz), 7.07 (1H, d, J=8.5 Hz), 7.32 (1H, dd, J=8 Hz, 8 Hz), 7.50 (1H, d, J=5.5 Hz), 7.71 (1H, d, J=8 Hz), 7.77 (1H, d, J=5.5 Hz), 10.03 (1H, s), 10.65 (1H, br).

Example 13

Preparation of 7-[4-(4-benzo[b]thiophen-4-yl-piperazin-1-yl)-(Z)-2-butenyloxy]-3,4-dihydro-1H-quinolin-2-one By a similar method as in Example 1, 7-[4-(4-benzo[b]thiophen-4-yl-piperazin-1-yl)-(Z)-2-butenyloxy]-3,4-dihydro-1H-quinolin-2-one was prepared from 7-(4-chloro-(Z)-2-butenyloxy)-3,4-dihydro-1H-quinolin-2-one.
White powder (methanol)
Melting point 68-70° C.
¹H-NMR (DMSO-d₆) δppm:
2.42 (2H, t, J=7.5 Hz), 2.64 (4H, br), 2.79 (2H, t, J=7.5 Hz), 2.9-3.25 (6H, m), 4.61 (2H, d, J=3 Hz), 5.65-5.9 (2H, m), 6.48 (1H, d, J=2.5 Hz), 6.54 (1H, dd, J=2.5, 8.5 Hz), 6.89 (1H, d, J=7.5 Hz), 7.06 (1H, d, J=8.5 Hz), 7.27 (1H, dd, J=8 Hz, 8 Hz), 7.40 (1H, d, J=5.5 Hz), 7.61 (1H, d, J=8 Hz), 7.69 (1H, d, J=5.5 Hz), 10.01 (1H, bs).

Example 14

Preparation of 7-[4-(4-benzo[b]thiophen-4-yl-piperazin-1-yl)-3-methylbutoxy]-3,4-dihydro-1H-quinolin-2-one hydrochloride By a similar method as in Example 1, 7-[4-(4-benzo[b]thiophen-4-yl-piperazin-1-yl)-3-methylbutoxy]-3,4-dihydro-1H-quinolin-2-one was prepared from methanesulfonic acid 2-methyl-4-(2-oxo-1,2,3,4-tetrahydroquinolin-7-yloxy)butyl ester, and after it was made into a methanol solution, 0.5N hydrochloric acid methanol solution was added thereto, precipitated crystals were separated by filtration, recrystallized from isopropyl alcohol and thereby 7-[4-(4-benzo[b]thiophen-4-yl-piperazin-1-yl)-3-methylbutoxy]-3,4-dihydro-1H-quinolin-2-one hydrochloride was obtained in the form of a slightly yellow powder.

Melting point 217-219° C. (decomposed)
$^1$H-NMR DMSO-$d_6$) δppm:
1.12 (3H, d, J=6.5 Hz), 1.55-1.7 (1H, m), 1.9-2.05 (1H, m), 2.2-2.3 (1H, m), 2.41 (2H, t, J=7.5 Hz), 2.79 (2H, t, J=7.5 Hz), 3.05-3.15 (1H, m), 3.15-3.25 (1H, m), 3.25-3.45 (4H, m), 3.45-3.55 (2H, m), 3.55-3.7 (2H, m), 3.9-4.1 (2H, m), 6.49 (1H, d, J=2.5 HZ), 6.54 (1H, dd, J=2.5 Hz, 8.5 Hz), 6.97 (1H, d, J=7.5 Hz), 7.06 (1H, d, J=8.5 Hz), 7.33 (1H, dd, J=8 Hz, 8 Hz), 7.49 (1H, d, J=5.5 Hz), 7.70 (1H, d, J=8 Hz), 7.77 (1H, d, J=5.5 Hz), 10.03 (1H, bs), 10.66 (1H, br).

Example 15

Preparation of 7-[4-(4-benzo[b]thiophen-4-yl-piperazin-1-yl)-(E)-2-butenyloxy]-3,4-dihydro-1H-quinolin-2-one By a similar method as in Example 1, 7-[4-(4-benzo[b]thiophen-4-yl-piperazin-1-yl)-(E)-2-butenyloxy]-3,4-dihydro-1H-quinolin-2-one was prepared from 7-(4-bromo-(E)-2-butenyloxy)-3,4-dihydro-1H-quinolin-2-one.

White powder (dichloromethane-diisopropyl ether)
Melting point 147.8-149.7° C.
$^1$H-NMR (CDCl$_3$) δppm:
2.61 (2H, t, J=7.5 Hz), 2.65-2.75 (4H, m), 2.90 (2H, t, J=7.5 Hz), 3.1-3.2 (6H, m), 4.52 (2H, d, J=4.3 Hz), 5.9-6.0 (2H, m), 6.31 (1H, d, J=2.3 Hz), 6.55 (1H, dd, J=8.3 Hz, 2.3 Hz), 6.90 (1H, d, J=7.6 Hz), 7.05 (1H, d, J=8.3 Hz), 7.27 (1H, m), 7.37-7.41 (2H, m), 7.53-7.60 (2H, m).

Example 16

Preparation of 7-[4-(4-benzo[b]thiophen-4-yl-piperazin-1-yl)butoxy]-4-methyl-3,4-dihydro-1H-quinolin-2-one By a similar method as in Example 1, 7-[4-(4-benzo[b]thiophen-4-yl-piperazin-1-yl)butoxy]-4-methyl-3,4-dihydro-1H-quinolin-2-one was prepared from 7-(4-chlorobutoxy)-4-methyl-3,4-dihydro-1H-quinolin-2-one.

White powder (methanol)
Melting point 112-115° C.
$^1$H-NMR (DMSO-$d_6$) δppm:
1.14 (3H, d, J=7 Hz), 1.55-1.7 (2H, m), 1.7-1.8 (2H, m), 2.19 (1H, dd, J=7, 16 Hz), 2.43 (2H, t, J=7 Hz), 2.5-2.7 (5H, m), 2.9-3.0 (1H, m), 3.0-3.1 (4H, m), 3.94 (2H, t, J=6.5 Hz), 6.45 (1H, d, J=2.5 Hz), 6.53 (1H, dd, J=2.5, 8.5 Hz), 6.89 (1H, d, J=7.5 Hz), 7.07 (1H, d, J=8.5 Hz), 7.27 (1H, dd, J=8 Hz, 8 Hz), 7.39 (1H, d, J=5.5 Hz), 7.61 (1H, d, J=8 Hz), 7.69 (1H, d, J=5.5 Hz), 9.98 (1H, bs).

Example 17

Preparation of 7-{2-[2-(4-benzo[b]thiophen-4-yl-piperazin-1-yl)ethoxy]ethoxy}-3,4-dihydro-1H-quinolin-2-one dihydrochloride By a similar method as in Example 1, 7-{2-[2-(4-benzo[b]thiophen-4-yl-piperazin-1-yl)ethoxy]ethoxy}-3,4-dihydro-1H-quinolin-2-one was prepared from 7-[2-(2-chloroethoxy)ethoxy]-3,4-dihydro-1H-quinolin-2-one, and after it was made into an ethanol solution, 1N hydrochloric acid ethanol solution was added thereto, precipitated crystals were separated by filtration, recrystallized from isopropyl alcohol-diisopropyl ether and thereby 7-{2-[2-(4-benzo[b]thiophen-4-yl-piperazin-1-yl)ethoxy]ethoxy}-3,4-dihydro-1H-quinolin-2-one dihydrochloride was obtained in the form of a white powder.

Melting point 172.3-177.2° C.
$^1$H-NMR (CDCl$_3$) δppm:
2.53 (2H, t, J=7.5 Hz), 2.80 (2H, t, J=7.5 Hz), 3.40 (2H, m), 3.54-3.59 (2H, m), 3.79-3.94 (6H, m), 4.16-4.30 (6H, m), 6.50-6.53 (2H, m), 7.01 (1H, d, J=8.0 Hz), 7.36 (1H, dd, J=8 Hz, 8 Hz), 7.53-7.62 (2H, m), 7.82 (1H, d, J=8.0 Hz), 7.91 (1H, m), 8.02 (1H, brs), 13.31 (1H, brs).

Example 18

Preparation of 7-[4-(4-benzo[b]thiophen-4-yl-piperazin-1-yl)butoxy]-1-methyl-3,4-dihydro-1H-quinolin-2-one hydrochloride 48 mg of sodium hydride (60% oily) was added to a solution of 0.40 g of 7-[4-(4-benzo[b]thiophen-4-yl-piperazin-1-yl)butoxy]-3,4-dihydro-1H-quinolin-2-one in dimethylformamide (5 ml) and tetrahydrofuran (5 ml) while being stirred under ice-cooling and stirred at room temperature for 1 hour, and after that 0.07 ml of methyl iodide was added and stirred at room temperature for 1 hour. Water was added to the reaction solution, which was then extracted with ethyl acetate and, after washed with water, dried over magnesium sulfate, and the solvent was evaporated under reduced pressure. The residue was purified by silica gel column chromatography (dichloromethane:methanol=30:1). The solvent was evaporated under reduced pressure and 0.5N hydrochloric acid ethanol solution was added thereto, precipitated crystals were separated by filtration, and thereby 0.15 g of 7-[4-(4-benzo[b]thiophen-4-yl-piperazin-1-yl)butoxy]-1-methyl-3,4-dihydro-1H-quinolin-2-one hydrochloride was obtained in the form of a slightly yellow powder.

Melting point 275.6-277.6° C.
$^1$H-NMR (DMSO-$d_6$) δ ppm:
1.70-1.94 (4H, m), 2.48-2.52 (2H, m), 2.77 (2H, t, J=7.2 Hz), 3.15-3.30 (9H, m), 3.52-3.63 (4H, m), 4.03 (2H, t, J=6.0 Hz), 6.58-6.63 (2H, m), 6.96 (1H, d, J=7.5 Hz), 7.11 (1H, d, J=8.1 Hz), 7.31 (1H, dd, J=7.8 Hz, 7.8 Hz), 7.48 (1H, d, J=5.5 Hz), 7.69 (1H, d, J=8.0 Hz), 7.75 (1H, d, J=5.5 Hz), 10.61 (1H, br).

Example 19

Preparation of 6-[3-(4-benzo[b]thiophen-4-yl-piperazin-1-yl)propoxy]-3,4-dihydro-1H-quinolin-2-one hydrochloride By a similar method as in Example 1, 6-[3-(4-benzo[b]thiophen-4-yl-piperazin-1-yl)propoxy]-3,4-dihydro-1H-quinolin-2-one was prepared from 6-(3-chloropropoxy)-3,4-dihydro-1H-quinolin-2-one, and after it was made into a methanol solution, 0.5N hydrochloric acid methanol solution was added thereto, precipitated crystals were separated by filtration, recrystallized from a mixed solvent of ethyl acetate-diethyl ether and thereby 6-[3-(4-benzo[b]thiophen-4-yl-piperazin-1-yl)propoxy]-3,4-dihydro-1H-quinolin-2-one hydrochloride was obtained in the form of a white powder.

Melting point 231-234° C.

$^1$H-NMR (DMSO-$d_6$) δppm:

2.20-2.30 (2H, m), 2.35-2.45 (2H, m), 2.83 (2H, t, J=7.5 Hz), 3.20-3.70 (10H, m), 4.02 (2H, t, J=5.9 Hz), 6.70-6.85 (3H, m), 6.96 (1H, d, J=7.6 Hz), 7.31 (1H, dd, J=7.9 Hz, 7.9 Hz), 7.48 (1H, d, J=5.6 Hz), 7.69 (1H, d, J=8.1 Hz), 7.76 (1H, d, J=5.5 Hz), 9.93 (1H, brs), 10.90 (1H, brs).

Example 20

Preparation of 6-[4-(4-benzo[b]thiophen-4-yl-piperazin-1-yl)butoxy]-3,4-dihydro-1H-quinolin-2-one By a similar method as in Example 1, 6-[4-(4-benzo[b]thiophen-4-yl-piperazin-1-yl)butoxy]-3,4-dihydro-1H-quinolin-2-one was prepared from 6-(4-bromobutoxy)-3,4-dihydro-1H-quinolin-2-one.

White powder (ethyl acetate-diethyl ether)

Melting point 175-178° C.

$^1$H-NMR (CDCl$_3$) δppm:

1.65-1.90 (4H, m), 2.52 (2H, t, J=7.3 Hz), 2.55-2.65 (2H, m), 2.65-2.75 (4H, m), 2.94 (2H, t, J=7.5 Hz), 3.15-3.25 (4H, m), 3.90-4.00 (2H, m), 6.65-6.75 (3H, m), 6.89 (1H, dd, J=0.7 Hz, 7.6 Hz), 7.27 (1H, dd, J=7.9 Hz, 7.9 Hz), 7.35-7.45 (2H, m), 7.55 (1H, d, J=8.0 Hz), 8.02 (1H, brs).

Example 21

Preparation of 1-[4-(4-benzo[b]thiophen-4-yl-piperazin-1-yl)butyl]-3,4-dihydro-1H-quinolin-2-one hydrochloride By a similar method as in Example 1, 1-[4-(4-benzo[b]thiophen-4-yl-piperazin-1-yl)butyl]-3,4-dihydro-1H-quinolin-2-one was prepared from 1-(4-chlorobutyl)-3,4-dihydro-1H-quinolin-2-one, and after it was made into an ethanol solution, 1N hydrochloric acid ethanol solution was added thereto, precipitated crystals were separated by filtration and thereby 1-[4-(4-benzo[b]thiophen-4-yl-piperazin-1-yl)butyl]-3,4-dihydro-1H-quinolin-2-one hydrochloride was obtained in the form of a white powder.

Melting point 257.0-259.0° C.

$^1$H-NMR (DMSO-$d_6$) δppm:

1.60-1.80 (4H, m), 2.54 (2H, t, J=8.3 Hz), 2.87 (2H, t, J=7.9 Hz), 3.10-3.30 (6H, m), 3.50-3.60 (4H, m), 3.95 (2H, t, J=7.0 Hz), 6.94-7.04 (2H, m), 7.14-7.35 (4H, m), 7.48 (1H, d, J=5.6 Hz), 7.70 (1H, d, J=8.0 Hz), 7.76 (1H, d, J=5.6 Hz), 10.00-10.20 (1H, m).

Example 22

Preparation of 1-[5-(4-benzo[b]thiophen-4-yl-piperazin-1-yl)pentyl]-3,4-dihydro-1H-quinolin-2-one hydrochloride By a similar method as in Example 1, 1-[5-(4-benzo[b]thiophen-4-yl-piperazin-1-yl)pentyl]-3,4-dihydro-1H-quinolin-2-one was prepared from 1-(5-chloropentyl)-3,4-dihydro-1H-quinolin-2-one, and after it was made into an ethanol solution, 1N hydrochloric acid ethanol solution was added thereto, precipitated crystals were separated by filtration and thereby 1-[5-(4-benzo[b]thiophen-4-yl-piperazin-1-yl)pentyl]-3,4-dihydro-1H-quinolin-2-one hydrochloride was obtained.

Melting point 242.0-244.0° C.

$^1$H-NMR (DMSO-$d_6$) δppm:

1.30-1.45 (2H, m), 1.50-1.65 (2H, m), 1.70-1.85 (2H, m), 2.53 (2H, t, J=8.2 Hz), 2.85 (2H, t, J=8.0 Hz), 3.10-3.30 (6H, m), 3.50-3.60 (4H, m), 3.91 (2H, t, J=7.3 Hz), 6.94-7.03 (2H, m), 7.13-7.34 (4H, m), 7.47 (1H, d, J=5.6 Hz), 7.69 (1H, d, J=8.0 Hz), 7.76 (1H, d, J=5.5 Hz), 10.30-10.50 (1H, m).

Example 23

Preparation of 2-[4-(4-benzo[b]thiophen-4-yl-piperazin-1-yl)butyl]-3,4-dihydro-2H-isoquinolin-1-one hydrochloride By a similar method as in Example 1, 2-[4-(4-benzo[b]thiophen-4-yl-piperazin-1-yl)butyl]-3,4-dihydro-2H-isoquinolin-1-one was prepared from 2-(4-chlorobutyl)-3,4-dihydro-2H-isoquinolin-1-one, and after it was made into an ethanol solution, 1N hydrochloric acid ethanol solution was added thereto, precipitated crystals were separated by filtration, recrystallized from a mixed solvent of isopropyl alcohol-ethanol and thereby 2-[4-(4-benzo[b]thiophen-4-yl-piperazin-1-yl)butyl]-3,4-dihydro-2H-isoquinolin-1-one hydrochloride was obtained.

Melting point 257.5-265.5° C.

$^1$H-NMR (DMSO-$d_6$) δppm:

1.6-1.9 (4H, m), 2.98-3.60 (16H, m), 6.98 (1H, d, J=7.7 Hz), 7.30-7.38 (3H, m), 7.46-7.51 (2H, m), 7.71 (1H, d, J=8.2 Hz), 7.77 (1H, d, J=5.5 Hz), 7.89 (1H, d, J=7.7 Hz), 10.10 (1H, brs).

Example 24

Preparation of 2-[5-(4-benzo[b]thiophen-4-yl-piperazin-1-yl)pentyl]-3,4-dihydro-2H-isoquinolin-1-one By a similar method as in Example 1, 2-[5-(4-benzo[b]thiophen-4-yl-piperazin-1-yl)pentyl]-3,4-dihydro-2H-isoquinolin-1-one was prepared from 2-(5-chloropentyl)-3,4-dihydro-2H-isoquinolin-1-one.

White powder (ethyl acetate-diisopropyl ether)

Melting point 91.8-93.3° C.

$^1$H-NMR (CDCl$_3$) δppm:

1.32-1.37 (2H, m), 1.56-1.64 (4H, m), 2.38 (2H, t, J=7.6 Hz), 2.62 (4H, m), 2.92 (2H, t, J=6.5 Hz), 3.09-3.11 (4H, m), 3.47-3.55 (4H, m), 6.81 (1H, d, J=7.5 Hz), 7.08-7.11 (2H, m), 7.17-7.35 (4H, m), 7.47 (1H, d, J=8.0 Hz), 8.01 (1H, dd, J=7.5 Hz, 1.4 Hz).

Example 25

Preparation of 6-[3-(4-benzo[b]thiophen-4-yl-piperazin-1-yl)propoxy]-3,4-dihydro-2H-isoquinolin-1-one By a similar method as in Example 1, 6-[3-(4-benzo[b]thiophen-4-yl-piperazin-1-yl)propoxy]-3,4-dihydro-2H-isoquinolin-1-one was prepared from 6-(3-chloropropoxy)-3,4-dihydro-2H-isoquinolin-1-one.

White powder (ethyl acetate-diethyl ether)

Melting point 203-205° C.

¹H-NMR (CDCl₃) δppm:
2.00-2.10 (2H, m), 2.60-2.70 (2H, m), 2.74 (4H, brs), 2.96 (2H, t, J=6.5 Hz), 3.20 (4H, brs), 3.50-3.60 (2H, m), 4.11 (2H, t, J=6.3 Hz), 6.09 (1H, brs), 6.73 (1H, s), 6.85-6.95 (2H, m), 7.25-7.30 (1H, m), 7.35-7.45 (2H, m), 7.55 (1H, d, J=8.1 Hz), 8.01 (1H, d, J=8.6 Hz).

Example 26

Preparation of 6-[3-(4-benzo[b]thiophen-4-yl-piperazin-1-yl)propoxy]-2-methyl-3,4-dihydro-2H-isoquinolin-1-one By a similar method as in Example 18, 6-[3-(4-benzo[b]thiophen-4-yl-piperazin-1-yl)propoxy]-2-methyl-3,4-dihydro-2H-isoquinolin-1-one was prepared from 6-[3-(4-benzo[b]thiophen-4-yl-piperazin-1-yl)propoxy]-3,4-dihydro-2H-isoquinolin-1-one using methyl iodide.
White powder (ethyl acetate-diethyl ether) Melting point 110-113° C.
¹H-NMR (CDCl₃) δppm:
2.05 (2H, t, J=6.9 Hz), 2.65 (2H, t, J=7.3 Hz), 2.74 (4H, brs), 2.97 (2H, t, J=6.7 Hz), 3.14 (3H, s), 3.21 (4H, brs), 3.54 (2H, t, J=6.7 Hz), 4.11 (2H, t, J=6.4 Hz), 6.68 (1H, s), 6.86 (1H, dd, J=2.3 Hz, 8.6 Hz), 6.91 (1H, d, J=7.7 Hz), 7.25-7.30 (1H, m), 7.40 (1H, d, J=5.5 Hz), 7.42 (1H, d, J=5.5 Hz), 7.56 (1H, d, J=7.9 Hz), 8.03 (1H, d, J=8.6 Hz).

Example 27

Preparation of 6-[3-(4-benzo[b]thiophen-4-yl-piperazin-1-yl)propoxy]-2-ethyl-3,4-dihydro-2H-isoquinolin-1-one By a similar method as in Example 18, 6-[3-(4-benzo[b]thiophen-4-yl-piperazin-1-yl)propoxy]-2-ethyl-3,4-dihydro-2H-isoquinolin-1-one was prepared from 6-[3-(4-benzo[b]thiophen-4-yl-piperazin-1-yl)propoxy]-3,4-dihydro-2H-isoquinolin-1-one using ethyl iodide.
White powder (ethyl acetate-diethyl ether)
Melting point 128-131° C.
¹H-NMR (CDCl₃) δppm:
1.21 (3H, t, J=7.2 Hz), 2.05 (2H, t, J=6.9 Hz), 2.65 (2H, t, J=7.3 Hz), 2.74 (4H, brs), 2.96 (2H, t, J=6.6 Hz), 3.21 (4H, brs), 3.54 (2H, t, J=6.7 Hz), 3.62 (2H, q, J=7.2 Hz), 4.11 (2H, t, J=6.3 Hz), 6.68 (1H, d, J=1.7 Hz), 6.86 (1H, dd, J=2.3 Hz, 8.2 Hz), 6.91 (1H, d, J=7.7 Hz), 7.25-7.30 (1H, m), 7.40 (1H, d, J=5.5 Hz), 7.42 (1H, d, J=5.5 Hz), 7.56 (1H, d, J=7.8 Hz), 8.03 (1H, d, J=8.6 Hz).

Example 28

Preparation of 7-[3-(4-benzo[b]thiophen-4-yl-piperazin-1-yl)propoxy]-3,4-dihydro-2H-isoquinolin-1-one By a similar method as in Example 1, 7-[3-(4-benzo[b]thiophen-4-yl-piperazin-1-yl)propoxy]-3,4-dihydro-2H-isoquinolin-1-one was prepared from 7-(3-chloropropoxy)-3,4-dihydro-2H-isoquinolin-1-one.
White powder (ethyl acetate-diethyl ether)
Melting point 176-179° C.
¹H-NMR (CDCl₃) δppm:
2.00-2.10 (2H, m), 2.64 (2H, t, J=7.3 Hz), 2.73 (4H, brs), 2.94 (2H, t, J=6.6 Hz), 3.20 (4H, brs), 3.50-3.60 (2H, m), 4.12 (2H, t, J=6.3 Hz), 5.92 (1H, brs), 6.90 (1H, d, J=7.7 Hz), 7.03 (1H, dd, J=2.8 Hz, 8.3 Hz), 7.13 (1H, d, J=8.3 Hz), 7.25-7.30 (1H, m), 7.39 (1H, d, J=5.5 Hz), 7.42 (1H, d, J=5.5 Hz), 7.55 (1H, d, J=8.1 Hz), 7.62 (1H, d, J=2.7 Hz).

Example 29

Preparation of 7-[3-(4-benzo[b]thiophen-4-yl-piperazin-1-yl)propoxy]-2-methyl-3,4-dihydro-2H-isoquinolin-1-one By a similar method as in Example 18, 7-[3-(4-benzo[b]thiophen-4-yl-piperazin-1-yl)propoxy]-2-methyl-3,4-dihydro-2H-isoquinolin-1-one was prepared from 7-[3-(4-benzo[b]thiophen-4-yl-piperazin-1-yl)propoxy]-3,4-dihydro-2H-isoquinolin-1-one using methyl iodide.
White powder (ethanol)
Melting point 115-117° C.
¹H-NMR (CDCl₃) δppm:
1.95-2.10 (2H, m), 2.64 (2H, t, J=7.3 Hz), 2.70-2.80 (4H, m), 2.94 (2H, t, J=6.7 Hz), 3.10-3.25 (4H, m), 3.16 (3H, s), 2.54 (2H, t, J=6.7 Hz), 4.11 (2H, t, J=6.5 Hz), 6.90 (1H, d, J=7.0 Hz), 6.98 (1H, dd, J=2.7 Hz, 8.3 Hz), 7.08 (1H, d, J=8.3 Hz), 7.28 (1H, dd, J=7.9 Hz, 7.9 Hz), 7.35-7.45 (2H, m), 7.55 (1H, d, J=8.1 Hz), 7.63 (1H, d, J=2.6 Hz).

Example 30

Preparation of 7-[3-(4-benzo[b]thiophen-4-yl-piperazin-1-yl)propoxy]-2-methyl-3,4-dihydro-2H-isoquinolin-1-one hydrochloride After 7-[3-(4-benzo[b]thiophen-4-yl-piperazin-1-yl)propoxy]-2-methyl-3,4-dihydro-2H-isoquinolin-1-one was made into an ethanol solution, 1N hydrochloric acid ethanol solution was added thereto, precipitated crystals were separated by filtration, recrystallized from ethanol and thereby 7-[3-(4-benzo[b]thiophen-4-yl-piperazin-1-yl)propoxy]-2-methyl-3,4-dihydro-2H-isoquinolin-1-one hydrochloride was obtained in the form of a white powder.
Melting point 229-233° C.
¹H-NMR (DMSO-d₆) δppm:
2.20-2.30 (2H, m), 2.89 (2H, t, J=6.7 Hz), 3.01 (3H, s), 3.21 (2H, t, J=6.9 Hz), 3.30-3.60 (8H, m), 3.60-3.70 (2H, m), 4.11 (2H, t, J=6.0 Hz), 6.97 (1H, d, J=7.7 Hz), 7.06 (1H, dd, J=2.8 Hz, 8.3 Hz), 7.22 (1H, d, J=7.9 Hz), 7.31 (1H, dd, J=7.8 Hz, 7.8 Hz), 7.41 (1H, d, J=2.7 Hz), 7.49 (1H, d, J=5.5 Hz), 7.69 (1H, d, J=8.1 Hz), 7.76 (1H, d, J=5.5 Hz), 10.70 (1H, brs).

Example 31

Preparation of 7-[3-(4-benzo[b]thiophen-4-yl-piperazin-1-yl)propoxy]-2-ethyl-3,4-dihydro-2H-isoquinolin-1-one dihydrochloride By a similar method as in Example 18, 7-[3-(4-benzo[b]thiophen-4-yl-piperazin-1-yl)propoxy]-2-ethyl-3,4-dihydro-2H-isoquinolin-1-one was prepared from 7-[3-(4-benzo[b]thiophen-4-yl-piperazin-1-yl)propoxy]-3,4-dihydro-2H-isoquinolin-1-one using ethyl iodide, and after it was made into a methanol solution, 0.5N hydrochloric acid methanol solution was added thereto, precipitated crystals were separated by filtration, recrystallized from a mixed solvent of methanol-ethyl acetate and thereby 7-[3-(4-benzo[b]thiophen-4-yl-piperazin-1-yl)propoxy]-2-ethyl-3,4-dihydro-2H-isoquinolin-1-one dihydrochloride was obtained in the form of a white powder.

Melting point 210-213° C.
¹H-NMR (DMSO-d$_6$) δ ppm:
1.09 (3H, t, J=7.1 Hz), 2.20-2.30 (2H, m), 2.87 (2H, t, J=6.5 Hz), 3.20-3.70 (14H, m), 4.11 (2H, t, J=5.9 Hz), 6.96 (1H, d, J=7.7 Hz), 7.00-7.10 (1H, m), 7.22 (1H, d, J=8.3 Hz), 7.25-7.35 (1H, m), 7.41 (1H, d, J=2.7 Hz), 7.48 (1H, d, J=5.5 Hz), 7.69 (1H, d, J=7.7 Hz), 7.76 (1H, d, J=5.5 Hz), 11.08 (1H, brs).

Example 32

Preparation of 7-[4-(4-benzo[b]thiophen-4-yl-piperazin-1-yl)butoxy]-2-methyl-3,4-dihydro-2H-isoquinolin-1-one hydrochloride By a similar method as in Example 1, 7-[4-(4-benzo[b]thiophen-4-yl-piperazin-1-yl)butoxy]-2-methyl-3,4-dihydro-2H-isoquinolin-1-one was prepared from 7-(4-chlorobutoxy)-2-methyl-3,4-dihydro-2H-isoquinolin-1-one, and after it was made into a methanol solution, 0.5N hydrochloric acid methanol solution was added thereto, precipitated crystals were separated by filtration, recrystallized from a mixed solvent of methanol-ethyl acetate and thereby 7-[4-(4-benzo[b]thiophen-4-yl-piperazin-1-yl)butoxy]-2-methyl-3,4-dihydro-2H-isoquinolin-1-one hydrochloride was obtained in the form of a white powder.
Melting point 213-218° C.
¹H-NMR (DMSO-d$_6$) δppm:
1.70-2.00 (4H, m), 2.88 (2H, t, J=6.6 Hz), 3.01 (3H, s), 3.10-3.70 (12H, m), 4.03 (2H, t, J=5.8 Hz), 6.95 (1H, d, J=7.5 Hz), 7.04 (1H, dd, J=2.8 Hz, 8.5 Hz), 7.20 (1H, d, J=8.4 Hz), 7.31 (1H, dd, J=7.8 Hz, 7.8 Hz), 7.39 (1H, d, J=2.7 Hz), 7.48 (1H, d, J=5.7 Hz), 7.69 (1H, d, J=8.1 Hz), 7.75 (1H, d, J=5.5 Hz), 10.71 (1H, brs).

Example 33

Preparation of 7-[4-(4-benzo[b]thiophen-4-yl-piperazin-1-yl)butoxy]-3,4-dihydro-2H-isoquinolin-1-one hydrochloride By a similar method as in Example 1, 7-[4-(4-benzo[b]thiophen-4-yl-piperazin-1-yl)butoxy]-3,4-dihydro-2H-isoquinolin-1-one was prepared from 7-(4-chlorobutoxy)-3,4-dihydro-2H-isoquinolin-1-one, and after it was made into an ethyl acetate solution, 1N hydrochloric acid ethanol solution was added thereto, precipitated crystals were separated by filtration, recrystallized from ethyl acetate and thereby 7-[4-(4-benzo[b]thiophen-4-yl-piperazin-1-yl)butoxy]-3,4-dihydro-2H-isoquinolin-1-one hydrochloride was obtained in the form of a white powder.
Melting point 223.8-226.8° C.
¹H-NMR (DMSO-d$_6$) δppm:
1.81-1.93 (4H, m), 2.83 (2H, t, J=6.5 Hz), 3.16-3.32 (8H, m), 3.43-3.64 (4H, m), 4.06 (2H, t, J=5.9 Hz), 6.97 (1H, d, J=7.6 Hz), 7.07 (1H, dd, J=8.3 Hz, 2.7 Hz), 7.24 (1H, d, J=7.7 Hz), 7.32 (1H, dd, J=7.9 Hz, 7.9 Hz), 7.39 (1H, d, J=2.7 Hz), 7.50 (1H, d, J=5.6 Hz), 7.71 (1H, d, J=8.0 Hz), 7.77 (1H, d, J=5.5 Hz), 7.95 (1H, s), 10.62 (1H, s).

Example 34

Preparation of 2-[4-(4-benzo[b]thiophen-4-yl-piperazin-1-yl)butyl]-2H-isoquinolin-1-one By a similar method as in Example 1, 2-[4-(4-benzo[b]thiophen-4-yl-piperazin-1-yl)butyl]-2H-isoquinolin-1-one was prepared from 2-(4-chlorobutyl)-2H-isoquinolin-1-one.

Pale brown powder (ethyl acetate-diisopropyl ether)
Melting point 141.1-142.7° C.
¹H-NMR (CDCl$_3$) δppm:
1.62 (2H, m), 1.87 (2H, m), 2.50 (2H, t, J=7.4 Hz), 2.66-2.71 (4H, m), 3.16-3.19 (4H, m), 4.06 (2H, t, J=7.2 Hz), 6.50 (1H, d, J=7.3 Hz), 6.89 (1H, d, J=7.7 Hz), 7.08 (1H, d, J=7.3 Hz), 7.24-7.65 (7H, m), 8.44 (1H, d, J=7.9 Hz).

Example 35

Preparation of 7-[3-(4-benzo[b]thiophen-4-yl-piperazin-1-yl)propoxy]-2H-isoquinolin-1-one By a similar method as in Example 1, 7-[3-(4-benzo[b]thiophen-4-yl-piperazin-1-yl)propoxy]-2H-isoquinolin-1-one was prepared from 7-(3-chloropropoxy)-2H-isoquinolin-1-one.
White powder (ethyl acetate)
Melting point 220.1-222.5° C.
¹H-NMR (DMSO-d$_6$) δppm:
1.99 (2H, quint, J=6.6 Hz), 2.57 (2H, t, J=7.0 Hz), 2.66 (4H, brs), 3.09 (4H, brs), 4.16 (2H, t, J=6.3 Hz), 6.52 (1H, d, J=7.1 Hz), 6.90 (1H, d, J=7.4 Hz), 7.04 (1H, dd, J=6.9 Hz, 6.9 Hz), 7.26 (1H, d, J=7.9 Hz), 7.33 (1H, dd, J=8.8 Hz, 2.8 Hz), 7.41 (1H, d, J=5.5 Hz), 7.59-7.63 (3H, m), 7.69 (1H, d, J=5.5 Hz), 11.21 (1H, d, J=4.9 Hz).

Example 36

Preparation of 7-[3-(4-benzo[b]thiophen-4-yl-piperazin-1-yl)propoxy]-2-methyl-2H-isoquinolin-1-one hydrochloride By a similar method as in Example 18, 7-[3-(4-benzo[b]thiophen-4-yl-piperazin-1-yl)propoxy]-2-methyl-2H-isoquinolin-1-one was prepared from 7-[3-(4-benzo[b]thiophen-4-yl-piperazin-1-yl)propoxy]-2H-isoquinolin-1-one using methyl iodide, and after it was made into an ethyl acetate solution, 1N hydrochloric acid ethanol solution was added thereto, precipitated crystals were separated by filtration, recrystallized from ethyl acetate and thereby 7-[3-(4-benzo[b]thiophen-4-yl-piperazin-1-yl)propoxy]-2-methyl-2H-isoquinolin-1-one hydrochloride was obtained in the form of a white powder.
Melting point 227.6-230.2° C.
¹H-NMR (DMSO-d$_6$) δppm:
2.31 (2H, quint, J=7.0 Hz), 3.20-3.40 (6H, m), 3.52 (3H, s), 3.54-3.70 (4H, m), 4.23 (2H, t, J=5.8 Hz), 6.60 (1H, d, J=7.3 Hz), 6.99 (1H, d, J=7.7 Hz), 7.30-7.38 (3H, m), 7.51 (1H, d, J=5.6 Hz), 7.63-7.73 (3H, m), 7.78 (1H, d, J=5.5 Hz), 10.88 (1H, s).

Example 37

Preparation of 7-[3-(4-benzo[b]thiophen-4-yl-piperazin-1-yl)propoxy]-2-ethyl-2H-isoquinolin-1-one hydrochloride By a similar method as in Example 1, 7-[3-(4-benzo[b]thiophen-4-yl-piperazin-1-yl)propoxy]-2-ethyl-2H-isoquinolin-1-one was prepared from 7-(3-chloropropoxy)-2-ethyl-2H-isoquinolin-1-one, and after it was made into an ethyl acetate solution, 1N hydrochloric acid ethanol solution was added thereto, precipitated crystals were separated by filtration, recrystallized from ethyl acetate and thereby 7-[3-

(4-benzo[b]thiophen-4-yl-piperazin-1-yl)propoxy]-2-ethyl-2H-isoquinolin-1-one hydrochloride was obtained in the form of a white powder.

Melting point 229.9-231.2° C.
$^1$H-NMR (DMSO-d$_6$) δppm:
1.25 (3H, t, J=7.1 Hz), 2.29 (2H, brs), 3.14-3.49 (6H, m), 3.56-3.72 (4H, m), 4.00 (2H, q, J=7.2 Hz), 4.23 (2H, t, J=5.9 Hz), 6.62 (1H, d, J=7.3 Hz), 6.99 (1H, d, J=7.6 Hz), 7.27-7.39 (3H, m), 7.51 (1H, d, J=5.6 Hz), 7.62-7.73 (3H, m), 7.78 (1H, d, J=5.5 Hz), 10.38 (1H, s).

Example 38

Preparation of 2-[4-(4-benzo[b]thiophen-4-yl-piperazin-1-yl)butyl]-7-methoxy-2H-isoquinolin-1-one hydrochloride By a similar method as in Example 1, 2-[4-(4-benzo[b]thiophen-4-yl-piperazin-1-yl)butyl]-7-methoxy-2H-isoquinolin-1-one was prepared from 2-(4-chlorobutyl)-7-methoxy-2H-isoquinolin-1-one, and after it was made into an ethyl acetate solution, 1N hydrochloric acid ethanol solution was added thereto, precipitated crystals were separated by filtration, recrystallized from ethyl acetate and thereby 2-[4-(4-benzo[b]thiophen-4-yl-piperazin-1-yl)butyl]-7-methoxy-2H-isoquinolin-1-one hydrochloride was obtained in the form of a white powder.

Melting point 243.5-245.6° C.
$^1$H-NMR (DMSO-d$_6$) δppm:
1.78 (4H, brs), 3.10-3.28 (6H, m), 3.56 (4H, t, J=9.6 Hz), 3.87 (3H, s), 4.04 (2H, t, J=5.3 Hz), 6.64 (1H, d, J=7.3 Hz), 6.96 (1H, d, J=7.6 Hz), 7.30 (1H, d, J=8.0 Hz), 7.34 (1H, dd, J=8.6 Hz, 2.9 Hz), 7.41 (1H, d, J=7.3 Hz), 7.49 (1H, d, J=5.6 Hz), 7.63 (1H, d, J=8.6 Hz), 7.69 (1H, dd, J=8.0 Hz, 8.0 Hz), 7.77 (1H, d, J=5.5 Hz), 10.60 (1H, s).

Example 39

Preparation of 2-[4-(4-benzo[b]thiophen-4-yl-piperazin-1-yl)butyl]-7-hydroxy-2H-isoquinolin-1-one hydrobromide Boron tribromide (2M dichloromethane solution, 1.0 ml) was added to a dichloromethane (50 ml) solution of 2-[4-(4-benzo[b]thiophen-4-yl-piperazin-1-yl)butyl]-7-methoxy-2H-isoquinolin-1-one (0.16 g) while being stirred under ice-cooling and stirred at room temperature for 3 days. Water was added to the reaction solution, which was then stirred at room temperature for 0.5 hour. Precipitated crystals were separated by filtration, recrystallized from ethyl acetate and thereby 2-[4-(4-benzo[b]thiophen-4-yl-piperazin-1-yl)butyl]-7-hydroxy-2H-isoquinolin-1-one hydrobromide (0.13 g) was obtained in the form of a white powder.

Melting point 273.6-275.7° C.
$^1$H-NMR (DMSO-d$_5$) δppm:
1.75 (4H, brs), 3.08 (2H, t, J=11.1 Hz), 3.16-3.28 (4H, m), 3.59 (2H, t, J=10.5 Hz), 4.01 (2H, brs), 6.58 (1H, d, J=7.3 Hz), 6.97 (1H, d, J=7.5 Hz), 7.19 (1H, dd, J=8.6 Hz, 2.6 Hz), 7.29-7.36 (2H, m), 7.49-7.65 (3H, m), 7.71 (1H, d, J=8.0 Hz), 7.78 (1H, d, J=5.5 Hz), 9.50 (1H, brs), 9.95 (1H, s)..

Example 40

Preparation of 6-[3-(4-benzo[b]thiophen-4-yl-piperazin-1-yl)propoxy]-2H-isoquinolin-1-one By a similar method as in Example 1, 6-[3-(4-benzo[b]thiophen-4-yl-piperazin-1-yl)propoxy]-2H-isoquinolin-1-one was prepared from 6-chloropropoxy-2H-isoquinolin-1-one.

White powder (ethyl acetate)
Melting point 228.8-230.7° C.
$^1$H-NMR (DMSO-d$_6$) δppm:
1.98 (2H, quint, J=6.7 Hz), 2.56 (2H, t, J=7.0 Hz), 2.65 (4H, brs), 3.09 (4H, brs), 4.17 (2H, t, J=6.3 Hz), 6.47 (1H, d, J=7.1 Hz), 6.90 (1H, d, J=7.6 Hz), 7.05 (1H, dd, J=8.8 Hz, 2.4 Hz), 7.10-7.15 (2H, m), 7.28 (1H, d, J=7.8 Hz), 7.41 (1H, d, J=5.5 Hz), 7.62 (1H, d, J=8.0 Hz), 7.70 (1H, d, J=5.5 Hz), 8.07 (1H, d, J=8.8 Hz), 11.03 (1H, s).

Example 41

Preparation of 6-[3-(4-benzo[b]thiophen-4-yl-piperazin-1-yl)propoxy]-2-methyl-2H-isoquinolin-1-one hydrochloride By a similar method as in Example 18, 6-[3-(4-benzo[b]thiophen-4-yl-piperazin-1-yl)propoxy]-2-methyl-2H-isoquinolin-1-one was prepared from 6-[3-(4-benzo[b]thiophen-4-yl-piperazin-1-yl)propoxy]-2H-isoquinolin-1-one using methyl iodide, and after it was made into an ethyl acetate solution, 1N hydrochloric acid ethanol solution was added thereto, precipitated crystals were separated by filtration, recrystallized from ethyl acetate and thereby 6-[3-(4-benzo[b]thiophen-4-yl-piperazin-1-yl)propoxy]-2-methyl-2H-isoquinolin-1-one hydrochloride was obtained in the form of a white powder.

Melting point 241.4-244.8° C.
$^1$H-NMR (DMSO-d$_6$) δppm:
2.31 (2H, t, J=7.6 Hz), 3.46 (3H, s), 3.19-3.70 (10H, m), 4.24 (2H, t, J=5.9 Hz), 6.54 (1H, d, J=7.4 Hz), 6.99 (1H, d, J=7.6 Hz), 7.10 (1H, dd, J=8.8 Hz, 2.4 Hz), 7.15 (1H, d, J=2.3 Hz), 7.33 (1H, dd, J=7.9 Hz, 7.9 Hz), 7.45 (1H, d, J=7.1 Hz), 7.51 (1H, d, J=5.5 Hz), 7.71 (1H, d, J=8.0 Hz), 7.78 (1H, d, J=5.5 Hz), 8.14 (1H, d, J=8.8 Hz), 10.86 (1H, s).

Example 42

Preparation of 7-[4-(4-benzo[b]thiophen-4-yl-piperazin-1-yl)butoxy]-1H-quinolin-2-one hydrochloride 1N hydrochloric acid aqueous solution was added to a solution of 7-[4-(4-benzo[b]thiophen-4-yl-piperazin-1-yl)butoxy]-1H-quinolin-2-one in methanol and dichloromethane and the solvent was evaporated under reduced pressure. The residue was recrystallized from 70% ethanol and thereby 7-[4-(4-benzo[b]thiophen-4-yl-piperazin-1-yl)butoxy]-1H-quinolin-2-one hydrochloride was obtained in the form of a white powder.

Melting point 238-241° C.
$^1$H-NMR (DMSO-d$_6$) δ ppm:
1.80-2.00 (4H, m), 3.20-3.45 (6H, m), 3.50-3.60 (4H, m), 4.06 (2H, t, J=5.6 Hz), 6.28 (1H, d, J=9.5 Hz), 6.75-6.85 (2H, m), 6.95 (1H, d, J=7.5 Hz), 7.30 (1H, dd, J=7.8 Hz, 7.8 Hz), 7.47 (1H, d, J=5.7 Hz), 7.56 (1H, d, J=8.4 Hz), 7.68 (1H, d, J=8.1 Hz), 7.70-7.85 (2H, m), 10.92 (1H, brs), 11.61 (1H, brs).

Example 43

Preparation of 7-[4-(4-benzo[b]thiophen-4-yl-piperazin-1-yl)butoxy]-1H-quinolin-2-one sulfate Dilute sulphuric acid was added to a solution of 7-[4-(4-benzo[b]thiophen-4-yl-piperazin-1-yl)butoxy]-1H-quinolin-2-one in methanol and dichloromethane and the solvent was evaporated under reduced pressure. The residue was recrystallized from 60% ethanol and thereby 7-[4-(4-benzo[b]thiophen-4-yl-piperazin-1-yl)butoxy]-1H-quinolin-2-one sulfate was obtained in the form of a white powder.

Melting point 248-251° C.

$^1$H-NMR (DMSO-$d_6$) δppm:

1.80-1.95 (4H, m), 2.50-4.00 (10H, m), 4.00-4.10 (2H, m), 6.30 (1H, d, J=8.2 Hz), 6.75-6.85 (2H, m), 6.97 (1H, d, J=7.6 Hz), 7.31 (1H, dd, J=7.8 Hz, 7.8 Hz), 7.49 (1H, d, J=5.6 Hz), 7.55-7.60 (1H, m), 7.70 (1H, d, J=8.0 Hz), 7.75-7.85 (2H, m), 9.25-9.75 (1H, br), 11.62 (1H, brs).

Example 44

Preparation of 7-[4-(4-benzo[b]thiophen-4-yl-piperazin-1-yl)butoxy]-1H-quinolin-2-one maleate A methanol solution of maleic acid was added to a solution of 7-[4-(4-benzo[b]thiophen-4-yl-piperazin-1-yl)butoxy]-1H-quinolin-2-one in methanol and dichloromethane and the solvent was evaporated under reduced pressure. The residue was recrystallized from 80% ethanol and thereby 7-[4-(4-benzo[b]thiophen-4-yl-piperazin-1-yl)butoxy]-1H-quinolin-2-one maleate was obtained in the form of a white powder.

Melting point 181.6-182.8° C.

$^1$H-NMR (DMSO-$d_6$) δ ppm:

1.87 (2H, brs), 3.26-3.47 (10H, m), 4.10 (2H, s), 6.07 (2H, s), 6.33 (1H, d, J=9.5 Hz), 6.82-6.84 (2H, m), 6.99 (1H, d, J=7.6 Hz), 7.33 (1H, d, J=7.8 Hz), 7.51 (1H, d, J=5.5 Hz), 7.59 (1H, d, J=9.3 Hz), 7.70-7.85 (3H, m), 11.65 (1H, s).

Example 45

Preparation of 7-[4-(4-benzo[b]thiophen-4-yl-piperazin-1-yl)butoxy]-1H-quinolin-2-one fumarate Fumaric acid was added to a solution of 7-[4-(4-benzo[b]thiophen-4-yl-piperazin-1-yl)butoxy]-1H-quinolin-2-one in methanol and dichloromethane and the solvent was evaporated under reduced pressure. The residue was recrystallized from ethanol and thereby 7-[4-(4-benzo[b]thiophen-4-yl-piperazin-1-yl)butoxy]-1H-quinolin-2-one fumarate was obtained in the form of a white powder.

Melting point 209-211° C.

$^1$H-NMR (DMSO-$d_6$) δppm:

1.60-1.90 (4H, m), 2.47-2.50 (2H, m), 2.60-2.75 (4H, m), 3.00-3.15 (4H, m), 4.05 (2H, t, J=6.3 Hz), 6.28 (1H, d, J=9.4 Hz), 6.60 (2H, s), 6.76-6.82 (2H, m), 6.88 (1H, d, J=7.4 Hz), 7.26 (1H, dd, J=7.9 Hz, 7.8 Hz), 7.39 (1H, d, J=5.9 Hz), 7.54 (1H, d, J=9.4 Hz), 7.61 (1H, d, J=8.0 Hz), 7.69 (1H, d, J=5.5 Hz), 7.79 (1H, d, J=9.5 Hz), 11.58 (1H, brs).

Example 46

Preparation of 7-[4-(4-benzo[b]thiophen-4-yl-piperazin-1-yl)butoxy]-1H-quinolin-2-one citrate Citric acid was added to a solution of 7-[4-(4-benzo[b]thiophen-4-yl-piperazin-1-yl)butoxy]-1H-quinolin-2-one in methanol and dichloromethane and the solvent was evaporated under reduced pressure. The residue was recrystallized from 50% ethanol and thereby 7-[4-(4-benzo[b]thiophen-4-yl-piperazin-1-yl)butoxy]-1H-quinolin-2-one citrate was obtained in the form of a white powder.

Melting point 183-185° C.

$^1$H-NMR (DMSO-$d_6$) δ ppm:

1.50-2.00 (4H, m), 2.58 (2H, s), 2.62 (2H, s), 2.75-2.85 (2H, m), 2.95-3.05 (4H, m), 3.10-3.20 (4H, m), 4.05 (2H, t, J=5.3 Hz), 6.28 (1H, d, J=9.4 Hz), 6.75-6.85 (2H, m), 6.90 (1H, d, J=7.6 Hz), 7.27 (1H, dd, J=7.9 Hz, 7.9 Hz), 7.42 (1H, d, J=5.5 Hz), 7.55 (1H, d, J=9.3 Hz), 7.64 (1H, d, J=8.0 Hz), 7.71 (1H, d, J=5.5 Hz), 7.79 (1H, d, J=9.5 Hz), 11.59 (1H, brs).

Example 47

Preparation of 7-[4-(4-benzo[b]thiophen-4-yl-piperazin-1-yl)butoxy]-1H-quinolin-2-one p-toluenesulfonate p-Toluenesulfonic acid monohydrate was added to a solution of 7-[4-(4-benzo[b]thiophen-4-yl-piperazin-1-yl)butoxy]-1H-quinolin-2-one in methanol and dichloromethane and the solvent was evaporated under reduced pressure. The residue was recrystallized from methanol and thereby 7-[4-(4-benzo[b]thiophen-4-yl-piperazin-1-yl)butoxy]-1H-quinolin-2-one p-toluenesulfonate was obtained in the form of a white powder.

Melting point 121.0-125.0° C.

$^1$H-NMR (DMSO-$d_6$) δ ppm:

1.73-2.00 (4H, m), 2.28 (3H, s), 3.07 (2H, J=11.0 Hz), 3.23-3.43 (4H, m), 3.62 (4H, t, J=15.0 Hz), 4.09 (2H, t, J=7.1 Hz), 6.31 (1H, dd, J=9.5 Hz, 2.3 Hz), 6.80 (1H, Si, 6.84 (1H, d, J=2.3 Hz), 6.98 (1H, d, J=7.5 Hz), 7.11 (2H, d, J=8.0 Hz), 7.33 (1H, dd, J=7.5 Hz, 7.5 Hz), 7.46-7.52 (3H, m), 7.58 (1H, d, J=9.5 Hz), 7.72 (1H, d, J=7.5 Hz), 7.78 (1H, d, J=11.3 Hz), 7.81 (1H, d, J=9.5 Hz), 9.31-9.49 (1H, m), 11.54-11.63 (1H, m).

Example 48

Preparation of 7-[3-(4-benzo[b]thiophen-4-yl-piperazin-1-yl)propoxy]-2-methyl-3,4-dihydro-2H-isoquinolin-1-one sulfate Dilute sulphuric acid was added to a solution of 7-[3-(4-benzo[b]thiophen-4-yl-piperazin-1-yl)propoxy]-2-methyl-3,4-dihydro-2H-isoquinolin-1-one in ethanol and dichloromethane and the solvent was evaporated under reduced pressure. The residue was recrystallized from 85% ethanol and thereby 7-[3-(4-benzo[b]thiophen-4-yl-piperazin-1-yl)propoxy]-2-methyl-3,4-dihydro-2H-isoquinolin-1-one sulfate was obtained in the form of a white powder.

Melting point 222-224° C.

$^1$H-NMR (DMSO-$d_6$) δppm:

2.10-2.30 (2H, m), 2.91 (2H, t, J=6.6 Hz), 3.03 (3H, s), 3.05-4.00 (12H, m), 4.13 (2H, t, J=5.9 Hz), 6.99 (1H, d, J=7.5 Hz), 7.09 (1H, dd, J=2.7 Hz, 8.3 Hz), 7.24 (1H, d, J=8.4 Hz), 7.33 (1H, dd, J=7.8 Hz, 7.8 Hz), 7.44 (1H, d, J=2.7 Hz), 7.51 (1H, d, J=5.5 Hz), 7.72 (1H, d, J=8.1 Hz), 7.78 (1H, d, J=5.5 Hz), 9.00-10.05 (1H, br).

Example 49

Preparation of 7-[3-(4-benzo[b]thiophen-4-yl-piperazin-1-yl)propoxy]-2-methyl-3,4-dihydro-2H-isoquinolin-1-one fumarate Fumaric acid was added to an ethanol solution of 7-[3-(4-benzo[b]thiophen-4-yl-piperazin-1-yl)propoxy]-2-methyl-3,4-dihydro-2H-isoquinolin-1-one and the solvent was evaporated under reduced pressure. The residue was recrystallized from 70% ethanol and thereby 7-[3-(4-benzo

[b]thiophen-4-yl-piperazin-1-yl)propoxy]-2-methyl-3,4-dihydro-2H-isoquinolin-1-one fumarate was obtained in the form of a pale yellow powder.

Melting point 149-151° C.

$^1$H-NMR (DMSO-d$_6$) δppm:

1.85-2.00 (2H, m), 2.58 (2H, t, J=7.2 Hz), 2.65-2.75 (4H, m), 2.88 (2H, t, J=6.7 Hz), 3.01 (3H, s), 3.05-3.15 (4H, m), 3.50 (2H, t, J=6.7 Hz), 4.05 (2H, t, J=6.3 Hz), 6.60 (2H, s), 6.89 (1H, d, J=7.6 Hz), 7.03 (1H, dd, J=8.3 Hz, 2.7 Hz), 7.19 (1H, d, J=8.3 Hz), 7.27 (1H, dd, J=7.9 Hz, 7.8 Hz), 7.38 (1H, d, J=3.0 Hz), 7.40 (1H, d, J=5.9 Hz), 7.61 (1H, d, J=8.0 Hz), 7.69 (1H, d, J=5.5 Hz).

Example 50

Preparation of 7-[3-(4-benzo[b]thiophen-4-yl-piperazin-1-yl)propoxy]-2-methyl-3,4-dihydro-2H-isoquinolin-1-one difumarate Fumaric acid was added to an ethanol solution of 7-[3-(4-benzo[b]thiophen-4-yl-piperazin-1-yl)propoxy]-2-methyl-3,4-dihydro-2H-isoquinolin-1-one and the solvent was evaporated under reduced pressure. The residue was recrystallized from 90% ethanol and thereby 7-[3-(4-benzo[b]thiophen-4-yl-piperazin-1-yl)propoxy]-2-methyl-3,4-dihydro-2H-isoquinolin-1-one difumarate was obtained in the form of white prism crystal.

Melting point 188-189° C.

$^1$H-NMR (DMSO-d$_6$) δppm:

1.85-2.00 (2H, m), 2.60 (2H, t, J=7.0 Hz), 2.65-2.75 (4H, m), 2.88 (2H, t, J=6.6 Hz), 3.01 (3H, s), 3.00-3.10 (4H, m), 3.50 (2H, t, J=6.7 Hz), 4.05 (2H, t, J=6.4 Hz), 6.61 (4H, s), 6.90 (1H, d, J=7.5 Hz), 7.04 (1H, dd, J=8.2 Hz, 2.8 Hz), 7.19 (1H, d, J=8.4 Hz), 7.27 (1H, dd, J=7.9 Hz, 7.8 Hz), 7.38 (1H, d, J=3.0 Hz), 7.40 (1H, d, J=6.2 Hz), 7.61 (1H, d, J=8.0 Hz), 7.69 (1H, d, J=5.5 Hz).

Example 51

Preparation of 7-[3-(4-benzo[b]thiophen-4-yl-piperazin-1-yl)propoxy]-2-methyl-3,4-dihydro-2H-isoquinolin-1-one maleate A methanol solution of maleic acid was added to a solution of 7-[3-(4-benzo[b]thiophen-4-yl-piperazin-1-yl)propoxy]-2-methyl-3,4-dihydro-2H-isoquinolin-1-one in methanol and dichloromethane and the solvent was evaporated under reduced pressure. The residue was recrystallized from ethanol and ethyl acetate and thereby 7-[3-(4-benzo[b]thiophen-4-yl-piperazin-1-yl)propoxy]-2-methyl-3,4-dihydro-2H-isoquinolin-1-one maleate was obtained in the form of a white powder.

Melting point 134.6-135.5° C.

$^1$H-NMR (DMSO-d$_6$) δppm:

2.17 (2H, brs), 2.91 (2H, t, J=6.7 Hz), 3.03 (3H, s), 3.33 (10H, brs), 3.52 (2H, t, J=6.7 Hz), 4.12 (2H, t, J=5.9 Hz), 6.04 (2H, s), 6.99 (1H, d, J=7.6 Hz), 7.07 (1H, dd, J=8.3 Hz, 2.6 Hz), 7.24 (1H, d, J=8.4 Hz), 7.32 (1H, dd, J=7.9 Hz, 7.9 Hz), 7.43 (1H, d, J=2.6 Hz), 7.50 (1H, d, J=5.5 Hz), 7.71 (1H, d, J=7.9 Hz), 7.77 (1H, d, J=5.5 Hz).

Example 52

Preparation of 7-[3-(4-benzo[b]thiophen-4-yl-piperazin-1-yl)propoxy]-2-methyl-3,4-dihydro-2H-isoquinolin-1-one p-toluenesulfonate p-Toluenesulfonic acid monohydrate was added to a solution of 7-[3-(4-benzo[b]thiophen-4-yl-piperazin-1-yl)propoxy]-2-methyl-3,4-dihydro-2H-isoquinolin-1-one in methanol and dichloromethane and the solvent was evaporated under reduced pressure. The residue was recrystallized from ethanol and ethyl acetate and thereby 7-[3-(4-benzo[b]thiophen-4-yl-piperazin-1-yl)propoxy]-2-methyl-3,4-dihydro-2H-isoquinolin-1-one p-toluenesulfonate was obtained in the form of a white powder.

Melting point 173.0-175.5° C.

$^1$H-NMR (DMSO-d$_6$) δppm:

2.00-2.33 (2H, m), 2.28 (3H, s), 2.91 (2H, t, J=6.6 Hz), 3.02 (3H, s), 3.00-3.16 (2H, m), 3.29-3.80 (10H, m), 4.12 (2H, t, J=5.5 Hz), 6.99 (1H, d, J=7.9 Hz), 7.06 (1H, d, J=2.5 Hz), 7.11 (2H, d, J=7.9 Hz), 7.24 (1H, d, J=8.0 Hz), 7.33 (1H, dd, J=8.0 Hz, 8.0 Hz), 7.44 (1H, d, J=2.5 Hz), 7.48 (1H, d, J=7.9 Hz), 7.51 (1H, d, J=5.5 Hz), 7.72 (1H, d, J=8.0 Hz), 7.82 (1H, d, J=5.5 Hz), 9.39-9.58 (1H, m)

Example 53

Preparation of 7-[3-(4-benzo[b]thiophen-4-yl-piperazin-1-yl)propoxy]-2-methyl-3,4-dihydro-2H-isoquinolin-1-one By a similar method as in Example 1, 7-[3-(4-benzo[b]thiophen-4-yl-piperazin-1-yl)propoxy]-2-methyl-3,4-dihydro-2H-isoquinolin-1-one was prepared from 7-(3-chloropropoxy)-2-methyl-3,4-dihydro-2H-isoquinolin-1-one.

White powder (ethanol)

Melting point 115-117° C.

$^1$H-NMR (CDCl$_3$) δppm:

1.95-2.10 (2H, m), 2.64 (2H, t, J=7.3 Hz), 2.70-2.80 (4H, m), 2.94 (2H, t, J=6.7 Hz), 3.10-3.25 (4H, m), 3.16 (3H, s), 2.54 (2H, t, J=6.7 Hz), 4.11 (2H, t, J=6.5 Hz), 6.90 (1H, d, J=7.0 Hz), 6.98 (1H, dd, J=2.7 Hz, 8.3 Hz), 7.08 (1H, d, J=8.3 Hz), 7.28 (1H, dd, J=7.9 Hz, 7.9 Hz), 7.35-7.45 (2H, m), 7.55 (1H, d, J=8.1 Hz), 7.63 (1H, d, J=2.6 Hz).

Example 54

Preparation of 7-[3-(4-benzo[b]thiophen-4-yl-piperazin-1-yl)propoxy]-2-methyl-3,4-dihydro-2H-isoquinolin-1-one methanesulfonate Methanesulfonic acid was added to an ethanol solution of 7-[3-(4-benzo[b]thiophen-4-yl-piperazin-1-yl)propoxy]-2-methyl-3,4-dihydro-2H-isoquinolin-1-one and the solvent was evaporated under reduced pressure. The residue was recrystallized from 80% ethanol and thereby 7-[3-(4-benzo[b]thiophen-4-yl-piperazin-1-yl)propoxy]-2-methyl-3,4-dihydro-2H-isoquinolin-1-one methanesulfonate was obtained in the form of pale yellow prism crystal.

Melting point 147-149° C.

$^1$H-NMR (DMSO-d$_6$) δppm:

2.10-2.25 (2H, m), 2.29 (3H, s), 2.90 (2H, t, J=6.7 Hz), 3.02 (3H, s), 3.05-3.15 (2H, m), 3.40-3.50 (4H, m), 3.51 (2H, t, J=6.7 Hz), 3.55-3.70 (4H, m), 4.12 (2H, t, J=6.0 Hz), 6.98 (1H, d, J=7.6 Hz), 7.06 (1H, dd, J=8.3 Hz, 2.7 Hz), 7.23 (1H, d, J=8.4 Hz), 7.32 (1H, dd, J=7.9 Hz, 7.8 Hz), 7.43 (1H, d, J=2.7 Hz), 7.50 (1H, d, J=5.5 Hz), 7.71 (1H, d, J=8.1 Hz), 7.77 (1H, d, J=5.5 Hz), 9.40-9.60 (1H, m).

Example 55

Preparation of 4-[3-(4-benzo[b]thiophen-4-yl-piperazin-1-yl)propoxy]quinoline hydrochloride 4-Chloroquinoline (230 mg, 1.58 mmol), 3-(4-benzo[b]thiophen-4-yl-piperazin-1-yl)propan-1-ol (310 mg, 1.05 mmol), and potassium carbonate (220 mg, 1.6 mmol) were added to dimethylformamide (10 ml), followed by stirring at 80° C. for 5 hours. The reaction mixture was cooled to room temperature, then water was added thereto and the reaction mixture was extracted with ethyl acetate. The organic phase was washed with water, dried over magnesium sulfate, and concentrated under reduced pressure after filtration. The residue was purified by basic silica gel column chromatography (n-hexane:ethyl acetate=4:1), and concentrated under reduced pressure. The resulting residue was dissolved in ethanol (3 ml), and 1N-HCl—ethanol solution (1 ml) was added thereto. Insoluble matters produced were filtered out and dried to obtain 4-[3-(4-benzo[b]thiophen-4-yl-piperazin-1-yl)propoxy]quinoline hydrochloride (360 mg, yield: 78%) as light yellow powder.

Melting point: 240-242° C.

Example 56

Preparation of 3-[3-(4-benzo[b]thiophen-4-yl-piperazin-1-yl)propoxy]isoquinoline hydrochloride 3-Hydroxyisoquinoline (170 mg, 1.17 mmol), 1-benzo[b]thiophen-4-yl-4-(3-chloropropyl)piperazine (290 mg, 1.0 mmol), and potassium carbonate (200 mg, 1.45 mmol) were added to dimethylformamide (8 ml), followed by stirring at 80° C. for 7 hours. The reaction mixture was cooled to room temperature, then water was added thereto and the reaction mixture was extracted with ethyl acetate. The organic phase was washed with water, dried over magnesium sulfate, and concentrated under reduced pressure after filtration. The residue was purified by basic silica gel column chromatography (n-hexane:ethyl acetate=9:1), and concentrated under reduced pressure. The resulting residue was dissolved in ethanol (2 ml), and 1N-HCl—ethanol solution (0.5 ml) was added thereto. Insoluble matters produced were filtered out and dried to obtain 3-[3-(4-benzo[b]thiophen-4-yl-piperazin-1-yl)propoxy]isoquinoline hydrochloride (160 mg, yield: 37%) as white powder.

Melting point: 227-229° C.

Example 57

Preparation of 7-[3-(4-benzo[b]thiophen-4-yl-piperazin-1-yl)propoxy]-6-methoxy-3,4-dihydroisoquinoline dihydrochloride PS-triphenylphosphine (110 mg, 3 mmol/g) and dibenzyl azodicarboxylate (70 mg, 0.3 mmol) were added to a solution of 7-hydroxy-6-methoxy-3,4-dihydroisoquinoline (80 mg, 0.45 mmol) and 3-(4-benzo[b]thiophen-4-yl-piperazin-1-yl)propan-1-ol (83 mg, 0.3 mmol) in tetrahydrofuran (1 ml), followed by stirring at 50° C. for 3 hours. The reaction mixture was cooled to room temperature and insoluble matters were removed by filtration. The filtrate was concentrated under reduced pressure. The residue was purified by basic silica gel column chromatography (n-hexane:ethyl acetate=1:1), and concentrated under reduced pressure. The resulting residue was dissolved in 2-propanol, and 1N-HCl—ethanol solution was added thereto. Isopropyl ether was further added thereto, then crystals precipitated were filtered out and dried to obtain 7-[3-(4-benzo[b]thiophen-4-yl-piperazin-1-yl)propoxy]-6-methoxy-3,4-dihydroisoquinoline dihydrochloride (26 mg, yield: 17%) as light yellow powder.

Melting point: 211.0-213.0° C.

Example 58

Preparation of 1-acetyl-7-[3-(4-benzo[b]thiophen-4-yl-piperazin-1-yl)propoxy]-1,2,3,4-tetrahydroquinoline hydrochloride Acetic anhydride (0.34 ml, 3.6 mmol) and pyridine (0.34 ml, 4.3 mmol) were added to a solution of 7-[3-(4-benzo[b]thiophen-4-yl-piperazin-1-yl)propoxy]-1,2,3,4-tetrahydroquinoline (0.49 g, 1.2 mmol) in methylene chloride (10 ml) with cooling in an ice-bath, followed by stirring at room temperature overnight. The reaction mixture was concentrated under reduced pressure, and water and ethyl acetate were added to the residue to separate the organic phase from the water phase. The organic phase was washed with water, saturated sodium hydrogencarbonate aqueous solution and brine in this order, and concentrated under reduced pressure. The residue was purified by basic silica gel column chromatography (n-hexane:ethyl acetate=1:1), and concentrated under reduced pressure. The resulting residue was dissolved in ethyl acetate (10 ml), and 1N-HCl—ethanol solution was added thereto. Then, crystals precipitated were filtered out and dried to obtain 1-acetyl-7-[3-(4-benzo[b]thiophen-4-yl-piperazin-1-yl)propoxy]-1,2,3,4-tetrahydroquinoline hydrochloride (0.27 g, yield: 52%) as white powder.

Melting point: 123.2-124.3° C.

Example 59

Preparation of 6-[3-(4-benzo[b]thiophen-4-yl-piperazin-1-yl)propoxy]-1,2,3,4-tetrahydroquinoline hydrochloride Lithium aluminum hydride (160 mg, 4.2 mmol) was added to a solution of 6-[3-(4-benzo[b]thiophen-4-yl-piperazin-1-yl)propoxy]-3,4-dihydro-1H-quinolin-2-one (1.6 g, 3.8 mmol) in tetrahydrofuran (40 ml), followed by stirring under reflux for 1 hour. The reaction mixture was cooled in an ice-bath, and water (0.16 ml), 15% sodium hydroxide aqueous solution (0.16 ml) and water (0.5 ml) were added thereto in this order. After stirring the mixture, insoluble matters were removed by filtration and the filtrate was concentrated under reduced pressure. The residue was purified by basic silica gel column chromatography (n-hexane:ethyl acetate=1:1), and concentrated under reduced pressure to obtain amorphous solid (1.4 g). The amorphous solid obtained (0.6 g) was dissolved in ethyl acetate (15 ml). 1N-HCl—ethanol solution (1.45 ml) was further added thereto, then crystals precipitated were filtered out and dried to obtain 6-[3-(4-benzo[b]thiophen-4-yl-piperazin-1-yl)propoxy]-1,2,3,4-tetrahydroquinoline hydrochloride (0.55 g) as white powder.

Melting point: 123.2-124.3° C.

Example 60

Preparation of 7-[3-(4-benzo[b]thiophen-4-yl-piperazin-1-yl)propoxy]-2-methyl-1,2,3,4-tetrahydroquinoline hydrochloride 37% Formaldehyde aqueous solution (0.15 ml, 1.8 mmol), MP-cyanoborohydride (2.41 mmol/g, 0.76 g, 1.8 mmol) and catalytic amount of acetic acid were added to a solution of 7-[3-(4-benzo[b]thiophen-4-yl-piperazin-1-yl)propoxy]-1,2,3,4-tetrahydroisoquinoline (0.25 g, 0.6 mmol)

in methanol (20 ml), followed by stirring at room temperature overnight. The resin was removed by filtration and the filtrate was concentrated under reduced pressure. The residue was purified by basic silica gel column chromatography (methylene chloride:methanol=20:1), and concentrated under reduced pressure. The residue (175 mg) was dissolved in ethyl acetate (5 ml). 1N-HCl—ethanol solution (0.42 ml) was further added thereto, then crystals precipitated were filtered out and dried to obtain 7-[3-(4-benzo[b]thiophen-4-yl-piperazin-1-yl)propoxy]-2-methyl-1,2,3,4-tetrahydroquinoline hydrochloride (103 mg, yield: 37%) as white powder.

Melting point: 260.1-262.8° C.

Example 61

Preparation of 4-[3-(4-benzo[b]thiophen-4-yl-piperazin-1-yl)propoxy]quinolin-2-carboxymethylamide dihydrochloride Ethyl 4-[3-(4-benzo[b]thiophen-4-yl-piperazin-1-yl)propoxy]-quinolin-2-carboxylate (0.28 g) was added to a methanol solution of 40% methylamine (10 ml), followed by stirring at room temperature for two days. The reaction mixture was concentrated under reduced pressure. The residue was purified by basic silica gel column chromatography (ethyl acetate:methanol=11:1), and concentrated under reduced pressure. The residue (166 mg) was dissolved in ethyl acetate. 1N-HCl—ethanol solution (0.7 ml) was further added thereto, then crystals precipitated were filtered out and dried to obtain 4-[3-(4-benzo[b]thiophen-4-yl-piperazin-1-yl)propoxy]quinolin-2-carboxymethylamide dihydrochloride (0.17 g, yield: 54%) as white powder.

Melting point: 224.0° C. (decomposed)

Example 62

Preparation of 4-[3-(4-benzo[b]thiophen-4-yl-piperazin-1-yl)propoxy]quinolin-2-carboxylic acid hydrochloride An aqueous solution of 4N lithium hydroxide (3 ml) was added to a methanol solution (7 ml) of ethyl 4-[3-(4-benzo[b]thiophen-4-yl-piperazin-1-yl)propoxy]-quinolin-2-carboxylate (1.5 g), followed by stirring at room temperature overnight. Then, water (10 ml) and aqueous solution (3 ml) of 4N lithium hydroxide were further added, followed by stirring at 50° C. for 11 hours. The reaction mixture was cooled in an ice-bath, and an aqueous solution (4 ml) of 6N-HCl was added thereto. Then, crystals precipitated were filtered out, washed with water and dried to obtain 4-[3-(4-benzo[b]thiophen-4-yl-piperazin-1-yl)propoxy]quinolin-2-carboxylic acid hydrochloride (1.43 g, yield: 98%) as white powder.

Melting point: 235.0° C.

Example 63

Preparation of 4-[3-(4-benzo[b]thiophen-4-yl-piperazin-1-yl)propoxy]quinolin-2-carboxamide Triethylamine (0.25 ml, 1.8 mmol) and isobutyl chloroformate (0.19 ml, 1.4 mmol) were added to a solution (10 ml) of 4-[3-(4-benzo[b]thiophen-4-yl-piperazin-1-yl)propoxy]quinolin-2-carboxylic acid (0.53 g, 1.2 mmol) in acetonitrile with cooling in an ice-bath, followed by stirring at 0° C. for 3 hours. 28% Aqueous ammonia (0.15 ml) was added thereto and the reaction mixture was stirred at room temperature for 5 minutes. Ethyl acetate was further added thereto, then the reaction mixture was washed with water and concentrated under reduced pressure. The residue was purified by basic silica gel column chromatography (n-hexane:ethyl acetate=3:1), and concentrated under reduced pressure. The residue (0.2 g) was dissolved and recrystallized from the mixed solvent of ethyl acetate and isopropyl ether to obtain 4-[3-(4-benzo[b]thiophen-4-yl-piperazin-1-yl)propoxy]-quinolin-2-carboxamide (79 mg, yield: 16%) as white powder.

Melting point: 153.0-154.5° C.

Examples 64 to 196

Compounds of Example 64 to 196 shown in the following Tables 1 to 21 can be prepared in the same manner as in Example 1, using corresponding starting materials. In the following Tables, compounds with the physical properties, such as crystalline form, m.p. (melting point), salt, $^1$H-NMR and MS (mass spectrum), were prepared actually.

TABLE 1

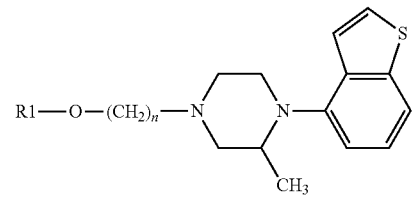

| Example No. | R1 | n | crystalline form (recrystallization solvent) | m.p. (° C.) | salt |
|---|---|---|---|---|---|
| 64 | | 3 | white powder (methanol) | 125-127 | — |

TABLE 1-continued

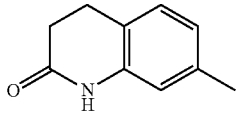

| Example No. | R1 | n | crystalline form (recrystallization solvent) | m.p. (° C.) | salt |
|---|---|---|---|---|---|
| 65 | 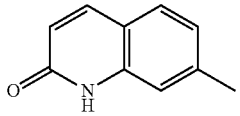 | 4 | white powder (ethanol-ethyl acetate) | 217-221 | dihydrochloride |
| 66 | 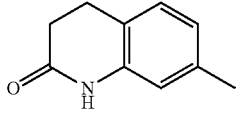 | 4 | white powder (ethyl acetate) | 123-130 (decomposed) | — |

TABLE 2

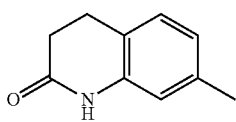

| Example No. | R1 | n | crystalline form (recrystallization solvent) | m.p. (° C.) | salt |
|---|---|---|---|---|---|
| 67 | 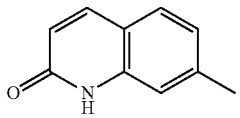 | 3 | white powder (ethanol) | 253-255 (decomposed) | hydrochloride |
| 68 | 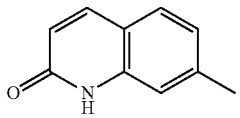 | 4 | white powder (ethanol-ethyl acetate-acetonitrile) | 151-153 | dihydrochloride |
| 69 | 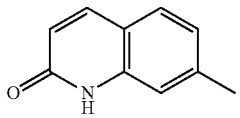 | 4 | white powder (ethanol) | 156-159 | hydrochloride |

TABLE 3

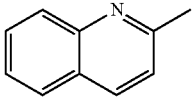

| Example No. | R1 | crystalline form (recrystallization solvent) | m.p. | salt |
|---|---|---|---|---|
| 70 | 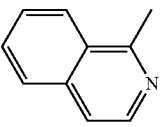 | colorless needle (ethanol) | 106.0-108.0 | — |
| 71 | 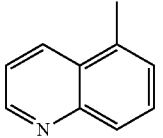 | white powder (ethanol) | 192.0-194.0 | hydrochloride |
| 72 | 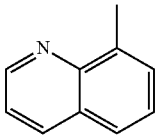 | light yellow powder (ethanol) | 240-242 | hydrochloride |
| 73 | 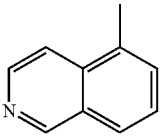 | light yellow powder (ethanol) | 199.0-201.0 | hydrochloride |
| 74 | 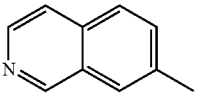 | white powder (ethanol) | 233.0-235.0 | hydrochloride |
| 75 | 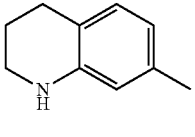 | yellow powder | 199.0-204.5 | dihydrochloride |
| 76 | 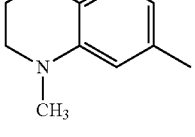 | white solid (ethyl acetate-hexane) | 123.2-124.3 | — |
| 77 | 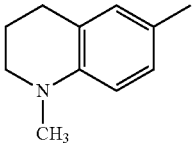 | white solid (ethyl acetate) | 231.3-232.9 | hydrochloride |
| 78 |  | white solid (ethyl acetate) | 229.6-231.8 | hydrochloride |

TABLE 3-continued

R1—O—(CH₂)₃—N(piperazine)N—(benzothiophen-4-yl)

| Example No. | R1 | crystalline form (recrystallization solvent) | m.p. | salt |
|---|---|---|---|---|
| 79 | 6-methyl-1-acetyl-1,2,3,4-tetrahydroquinolin-yl | white powder (ethyl acetate) | 237.0-238.5 | hydrochloride |
| 80 | 7-methyl-1,2,3,4-tetrahydroisoquinolin-yl (NH) | white solid (ethyl acetate) | 214.5-216.8 | hydrochloride |

TABLE 4

R1—O—(CH₂)ₙ—N(piperazine)N—(benzothiophen-4-yl)

| Example No. | R1 | crystalline form (recrystallization solvent) | m.p. | salt |
|---|---|---|---|---|
| 81 | 7-methyl-2-acetyl-1,2,3,4-tetrahydroisoquinolin-yl | white solid (ethyl acetate) | 207.9-208.7 | hydrochloride |
| 82 | ethyl 4-methylquinoline-2-carboxylate | light yellow powder (ethyl acetate-isopropyl ethyl) | 106.0-113.0 | — |
| 83 | 4-methyl-2-oxo-1,2-dihydroquinolin-yl | white powder (ethyl acetrate-ether) | 188-190 | — |

TABLE 5

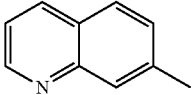

| Example No. | R1 | n | 1H-NMR (solvent) | salt |
|---|---|---|---|---|
| 84 | 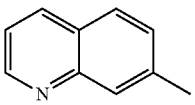 | 3 | 1H-NMR (CDCl3) δ ppm: 2.05-2.20 (2H, m), 2.65-2.77 (6H, m), 3-15-3.25 (41-1. m), 4.23 (2H, t, J = 6.3 Hz), 6.91 (1H, d, J = 7.1 Hz), 7.15-7.35 (3H, m). 7.35-7.45 (3H, m), 7.55 (1H, d, J = 8.0 Hz), 7.70 (1H, d, J = 8.9 Hz), 8.05-8.15 (1H, m), 8.83 (1H, dd, J = 1.7, 5.3 Hz). | — |
| 85 | 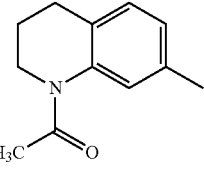 | 4 | 1H-NMR (DMSO-d6) d: 1.90-2_00 (4H. m), 3.25-3.40 (6H, m), 3.50-3.65 (4H, m), 4.20-4.35 (2H, m), 6.95 (1H, d, J = 7.4 Hz), 7.30 (1H, dd, J = 7.9, 7,9 Hz), 7.48 (1H, d, J = 5.5 Hz), 7.65-7.80 (3H, m), 7.80-7.95 (2H, m), 8.32 (1H, d, J = 9.2 Hz), 9.05-9.20 (2H, m), 11.29 (1H, brs). | dihydrochloride |

TABLE 6

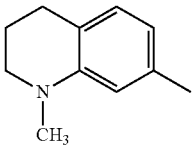

| Example No. | R1 | crystalline form (recrystallization solvent) | m.p. | salt |
|---|---|---|---|---|
| 86 | 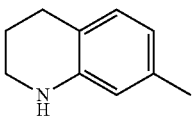 | white powder (ethyl acetate) | 239.6-241.5 | hydrochloride |
| 87 | 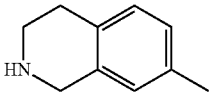 | light brown powder (ethyl acetate) | 228.3-229.5 | hydrochloride |
| 88 | 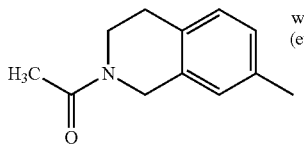 | white powder (ethyl acetate) | 212.3-214.4 | hydrochloride |
| 89 | | white powder (ethyl acetate) | 232.9-235.1 | hydrochloride |
| 90 | | white powder (ethyl acetate) | 165.8-167.9 | hydrochloride |

TABLE 6-continued
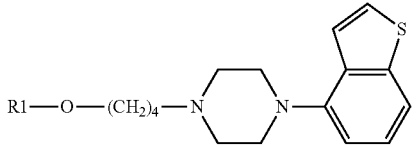
| Example No. | R1 | crystalline form (recrystallization solvent) | m.p. | salt |
|---|---|---|---|---|
| 91 | 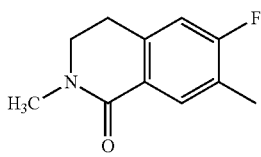 | white powder (ethanol) | 220-225 | hydrochloride |
| 92 | 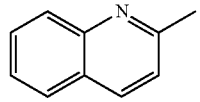 | white powder (ethanol) | 221-224 | hydrochloride |
| 93 | 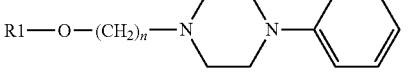 | white powder (ethanol) | 181-183 | hydrochloride |
TABLE 7
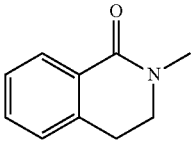
| Example No. | R1 | n | 1H-NMR (solvent) | salt |
|---|---|---|---|---|
| 94 |  | 3 | 1H-NMR (DMSO-d6) d: 2.01-2.12 (2H, m), 3.0-3.7 (16H, m), 6.98 (1H, d, J = 7.7 Hz), 7.29-7.39 (3H, m), 7.47-7.52 (2H, m), 7.70 (1H, d, J = 8.0 Hz), 7.77 (1H, d, J = 5.6 Hz), 7.89 (1H, a J = 7.7 Hz), 9.85 (1H br-s) | hydrochloride |
| 95 |  | 2 | 1H-NMR (CDCl3) d: 3.0-4.1 (16H, m), 6.94 (1H, d, J = 7.4 Hz), 7.20-7.47 (6H, m), 7.64 (1H, d, J = 8.1 Hz), 8.04 (1H, d, J = 7.4 Hz) | oxalate |

TABLE 8

[Structure: R1—O—(CH2)3—N(piperazine)N—benzothiophene]

| Example No. | R1 | crystalline form (recrystallization solvent) | m.p.(° C.) | salt |
|---|---|---|---|---|
| 96 | 1-cyclohexyl-7-methyl-3,4-dihydroquinolin-2(1H)-one-yl | white powder (ethyl acetate) | 185.5-190.0 | hydrochloride |
| 97 | 2-phenyl-6-methyl-3,4-dihydroisoquinolin-1(2H)-one-yl | white powder (ethyl acetate-ether) | 134-136 | — |
| 98 | 2-benzyl-6-methyl-3,4-dihydroisoquinolin-1(2H)-one-yl | white powder (ethyl acetate-ether) | 103-105 | — |
| 99 | 2-(cyclohexylmethyl)-6-methyl-3,4-dihydroisoquinolin-1(2H)-one-yl | white powder (ethyl acetate-ether) | 126-128 | — |
| 100 | 2-allyl-6-methyl-3,4-dihydroisoquinolin-1(2H)-one-yl | white powder (ethyl acetate-ether) | 97-99 | — |
| 101 | 2-propargyl-6-methyl-3,4-dihydroisoquinolin-1(2H)-one-yl | brown powder (methanol) | 240-242 | hydrochloride |
| 102 | 2-acetyl-6-methyl-3,4-dihydroisoquinolin-1(2H)-one-yl | white powder (ethyl acetate-ether) | 143-145 | — |
| 103 | 2-benzoyl-6-methyl-3,4-dihydroisoquinolin-1(2H)-one-yl | white powder (ethyl acetate-ether) | 161-163 | — |

TABLE 8-continued

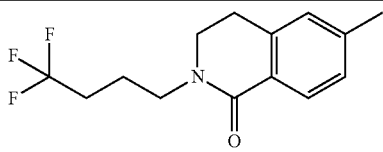

| Example No. | R1 | crystalline form (recrystallization solvent) | m.p.(° C.) | salt |
|---|---|---|---|---|
| 104 | (4,4,4-trifluorobutyl group) | white powder (ethyl acetate-ether) | 122-124 | — |

TABLE 9

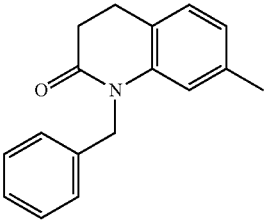

| Example No. | R1 | crystalline form (recrystallization solvent) | m.p.(° C.) | salt |
|---|---|---|---|---|
| 105 | (1-benzyl-7-methyl-3,4-dihydroquinolin-2(1H)-one) | white powder (ethyl acetate) | 212.5-216.0 | hydrochloride |
| 106 | (1-(cyclohexylmethyl)-7-methyl-3,4-dihydroquinolin-2(1H)-one) | white powder (ethyl acetate) | 224.5-230.0 | hydrochloride |
| 107 | (1-(but-2-enyl)-7-methyl-3,4-dihydroquinolin-2(1H)-one) | white powder (ethyl acetate) | 172.0-174.5 | hydrochloride |
| 108 | (1-(prop-2-ynyl)-7-methyl-3,4-dihydroquinolin-2(1H)-one) | white powder (ethyl acetate) | 196.5-201.5 | hydrochloride |

TABLE 9-continued
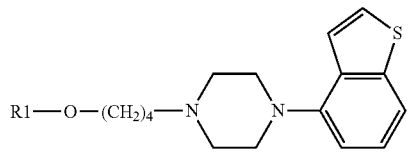
| Example No. | R1 | crystalline form (recrystallization solvent) | m.p.(° C.) | salt |
|---|---|---|---|---|
| 109 | 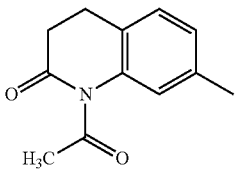 | white powder (ethyl acetate) | 200.5-205.5 | hydrochloride |
| 110 | 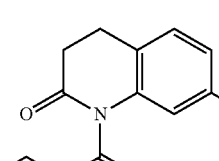 | white powder (ethyl acetate) | 202.5-206.5 | hydrochloride |
| 111 | 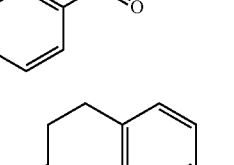 | white powder (ethyl acetate) | 218.0-223.5 | hydrochloride |
| 112 | 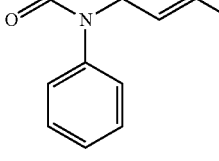 | white powder (ethyl acetate-isopropyl ether) | 125.0-129.0 | — |
TABLE 10
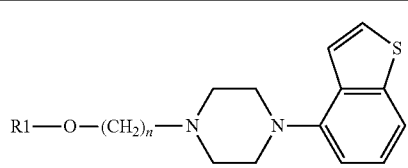
| Example No. | R1 | n | MS(M + 1) |
|---|---|---|---|
| 113 | 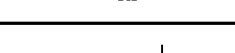 | 3 | 454 |
TABLE 10-continued
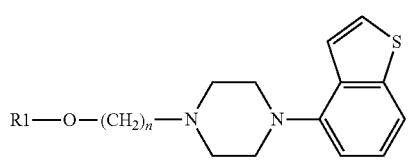
| Example No. | R1 | n | MS(M + 1) |
|---|---|---|---|
| 114 | 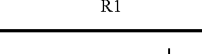 | 3 | 501 |

TABLE 10-continued

R1—O—(CH₂)ₙ—[piperazine]—[benzothiophene]

| Example No. | R1 | n | MS(M + 1) |
|---|---|---|---|
| 115 | 3-ethyl-4-methyl-2-oxo-1,2-dihydroquinolin-yl | 3 | 448 |
| 116 | 8-fluoro-6-methyl-2-oxo-1,2,3,4-tetrahydroquinolin-yl | 3 | 440 |
| 117 | 3,8-dimethyl-2-oxo-1,2-dihydroquinolin-yl | 3 | 434 |
| 118 | 8-fluoro-6-methyl-2-oxo-1,2-dihydroquinolin-yl | 3 | 438 |
| 119 | 7-methyl-3-(thiophen-2-yl)-2-oxo-1,2-dihydroquinolin-yl | 3 | 502 |
| 120 | 8-chloro-6-methyl-2-oxo-1,2,3,4-tetrahydroquinolin-yl | 3 | 457 |
| 121 | 8-methyl-2-oxo-1,2-dihydroquinolin-yl | 3 | 420 |

TABLE 11

R1—O—(CH₂)ₙ—[piperazine]—[benzothiophene]

| Example No. | R1 | n | MS(M + 1) |
|---|---|---|---|
| 122 | 5-methyl-2-oxo-1,2,3,4-tetrahydroquinolin-yl | 3 | 422 |
| 123 | 8-methyl-2-oxo-1,2,3,4-tetrahydroquinolin-yl | 3 | 422 |
| 124 | 8-bromo-5-methyl-2-oxo-1,2-dihydroquinolin-yl | 3 | 499 |
| 125 | 8-bromo-6-chloro-7-methyl-2-oxo-1,2,3,4-tetrahydroquinolin-yl | 3 | 535 |
| 126 | 8-chloro-5-methyl-2-oxo-1,2,3,4-tetrahydroquinolin-yl | 3 | 457 |
| 127 | 5-(allyloxy)-8-methyl-2-oxo-1,2,3,4-tetrahydroquinolin-yl | 3 | 478 |
| 128 | 5-acetoxy-8-methyl-2-oxo-1,2,3,4-tetrahydroquinolin-yl | 3 | 480 |

TABLE 11-continued

R1—O—(CH₂)ₙ—N(piperazine)N—(benzothiophen-4-yl)

| Example No. | R1 | n | MS(M + 1) |
|---|---|---|---|
| 129 | 6-bromo-5-methyl-quinolin-2(1H)-one | 3 | |

TABLE 12

R1—O—(CH₂)ₙ—N(piperazine)N—(benzothiophen-4-yl)

| Example No. | R1 | n | MS(M + 1) |
|---|---|---|---|
| 130 | 5-bromo-8-methyl-quinolin-2(1H)-one | 3 | 499 |
| 131 | 6,8-dimethyl-quinolin-2(1H)-one | 3 | 434 |
| 132 | 5,6-dichloro-8-methyl-quinolin-2(1H)-one | 3 | |
| 133 | 5,8-dimethyl-quinolin-2(1H)-one | 3 | 434 |
| 134 | 5-benzyloxy-8-methyl-3,4-dihydroquinolin-2(1H)-one | 3 | 528 |

TABLE 12-continued

R1—O—(CH₂)ₙ—N(piperazine)N—(benzothiophen-4-yl)

| Example No. | R1 | n | MS(M + 1) |
|---|---|---|---|
| 135 | 8-methyl-5-nitro-quinolin-2(1H)-one | 3 | 465 |
| 136 | 8-methoxy-4-methyl-quinolin-2(1H)-one | 3 | 450 |
| 137 | 7-acetyl-8-methyl-quinolin-2(1H)-one | 3 | 462 |

TABLE 13

R1—O—(CH₂)ₙ—N(piperazine)N—(benzothiophen-4-yl)

| Example No. | R1 | n | MS(M + 1) |
|---|---|---|---|
| 138 | 5,7-dichloro-8-methyl-quinolin-2(1H)-one | 3 | |
| 139 | 6-(hydroxymethyl)-7-methyl-3,4-dihydroquinolin-2(1H)-one | 3 | 452 |

TABLE 13-continued

R1—O—(CH2)n—[piperazine]—[benzothiophene]

| Example No. | R1 | n | MS(M + 1) |
|---|---|---|---|
| 140 | 8-methyl-2-oxo-1,2-dihydroquinolin-5-yl | 3 | 448 |
| 141 | 4-methyl-3-phenyl-2-oxo-1,2-dihydroquinolin-yl | 3 | 496 |
| 142 | 7-methyl-4-phenyl-2-oxo-1,2-dihydroquinolin-yl | 3 | |
| 143 | 5-acetyl-8-methyl-2-oxo-1,2-dihydroquinolin-yl | 3 | 462 |
| 144 | 6-((dimethylamino)methyl)-5,8-dimethyl-2-oxo-1,2-dihydroquinolin-yl | 3 | 491 |
| 145 | 5,6,8-trimethyl-2-oxo-1,2-dihydroquinolin-yl | 3 | |

TABLE 14

R1—O—(CH2)n—[piperazine]—[benzothiophene]

| Example No. | R1 | n | MS(M + 1) |
|---|---|---|---|
| 146 | 6-methyl-4-phenyl-2-oxo-1,2,3,4-tetrahydroquinolin-yl | 3 | 498 |
| 147 | 5-acetyl-8-methyl-2-oxo-3,4-dihydroquinolin-yl | 3 | |
| 148 | 7-acetyl-6-methyl-2-oxo-3,4-dihydroquinolin-yl | 3 | 464 |
| 149 | 6-bromo-7-methyl-2-oxo-3,4-dihydroquinolin-yl | 3 | 501 |
| 150 | methyl 7-methyl-2-oxo-3,4-dihydroquinoline-6-carboxylate | 3 | 480 |
| 151 | 6-allyl-7-methyl-2-oxo-3,4-dihydroquinolin-yl | 3 | 462 |
| 152 | 5-methyl-6-nitro-2-oxo-3,4-dihydroquinolin-yl | 3 | 467 |

TABLE 14-continued
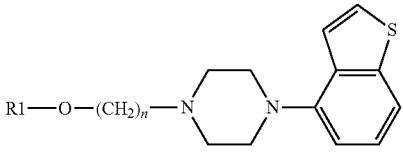
| Example No. | R1 | n | MS(M + 1) |
|---|---|---|---|
| 153 | 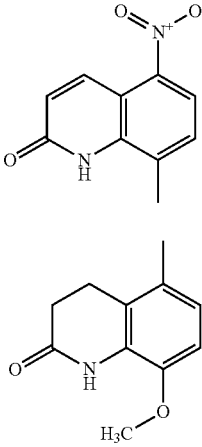 | 3 | 467 |
| 154 | 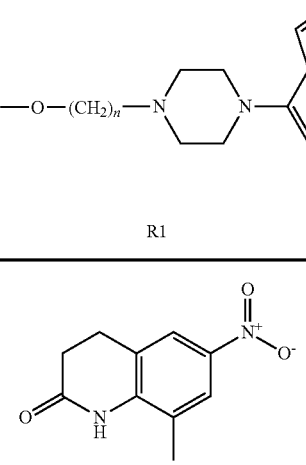 | 3 | 452 |
TABLE 15
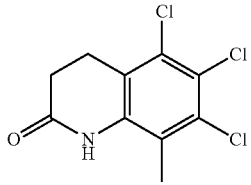
| Example No. | R1 | n | MS(M + 1) |
|---|---|---|---|
| 155 | 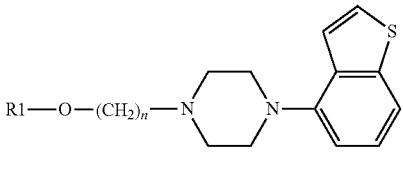 | 3 | 479 |
| 156 | 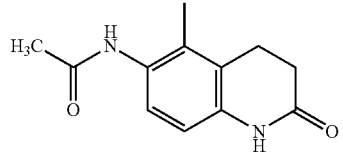 | 3 | |
| 157 | 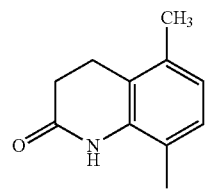 | 3 | 436 |
TABLE 15-continued
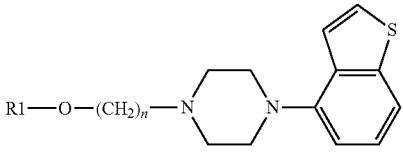
| Example No. | R1 | n | MS(M + 1) |
|---|---|---|---|
| 158 | 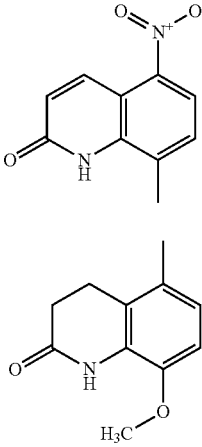 | 3 | 467 |
| 159 | 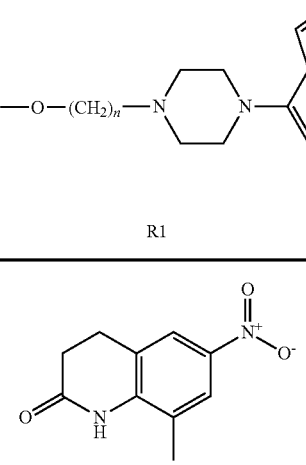 | 3 | 525 |
| 160 | 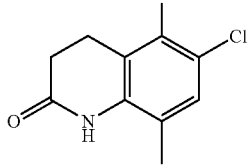 | 3 | |
| 161 | 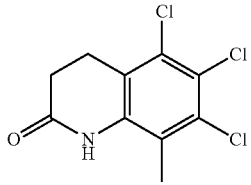 | 3 | |
| 162 | 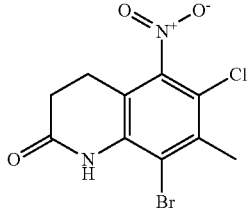 | 3 | 491 |

TABLE 16

R1—O—(CH₂)ₙ—N(piperazine)N—(benzothiophen-4-yl)

| Example No. | R1 | n | MS(M + 1) |
|---|---|---|---|
| 163 | 6,8-dichloro-7-methyl-3,4-dihydroquinolin-2(1H)-one | 3 | 491 |
| 164 | ethyl 5-methyl-2-oxo-1,2,3,4-tetrahydroquinoline-6-carboxylate | 3 | 494 |
| 165 | 6,8-diallyl-7-methyl-3,4-dihydroquinolin-2(1H)-one | 3 | |
| 166 | 7-((dimethylamino)methyl)-6-methyl-3,4-dihydroquinolin-2(1H)-one | 3 | |
| 167 | 5-((dimethylamino)methyl)-6,7-dimethyl-3,4-dihydroquinolin-2(1H)-one | 3 | |
| 168 | 6-((dimethylamino)methyl)-7-methyl-3,4-dihydroquinolin-2(1H)-one | 3 | 479 |
| 169 | 6,7-dimethyl-8-(pyrrolidin-1-ylmethyl)-3,4-dihydroquinolin-2(1H)-one | 3 | 519 |

TABLE 16-continued

R1—O—(CH₂)ₙ—N(piperazine)N—(benzothiophen-4-yl)

| Example No. | R1 | n | MS(M + 1) |
|---|---|---|---|
| 170 | 7-allyl-6-methyl-5-(pyrrolidin-1-ylmethyl)-3,4-dihydroquinolin-2(1H)-one | 3 | |

TABLE 17

R1—O—(CH₂)ₙ—N(piperazine)N—(benzothiophen-4-yl)

| Example No. | R1 | n | MS(M + 1) |
|---|---|---|---|
| 171 | 6-((dimethylamino)methyl)-5-methyl-3,4-dihydroquinolin-2(1H)-one | 3 | 479 |
| 172 | 1,4,8-trimethylquinolin-2(1H)-one | 3 | 448 |
| 173 | 6-methyl-3,4-dihydroquinolin-2(1H)-one | 2 | 408 |
| 174 | 7-methyl-3,4-dihydroquinolin-2(1H)-one | 2 | |
| 175 | 6-methylquinolin-2(1H)-one | 2 | 406 |

TABLE 17-continued

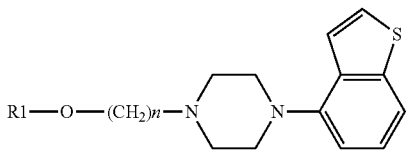

| Example No. | R1 | n | MS(M + 1) |
|---|---|---|---|
| 176 | 6-methyl-8-chloro-3,4-dihydroquinolin-2(1H)-one | 2 | 442 |
| 177 | 5-methyl-3,4-dihydroquinolin-2(1H)-one | 2 | 408 |
| 178 | 8-methyl-3,4-dihydroquinolin-2(1H)-one | 2 | 408 |
| 179 | 5-methyl-3,4-dihydroquinolin-2(1H)-one | 5 | 450 |
| 180 | 1,8-dimethyl-4-methylquinolin-2(1H)-one | 8 | 518 |

TABLE 18

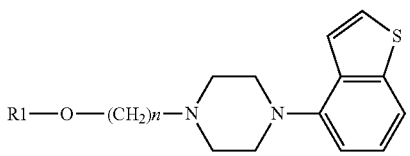

| Example No. | R1 | n | MS(M + 1) |
|---|---|---|---|
| 181 | 6-chloro-7-methyl-3,4-dihydroquinolin-2(1H)-one | 4 | 471 |
| 182 | 6-fluoro-7-methyl-3,4-dihydroquinolin-2(1H)-one | 4 | |
| 183 | 6-methyl-8-chloro-quinolin-2(1H)-one | 4 | 469 |
| 184 | 8-fluoro-6-methyl-quinolin-2(1H)-one | 4 | 452 |
| 185 | 4,6-dimethyl-quinolin-2(1H)-one | 4 | 448 |
| 186 | 8-methyl-3,4-dihydroquinolin-2(1H)-one | 4 | 436 |
| 187 | 5-methyl-3,4-dihydroquinolin-2(1H)-one | 4 | 436 |
| 188 | 8-methyl-quinolin-2(1H)-one | 4 | 434 |
| 189 | 5-methoxy-8-methyl-quinolin-2(1H)-one | 4 | 450 |
| 190 | 5-hydroxy-8-methyl-3,4-dihydroquinolin-2(1H)-one | 3 | 438 |

TABLE 19

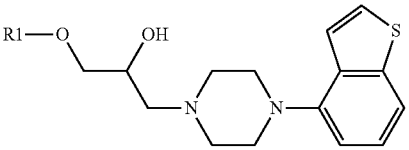

| Example No. | R1 | MS(M + 1) |
|---|---|---|
| 191 | 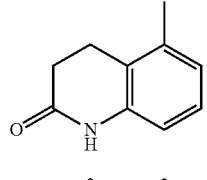 | 438 |
| 192 | 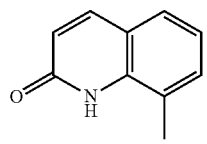 | 438 |
| 193 | 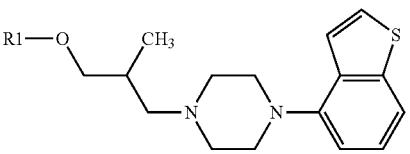 | 436 |

TABLE 20

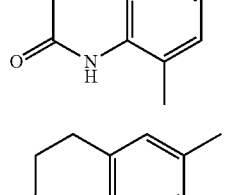

| Example No. | R1 | MS(M + 1) |
|---|---|---|
| 194 | 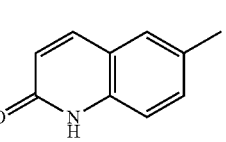 | 436 |
| 195 | 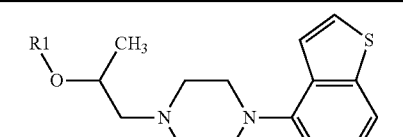 | 436 |
| 196 |  | 434 |

TABLE 21

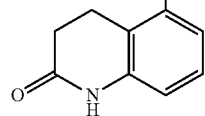

TABLE 21-continued

| Example No. | R1 | MS(M + 1) |
|---|---|---|
| 197 | | |

Pharmacological Test 1

1) Dopamine $D_2$ Receptor Binding Assay

The assay was performed according to the method by Kohler et al. (Kohler C, Hall H, Ogren S O and Gawell L, Specific in vitro and in vivo binding of 3H-raclopride. A potent substituted benzamide drug with high affinity for dopamine D-2 receptors in the rat brain. Biochem. Pharmacol., 1985; 34: 2251-2259).

Wistar male rats were decapitated, the brain was retrieved immediately and corpus striatum was taken out. It was homogenized in 50 mM tris(hydroxymethyl)aminomethane (Tris)-hydrochloric acid buffer (pH 7.4) of a volume 50 times of the weight of the tissue using a homogenizer with a high-speed rotating blade, and centrifuged at 4° C., 48,000×g for 10 minutes. The obtained precipitate was suspended again in the above-described buffer of a volume 50 times of the weight of the tissue and after incubated at 37° C. for 10 minutes, centrifuged in the above-described condition. The obtained precipitate was suspended in 50 mM (Tris)-hydrochloric acid buffer (containing 120 mM NaCl, 5 mM KCl, 2 mM $CaCl_2$, 1 mM $MgCl_2$, pH 7.4) of a volume 25 times of the weight of the tissue and preserved by freezing at −85° C. till it was used for binding assay as a membrane specimen.

The binding assay was performed using 40 μl of the membrane specimen, 20 μl of [$^3$H]-raclopride (final concentration 1 to 2 nM), 20 μl of a test drug and 50 mM Tris-hydrochloric acid buffer (containing 120 mM NaCl, 5 mM KCl, 2 mM $CaCl_2$, 1 mM $MgCl_2$, pH 7.4) so that the total amount was 200 μl (final dimethylsulfoxide concentration 1%). The reaction was performed at room temperature for 1 hour and terminated by conducting suction filtration with a cell harvester on a glass fiber filter plate. The filter plate made of glass fiber was washed with 50 mM Tris-hydrochloric acid buffer (pH 7.4), and after dried, a microplate liquid scintillation cocktail was added and the radioactivity was measured with a microplate scintillation counter. Radioactivity in the presence of 10 μM (+)-butaclamol hydrochloride was assumed as nonspecific binding.

$IC_{50}$ value was calculated from concentration-dependent reaction using a non-linear analysis program. Ki value was calculated from $IC_{50}$ value using Cheng-Prussoff formula. The results are shown in the following Table 22.

TABLE 22

| Test Compound | Ki (nM) |
|---|---|
| Compound of Example 1 | 0.2 |
| Compound of Example 3 | 0.5 |
| Compound of Example 4 | 0.5 |
| Compound of Example 5 | 0.6 |
| Compound of Example 6 | 0.8 |
| Compound of Example 7 | 0.5 |
| Compound of Example 10 | 0.4 |
| Compound of Example 11 | 0.1 |
| Compound of Example 12 | 0.1 |

TABLE 22-continued

| Test Compound | Ki (nM) |
| --- | --- |
| Compound of Example 13 | 2.4 |
| Compound of Example 14 | 3.2 |
| Compound of Example 15 | 0.2 |
| Compound of Example 16 | 0.7 |
| Compound of Example 17 | 2.2 |
| Compound of Example 18 | 2.6 |
| Compound of Example 19 | 1.2 |
| Compound of Example 20 | 1.5 |
| Compound of Example 22 | 4.0 |
| Compound of Example 23 | 0.7 |
| Compound of Example 24 | 5.0 |
| Compound of Example 26 | 3.5 |
| Compound of Example 27 | 4.9 |
| Compound of Example 28 | 1.2 |
| Compound of Example 30 | 0.7 |
| Compound of Example 31 | 1.4 |
| Compound of Example 32 | 1.5 |
| Compound of Example 33 | 1.1 |
| Compound of Example 34 | 1.2 |
| Compound of Example 35 | 1.6 |
| Compound of Example 36 | 1.0 |
| Compound of Example 37 | 1.9 |
| Compound of Example 38 | 1.2 |
| Compound of Example 39 | 1.2 |
| Compound of Example 40 | 4.8 |
| Compound of Example 41 | 1.9 |
| Compound of Example 64 | 3.2 |
| Compound of Example 68 | 1.0 |
| Compound of Example 69 | 0.8 |
| Compound of Example 73 | 4.0 |
| Compound of Example 79 | 4.7 |
| Compound of Example 80 | 1.5 |
| Compound of Example 81 | 0.8 |
| Compound of Example 84 | 2.4 |
| Compound of Example 85 | 2.0 |
| Compound of Example 90 | 0.4 |
| Compound of Example 91 | 1.4 |
| Compound of Example 92 | 1.7 |
| Compound of Example 116 | 4.5 |
| Compound of Example 117 | 4.7 |
| Compound of Example 118 | 3.5 |
| Compound of Example 122 | 3.3 |
| Compound of Example 128 | 1.3 |
| Compound of Example 139 | 0.2 |
| Compound of Example 155 | 2.3 |
| Compound of Example 163 | 2.8 |
| Compound of Example 184 | 2.6 |
| Compound of Example 185 | 2.7 |
| Compound of Example 186 | 2.3 |
| Compound of Example 188 | 1.6 |
| Compound of Example 190 | 0.8 |

2) Serotonin 5-HT$_{2A}$ Receptor Binding Assay

The assay was performed according to the method by Leysen J E et al. (Leysen J E, Niemegeers C J E, Van Nueten J M and Laduron P M. [3H] Ketanserin (R 41 468), a selective 3H-ligand for serotonin 2 receptor binding sites. Mol. Pharmacol., 1982, 21: 301-314).

Wistar male rats were decapitated, the brain was retrieved immediately and frontal cortex was taken out. It was homogenized in 0.25 M sucrose of a volume 10 times of the weight of the tissue using a Teflon glass homogenizer, and centrifuged at 4° C., 1,000×g for 10 minutes. The obtained supernatant was transferred to another centrifuge tube and suspended in 0.25 M sucrose of a volume 5 times of the weight of the tissue and the precipitate was centrifuged in the above-described condition. The obtained supernatant was combined with the supernatant obtained above and adjusted to a volume 40 times of the weight of the tissue with 50 mM Tris-hydrochloric acid buffer (pH 7.4), and centrifuged at 4° C., 35,000×g for 10 minutes. The obtained precipitate was suspended again in the above-described buffer of a volume 40 times of the weight of the tissue and centrifuged in the above-described condition. The obtained precipitate was suspended in the above-described buffer of a volume 20 times of the weight of the tissue and preserved by freezing at −85° C. till it was used for binding assay as a membrane specimen.

The binding assay was performed using 40 μl of the membrane specimen, 20 μl of [$^3$H]-Ketanserin (final concentration 1 to 3 nM), 20 μl of a test drug and 50 mM Tris-hydrochloric acid buffer (pH 7.4) so that the total amount was 200 μl (final dimethylsulfoxide concentration 1%). The reaction was performed at 37° C. for 20 minutes and terminated by conducting suction filtration with a cell harvester on a glass fiber filter plate.

The filter plate made of glass fiber was washed with 50 mM Tris-hydrochloric acid buffer (pH 7.4), and after dried, a microplate liquid scintillation cocktail was added and the radioactivity was measured with a microplate scintillation counter. Radioactivity in the presence of 10 μM spiperone was assumed as nonspecific binding.

IC$_{50}$ value was calculated from concentration-dependent reaction using a non-linear analysis program. Ki value was calculated from IC$_{50}$ value using Cheng-Prussoff formula. The results are shown in the following Table 23.

TABLE 23

| Test Compound | Ki (nM) |
| --- | --- |
| Compound of Example 1 | 2.3 |
| Compound of Example 2 | 1.5 |
| Compound of Example 3 | 2.3 |
| Compound of Example 4 | 4.9 |
| Compound of Example 5 | 6.4 |
| Compound of Example 7 | 4.0 |
| Compound of Example 8 | 0.6 |
| Compound of Example 9 | 2.6 |
| Compound of Example 10 | 3.0 |
| Compound of Example 11 | 5.7 |
| Compound of Example 12 | 2.1 |
| Compound of Example 15 | 3.3 |
| Compound of Example 16 | 7.0 |
| Compound of Example 17 | 2.8 |
| Compound of Example 18 | 8.0 |
| Compound of Example 19 | 1.2 |
| Compound of Example 20 | 3.3 |
| Compound of Example 21 | 1.0 |
| Compound of Example 22 | 2.9 |
| Compound of Example 23 | 1.7 |
| Compound of Example 24 | 2.3 |
| Compound of Example 25 | 4.6 |
| Compound of Example 26 | 4.4 |
| Compound of Example 27 | 4.1 |
| Compound of Example 28 | 2.8 |
| Compound of Example 30 | 2.0 |
| Compound of Example 31 | 4.5 |
| Compound of Example 32 | 8.6 |
| Compound of Example 33 | 6.6 |
| Compound of Example 34 | 1.5 |
| Compound of Example 35 | 2.1 |
| Compound of Example 36 | 2.1 |
| Compound of Example 37 | 3.1 |
| Compound of Example 38 | 7.3 |
| Compound of Example 39 | 2.1 |
| Compound of Example 40 | 5.1 |
| Compound of Example 41 | 3.2 |
| Compound of Example 64 | 8.2 |
| Compound of Example 68 | 7.0 |
| Compound of Example 69 | 6.1 |
| Compound of Example 73 | 1.3 |
| Compound of Example 79 | 5.5 |
| Compound of Example 80 | 2.5 |
| Compound of Example 81 | 2.6 |
| Compound of Example 84 | 3.3 |
| Compound of Example 89 | 3.1 |
| Compound of Example 90 | 5.3 |
| Compound of Example 91 | 6.5 |

TABLE 23-continued

| Test Compound | Ki (nM) |
| --- | --- |
| Compound of Example 92 | 5.7 |
| Compound of Example 116 | 4.2 |
| Compound of Example 117 | 1.3 |
| Compound of Example 118 | 3.4 |
| Compound of Example 122 | 2.9 |
| Compound of Example 128 | 6.3 |
| Compound of Example 139 | 4.0 |
| Compound of Example 155 | 3.0 |
| Compound of Example 163 | 7.4 |
| Compound of Example 184 | 4.3 |
| Compound of Example 185 | 5.0 |
| Compound of Example 186 | 8.8 |
| Compound of Example 188 | 6.3 |
| Compound of Example 190 | 2.9 |

3) Adrenalin α1 Receptor Binding Assay

The assay was performed according to the method by Groβ G et al. (Groβ G, Hanft G and Kolassa N. Urapidil and some analogues with hypotensive properties show high affinities for 5-hydroxytryptamine (5-HT) binding sites of the 5-HT1A subtype and for α1-adrenoceptor binding sites. Naunyn-Schmiedeberg's Arch Pharmacol., 1987, 336: 597-601).

Wistar male rats were decapitated, the brain was retrieved immediately and cerebral cortex was taken out. It was homogenized in 50 mM Tris-hydrochloric acid buffer (100 mM NaCl, containing 2 mM dihydrogen disodium ethylene diamine tetraacetate, pH 7.4) of a volume 20 times of the weight of the tissue using a homogenizer with a high-speed rotating blade, and centrifuged at 4° C., 80,000×g for 20 minutes. The obtained precipitate was suspended in the above-described buffer of a volume 20 times of the weight of the tissue and after incubated at 37° C. for 10 minutes, centrifuged in the above-described condition. The obtained precipitate was suspended again in the above-described buffer of a volume 20 times of the weight of the tissue and centrifuged in the above-described condition. The obtained precipitate was suspended in 50 mM (Tris)-hydrochloric acid buffer (containing 1 mM dihydrogen disodium ethylene diamine tetraacetate, pH 7.4) of a volume 20 times of the weight of the tissue and preserved by freezing at −85° C. till it was used for binding assay as a membrane specimen.

The binding assay was performed using 40 μl of the membrane specimen, 20 μl of [3H]-prazosin (final concentration 0.2 to 0.5 nM), 20 μl of a test drug and 50 mM Tris-hydrochloric acid buffer (containing 1 mM EDTA, pH 7.4) so that the total amount was 200 μl (final dimethylsulfoxide concentration 1%). The reaction was performed at 30° C. for 45 minutes and terminated by conducting suction filtration with a cell harvester on a glass fiber filter plate.

The filter plate made of glass fiber was washed with 50 mM Tris-hydrochloric acid buffer (pH 7.4), and after dried, a microplate liquid scintillation cocktail was added and the radioactivity was measured with a microplate scintillation counter. Radioactivity in the presence of 10 μM phentolamine hydrochloride was assumed as nonspecific binding.

$IC_{50}$ value was calculated from concentration-dependent reaction using a non-linear analysis program. Ki value was calculated from $IC_{50}$ value using Cheng-Prussoff formula.

Pharmacological Test 2

Partial Agonistic Activity on Dopamine $D_2$ Receptor Using $D_2$ Receptor Expression Cells Partial agonistic activity on dopamine $D_2$ receptor was evaluated by quantitatively determining cyclic AMP production inhibitory effect of a test compound in dopamine $D_2$ receptor expression cells in which adenosine 3',5'-cyclic monophosphate (cyclic AMP) production was induced by forskolin stimulation.

Human recombinant dopamine $D_2$ receptor expressing Chinese hamster ovary/DHFR(−) cells were cultured in a culture medium (Iscove's Modified Dulbecco's Medium (IMDM culture medium), 10% fetal bovine serum, 50 I.U./ml penicillin, 50 μg/ml streptomycin, 200 μg/ml geneticin, 0.1 mM sodium hypoxanthine, 16 μM thymidine) at 37° C. and 5% carbon dioxide condition. Cells were seeded at $10^4$ cells/well on a 96-well microtiter plate coated with poly-L-lysine and grown under the same condition for 2 days. Each well was washed with 100 μl of a culture medium (IMDM culture medium, 0.1 mM sodium hypoxanthine, 16 μM thymidine). The culture medium was replaced with 50 μl of culture medium (IMDM culture medium, 0.1% sodium ascorbate, 0.1 mM sodium hypoxanthine, 16 μM thymidine) having dissolved therein 3 μM of a test compound. After allowed to incubate at 37° C., 5% carbon dioxide condition for 20 minutes, the culture medium was replaced with 100 μl of forskolin stimulative culture medium (IMDM culture medium, 0.1% sodium ascorbate, 0.1 mM sodium hypoxanthine, 16 μM thymidine, 10 μM forskolin, 500 μM 3-isobutyl-1-methylxanthine) having 3 μM of the test compound dissolved therein and allowed to incubate at 37° C., 5% carbon dioxide condition for 10 minutes. After the culture medium was removed, 200 μl of Lysis 1B aqueous solution (Amersham Bioscience, reagent attached to cyclic AMP biotrack enzyme immunoassay system) was dispensed and shaken for 10 minutes. The aqueous solution of each well was used as a sample for measurement. Samples for measurement quadruply diluted were subjected to measurement of the quantity of cyclic AMP using the above-described enzyme immunoassay system. Inhibition ratio of the respective test compound was calculated assuming that the quantity of cyclic AMP of the well to which no test compound was added was 100%. In this empiric test system, dopamine which was used as a control drug suppressed the quantity of cyclic AMP to about 10% as the maximum activity.

It was confirmed that test compounds had partial agonistic activity for dopamine $D_2$ receptor in the above-described test.

Since the test compounds has partial agonistic activity for dopamine $D_2$ receptor, they can stabilize dopamine neurotransmission to a normal condition in a schizophrenia patient and as a result, exhibit, for example, positive and negative condition improving effect, cognitive impairment improving effect and the other symptom improving effects without causing side effects.

Pharmacological Test 3

Inhibitory Effect on Apomorphine-Induced Stereotyped Behavior in Rats

Wistar rats (male, six-seven weeks old, Japan SLC, Inc.) were used as test animals. A test compound was suspended in 5% gum arabic/(physiological saline or water) using an agate mortar and was diluted with the same solvent if necessary.

Test animals were fasted overnight from the day before. Apomorphine (0.7 mg/kg) was subcutaneously administered (1 ml/kg) 1 hour after each test compound was orally administered (5 ml/kg). Stereotyped behavior was observed for 1 minute respectively 20, 30 and 40 minutes after apomorphine injection.

The stereotyped behavior of each animal was quantified according to the following condition and score made at three points were summed up and the anti-apomorphine effect was evaluated. Six test animals were used for each group.

0: The appearance of the animals is the same as saline treated rats;

1: Discontinuous sniffing, constant exploratory activity;

2: Continuous sniffing, periodic exploratory activity;

3: Continuous sniffing, discontinuous biting, gnawing or licking. Very brief periods of locomotor activity;

4: Continuous biting, gnawing or licking; no exploratory activity.

Non-clinical statistical analysis system was used for all statistical processing. When the significance probability value was lower than 0.05, it was judged that a significant difference existed. The difference of the score between the solvent administration group and each test compound administration group was analyzed using Wilcoxon rank-sum test or Steel test. In addition, linear regression analysis was used for calculating 50% effective dose (95% confidence interval).

Since the test compounds showed inhibitory effect for apomorphine-induced stereotyped behavior, it was confirmed that the test compounds have $D_2$ receptor antagonistic effect.

Pharmacological Test 4

Inhibitory Effect on (±) D-2,5-Dimethoxy-4-Iodoamphetamine (DOI) Induced Head Twitch in Rats Wistar rats (male, six-seven weeks old, Japan SLC, Inc.) were used as test animals. A test compound was suspended in 5% gum arabic/(physiological saline or water) using an agate mortar and was diluted with the same solvent if necessary.

Test animals were fasted overnight from the day before. DOI (5.0 mg/kg) was subcutaneously administered (1 ml/kg) 1 hour after each test compound was orally administered (5 ml/kg). The number of head twitches was counted for 10 minutes immediately after DOI injection. Six test animals were used for each group.

Non-clinical statistical analysis was used for all statistical processing. When the significance probability value was lower than 0.05, it was judged that a significant difference existed. The difference of the number of head twitches between the solvent administration group and each test compound administration group was analyzed using t-test or Dunnett's test. In addition, linear regression analysis was used for calculating 50% effective dose (95% confidence interval).

Since the test compounds showed inhibitory effect for DOI-induced head twitch, it was confirmed that the test compounds have serotonin $5HT_{2A}$ receptor antagonistic effect.

Pharmacological Test 5

Catalepsy Inducing Effect in Rats

Wistar rats (male, six-seven weeks old, Japan SLC, Inc.) were used as test animals. A test compound was suspended in 5% gum arabic/(physiological saline or water) using an agate mortar and was diluted with the same solvent if necessary.

Test animals were fasted overnight from the day before observation on catalepsy and ptosis was performed 1, 2, 4, 6 and 8 hours after each test compound was orally administered (5 ml/kg). Six test animals were used for each group.

One forepaw of a rat was placed on an edge of a steel small box (width: 6.5 cm, depth: 4.0 cm, height: 7.2 cm) (an unnatural pose) and when the rat maintained the pose for more than 30 seconds, it was judged that the case was catalepsy positive. This observation was performed three times at each point, and if there was at least one positive case, it was judged that catalepsy occurred in the individual.

As a result, catalepsy induction effect of a test compound was dissociated from inhibitory effect on apomorphine-induced stereotyped behavior, therefore it was suggested that apprehension for extrapyramidal side effect in clinic would be low.

Pharmacological Test 6

Measurement of Serotonin (5-HT) Uptake Inhibitory Activity of a Test Compound by Rat Brain Synaptosome Wistar male rats were decapitated, the brain was retrieved and frontal cortex was dissected out, and it was homogenized in 0.32 M sucrose solution of a weight 20 times of the weight of the tissue using a Potter type homogenizer. The homogenate was centrifuged at 4° C., 1,000×g for 10 minutes, the obtained supernatant was further centrifuged at 4° C., 20,000×g for 20 minutes, and the pellet was suspended in an incubation buffer (20 mM Hepes buffer (pH 7.4) containing 10 mM glucose, 145 mM sodium chloride, 4.5 mM potassium chloride, 1.2 mM magnesium chloride, 1.5 mM calcium chloride), which was used as crude synaptosome fraction.

5-HT uptake reaction was performed in a volume of 200 µl using a 96-well round bottom plate and pargyline (final concentration 10 µM) and sodium ascorbate (final concentration 0.2 mg/ml) were contained in the incubation buffer upon reaction and used.

Incubation buffer (total counting), non-labeled 5-HT (final concentration 10 µM, non-specific counting) and the diluted test compound (final concentration 300 nM) were added to each well. One-tenth quantity of the final volume of the synaptosome fraction was added and after preincubated at 37° C. for 10 minutes, tritium labeled 5-HT solution (final concentration 8 nM) was added and uptake reaction was started at 37° C. The uptake time was 10 minutes and the reaction was terminated by vacuum filtration through a 96-well fiber glass filter paper plate, and after the filter paper was washed with cold normal saline, it was dried enough and Microscint0 (Perkin-Elmer) was added to the filter and remaining radioactivity on the filter was measured.

Serotonin uptake inhibitory activity (%) was calculated from the radioactivity of total counting as 100%, of non-specific counting as 0%, and of counting obtained with test compound.

% of inhibition of 5-HT(%)=100−[(Count obtained with test compound−Nonspecific count(0% Uptake))/(Total count(100% Uptake)−Nonspecific count(0% Uptake))]×100

The results are shown in the next Table 24.

TABLE 24

| Test compound | Serotonin uptake inhibitory ratio (%)(300 nM) |
|---|---|
| Compound of Example 1 | 92.4 |
| Compound of Example 2 | 78.8 |
| Compound of Example 3 | 84.8 |
| Compound of Example 4 | 91.0 |
| Compound of Example 5 | 89.1 |
| Compound of Example 6 | 91.3 |
| Compound of Example 7 | 91.0 |
| Compound of Example 8 | 95.0 |
| Compound of Example 9 | 97.3 |
| Compound of Example 10 | 92.6 |
| Compound of Example 11 | 92.5 |
| Compound of Example 13 | 77.0 |
| Compound of Example 14 | 85.2 |
| Compound of Example 15 | 87.2 |

TABLE 24-continued

| Test compound | Serotonin uptake inhibitory ratio (%)(300 nM) |
|---|---|
| Compound of Example 16 | 86.7 |
| Compound of Example 17 | 86.3 |
| Compound of Example 18 | 91.1 |
| Compound of Example 19 | 86.3 |
| Compound of Example 20 | 92.8 |
| Compound of Example 21 | 81.4 |
| Compound of Example 22 | 90.8 |
| Compound of Example 23 | 95.5 |
| Compound of Example 24 | 97.5 |
| Compound of Example 25 | 91.9 |
| Compound of Example 26 | 92.0 |
| Compound of Example 27 | 94.0 |
| Compound of Example 28 | 95.3 |
| Compound of Example 30 | 95.8 |
| Compound of Example 31 | 96.3 |
| Compound of Example 32 | 96.9 |
| Compound of Example 33 | 94.3 |
| Compound of Example 34 | 94.2 |
| Compound of Example 35 | 93.4 |
| Compound of Example 36 | 97.4 |
| Compound of Example 37 | 97.7 |
| Compound of Example 38 | 96.7 |
| Compound of Example 39 | 99.2 |
| Compound of Example 40 | 91.6 |
| Compound of Example 41 | 95.1 |
| Compound of Example 64 | 73.0 |
| Compound of Example 65 | 72.9 |
| Compound of Example 66 | 74.1 |
| Compound of Example 67 | 93.9 |
| Compound of Example 68 | 95.7 |
| Compound of Example 69 | 96.3 |

Preparation Examples 100 g of a compound of the present invention, 40 g of Avicel (trade name, product of Asahi Chemical Industry Co., Ltd.), 30 g of corn starch and 2 g of magnesium stearate was mixed and polished and tableted with a pestle for glycocalyx R10 mm.

The obtained tablet was coated with a film using a film coating agent made up of 10 g of TC-5 (trade name, product of Shin-Etsu Chemical Co., Ltd., hydroxypropyl methylcellulose), 3 g of polyethylene glycol 6000, 40 g of castor oil and an appropriate amount of ethanol to produce a film coated tablet of the above composition.

The invention claimed is:

1. A pharmaceutical composition comprising a heterocyclic compound or a salt thereof represented by formula (1):

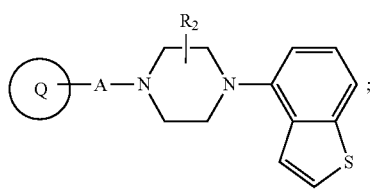

wherein ring Q is a bicyclic group selected from the group consisting of:

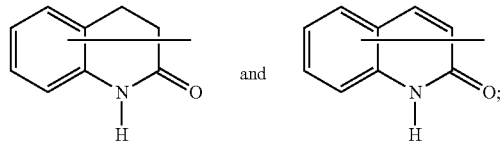

wherein the ring Q may have 1 to 3 substituents selected from the group consisting of a lower alkyl group, a lower alkenyl group, a lower alkynyl group, a hydroxy group, a lower alkoxy group, a halogenated lower alkyl group, a phenyl group, a phenyl lower alkyl group, a naphthyl lower alkyl group, a phenyl lower alkoxy group, a naphthyl lower alkoxy group, a benzoyl group, a lower alkenyloxy group, a lower alkanoyl group, a lower alkanoyloxy group, a cyclo $C_3$-$C_8$ alkyl group, a cyclo $C_3$-$C_8$ alkyl lower alkyl group, a halogen atom, a carbamoyl group which may have a lower alkyl group, a carboxy group, a lower alkoxycarbonyl group, an amino group which may have a lower alkanoyl group, a nitro group, a hydroxy lower alkyl group, an amino lower alkyl group which may have a lower alkyl group, a thienyl group, and a pyrrolidinyl lower alkyl group;

$R_2$ represents a hydrogen atom or a lower alkyl group; and

A represents —O-$A_1$-, wherein $A_1$ is a $C_1$-$C_6$ alkylene group; and a pharmaceutically acceptable carrier.

2. A pharmaceutical composition comprising a heterocyclic compound or a salt thereof represented by formula (1):

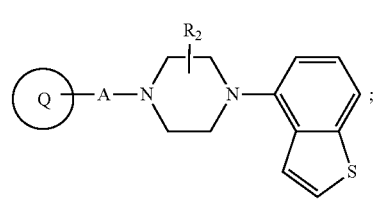

wherein ring Q is a bicyclic group selected from the group consisting of:

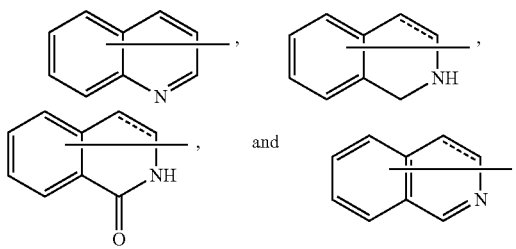

wherein the carbon-carbon === between the 3-position and 4-position of the bicyclic heterocyclic skeleton represents a single bond or a double bond;

wherein the ring Q may have 1 to 3 substituents selected from the group consisting of a lower alkyl group, a lower alkenyl group, a lower alkynyl group, a hydroxy group, a lower alkoxy group, a halogenated lower alkyl group, a phenyl group, a phenyl lower alkyl group, a naphthyl lower alkyl group, a phenyl lower alkoxy group, a naphthyl lower alkoxy group, a benzoyl group, a lower alkenyloxy group, a lower alkanoyl group, a lower alkanoyloxy group, a cyclo $C_3$-$C_8$ alkyl group, a cyclo $C_3$-$C_8$ alkyl lower alkyl group, a halogen atom, a carbamoyl group which may have a lower alkyl group, a carboxy group, a lower alkoxycarbonyl group, an amino group which may have a lower alkanoyl group, a nitro group, a hydroxy lower alkyl group, an amino lower alkyl group which may have a lower alkyl group, a thienyl group, and a saturated 5- to 6-membered heteromonocyclic group containing 1 to 2 nitrogen atoms-substituted lower alkyl group;

$R_2$ represents a hydrogen atom or a lower alkyl group; and

A represents —O-$A_1$-, wherein $A_1$ is a $C_1$-$C_6$ alkylene group; and a pharmaceutically acceptable carrier.

3. A pharmaceutical composition comprising 7-[4-(4-benzo[b]thiophen-4-yl-piperazin-1-yl)butoxy]-1H-quinolin-2-one and a pharmaceutically acceptable carrier.

4. The pharmaceutical composition according to claim 3, wherein the 7-[4-(4-benzo[b]thiophen-4-yl-piperazin-1-yl) butoxy]-1H-quinolin-2-one is present in the pharmaceutical composition in an amount ranging from 1% to 70% by weight.

5. The pharmaceutical composition according to claim 3, wherein the 7-[4-(4-benzo[b]thiophen-4-yl-piperazin-1-yl) butoxy]-1H-quinolin-2-one is present in the pharmaceutical composition in an amount ranging from 1% to 30% by weight.

6. The pharmaceutical composition according to claim 3, wherein the composition contains from 1 mg to 200 mg of 7-[4-(4-benzo[b]thiophen-4-yl-piperazin-1-yl)butoxy]-1H-quinolin-2-one.

7. The pharmaceutical composition according to claim 3, wherein the composition contains about 1 mg of 7-[4-(4-benzo[b]thiophen-4-yl-piperazin-1-yl)butoxy]-1H-quinolin-2-one.

8. The pharmaceutical composition according to claim 6, wherein the pharmaceutical composition is in the form of a tablet.

9. A method for treating major depression comprising administering a pharmaceutical composition according to claim 3.

10. A method for treating schizophrenia comprising administering a pharmaceutical composition according to claim 3.

11. A pharmaceutical composition comprising a pharmaceutically acceptable salt of 7-[4-(4-benzo[b]thiophen-4-yl-piperazin-1-yl)butoxy]-1H-quinolin-2-one and a pharmaceutically acceptable carrier.

12. The pharmaceutical composition according to claim 11, wherein the pharmaceutically acceptable salt of 7-[4-(4-benzo[b]thiophen-4-yl-piperazin-1-yl)butoxy]-1H-quinolin-2-one is present in the pharmaceutical composition in an amount ranging from 1% to 70% by weight.

13. The pharmaceutical composition according to claim 11, wherein the pharmaceutically acceptable salt of 7-[4-(4-benzo[b]thiophen-4-yl-piperazin-1-yl)butoxy]-1H-quinolin-2-one is present in the pharmaceutical composition in an amount ranging from 1% to 30% by weight.

14. The pharmaceutical composition according to claim 11, wherein the composition contains from 1 mg to 200 mg of the pharmaceutically acceptable salt of 7-[4-(4-benzo[b] thiophen-4-yl-piperazin-1-yl)butoxy]-1H-quinolin-2-one.

15. The pharmaceutical composition according to claim 11, wherein the composition contains about 1 mg of the pharmaceutically acceptable salt of 7-[4-(4-benzo[b]thiophen-4-yl-piperazin-1-yl)butoxy]-1H-quinolin-2-one.

16. The pharmaceutical composition according to claim 14, wherein the pharmaceutical composition is in the form of a tablet.

17. A method for treating major depression comprising administering a pharmaceutical composition according to claim 11.

18. A method for treating schizophrenia comprising administering a pharmaceutical composition according to claim 11.

* * * * *

UNITED STATES PATENT AND TRADEMARK OFFICE
CERTIFICATE OF CORRECTION

PATENT NO. : 9,839,637 B1
APPLICATION NO. : 15/697196
DATED : December 12, 2017
INVENTOR(S) : Hiroshi Yamashita et al.

It is certified that error appears in the above-identified patent and that said Letters Patent is hereby corrected as shown below:

On the Title Page

(75) Inventors: please add the following inventors:
Yasuo OSHIRO, Tokushima (JP) and Shinichi TAIRA, Tokushima (JP)

Signed and Sealed this
Ninth Day of July, 2019

Andrei Iancu
*Director of the United States Patent and Trademark Office*